United States Patent
Gilbert et al.

(10) Patent No.: US 9,649,147 B2
(45) Date of Patent: May 16, 2017

(54) ELECTROSURGICAL DEVICE AND METHODS

(71) Applicant: Eximis Surgical, LLC, Louisville, CO (US)

(72) Inventors: James A. Gilbert, Boulder, CO (US); Steven C. Rupp, Arvada, CO (US); William N. Gregg, Superior, CO (US); Kristin D. Johnson, Louisville, CO (US); Dirk Johnson, Louisville, CO (US)

(73) Assignee: EXIMIS SURGICAL, LLC, Louisville, CO (US)

( * ) Notice: Subject to any disclaimer, the term of this patent is extended or adjusted under 35 U.S.C. 154(b) by 0 days.

(21) Appl. No.: 15/266,903

(22) Filed: Sep. 15, 2016

(65) Prior Publication Data
US 2017/0079708 A1    Mar. 23, 2017

Related U.S. Application Data

(60) Provisional application No. 62/220,179, filed on Sep. 17, 2015, provisional application No. 62/279,565, (Continued)

(51) Int. Cl.
*A61B 18/12*    (2006.01)
*A61B 18/14*    (2006.01)
(Continued)

(52) U.S. Cl.
CPC .... *A61B 18/1206* (2013.01); *A61B 17/00234* (2013.01); *A61B 17/320068* (2013.01);
(Continued)

(58) Field of Classification Search
CPC .............. A61B 18/1206; A61B 18/149; A61B 18/1489; A61B 18/1487;
(Continued)

(56) References Cited

U.S. PATENT DOCUMENTS

| 4,368,734 A | 1/1983 | Banko |
| 5,312,416 A | 5/1994 | Spaeth et al. |

(Continued)

FOREIGN PATENT DOCUMENTS

| EP | 1004277 A1 | 5/2000 |
| WO | 2005122938 A1 | 12/2005 |

(Continued)

OTHER PUBLICATIONS

Ouyang, Bo, "Office Action Re U.S. Appl. No. 14/805,358", Jun. 14, 2016, p. 100, Published in: US.

(Continued)

*Primary Examiner* — Michael Peffley
(74) *Attorney, Agent, or Firm* — Neugeboren O'Dowd PC

(57) ABSTRACT

A tissue segmentation device, controller, and methods therefore are disclosed. The device has an active electrode, a return electrode, a mechanical force application mechanism, voltage and current sensors, and a controller. The controller is configured to control a power output of the segmentation device. The controller has a processing component, responsive to the sensors, configured to execute the following: (a) derive a power factor of power applied to the at least one electrode; and (b) responsive to the deriving a power factor, assign a circuit status to a circuit comprising the at least one electrode. IF (PF≈0) and ((Vrms/Irms)≥T), THEN the circuit status is "open". IF (PF≈0) and ((Vrms/Irms)<T), THEN the circuit status is "short". PF is the power factor. T is a threshold value.

30 Claims, 68 Drawing Sheets

Related U.S. Application Data filed on Jan. 15, 2016, provisional application No. 62/327,852, filed on Apr. 26, 2016.

(51) Int. Cl.
*A61B 17/00* (2006.01)
*A61B 17/32* (2006.01)
*A61B 18/00* (2006.01)

(52) U.S. Cl.
CPC .. *A61B 18/149* (2013.01); *A61B 2017/00039* (2013.01); *A61B 2017/00287* (2013.01); *A61B 2018/00184* (2013.01); *A61B 2018/00601* (2013.01); *A61B 2018/00648* (2013.01); *A61B 2018/00666* (2013.01); *A61B 2018/00702* (2013.01); *A61B 2018/00827* (2013.01); *A61B 2018/00892* (2013.01); *A61B 2018/144* (2013.01); *A61B 2018/1435* (2013.01)

(58) Field of Classification Search
CPC A61B 2018/00184; A61B 2018/00702; A61B 2018/144; A61B 2018/00601; A61B 2018/00666; A61B 2018/00827; A61B 2018/1435; A61B 17/00234; A61B 17/320068
See application file for complete search history.

(56) References Cited

U.S. PATENT DOCUMENTS

| | | | |
|---|---|---|---|
| 5,354,303 A | 10/1994 | Spaeth et al. | |
| 5,569,284 A | 10/1996 | Young et al. | |
| 5,611,803 A | 3/1997 | Heaven et al. | |
| 5,643,283 A | 7/1997 | Younker | |
| 5,735,289 A | 4/1998 | Pfeffer et al. | |
| 5,814,044 A | 9/1998 | Hooven | |
| 5,836,953 A | 11/1998 | Yoon | |
| 5,868,740 A | 2/1999 | LeVeen et al. | |
| 5,968,040 A | 10/1999 | Swanson et al. | |
| 6,280,450 B1 | 8/2001 | McGuckin | |
| 6,383,196 B1 | 5/2002 | Leslie et al. | |
| 6,537,273 B1 | 3/2003 | Sosiak et al. | |
| 6,685,628 B2 | 2/2004 | Vu | |
| 6,740,079 B1 * | 5/2004 | Eggers | A61B 18/1206 606/34 |
| 6,752,811 B2 | 6/2004 | Chu et al. | |
| 7,004,942 B2 | 2/2006 | Laird et al. | |
| 7,052,501 B2 | 5/2006 | McGuckin et al. | |
| 7,244,255 B2 * | 7/2007 | Daners | A61B 18/1206 606/32 |
| 7,474,909 B2 | 1/2009 | Phan et al. | |
| 7,753,920 B2 | 7/2010 | McGuckin et al. | |
| 8,192,436 B2 | 6/2012 | Schmitz et al. | |
| 8,377,054 B2 * | 2/2013 | Gilbert | H03H 17/0275 606/34 |
| 8,386,006 B2 | 2/2013 | Schouenborg | |
| 8,758,349 B2 | 6/2014 | Germain et al. | |
| 8,920,412 B2 * | 12/2014 | Fritz | A61B 18/1206 606/34 |
| 2002/0068943 A1 | 6/2002 | Chu et al. | |
| 2002/0095152 A1 | 7/2002 | Ciarrocca et al. | |
| 2004/0002683 A1 | 1/2004 | Nicholson et al. | |
| 2004/0162554 A1 | 8/2004 | Lee et al. | |
| 2005/0267492 A1 | 12/2005 | Poncet et al. | |
| 2006/0167470 A1 | 7/2006 | McGuckin | |
| 2007/0088370 A1 | 4/2007 | Kahle et al. | |
| 2008/0027428 A1 | 1/2008 | Palanker et al. | |
| 2008/0221604 A1 | 9/2008 | Kondoh et al. | |
| 2009/0149851 A1 | 6/2009 | Craig | |
| 2009/0149865 A1 | 6/2009 | Schmitz et al. | |
| 2009/0192510 A1 | 7/2009 | Bahney | |
| 2009/0326546 A1 | 12/2009 | Mohamed et al. | |
| 2010/0145329 A1 | 6/2010 | Bystryak et al. | |
| 2011/0040314 A1 | 2/2011 | Mcguckin, Jr. et al. | |
| 2011/0087235 A1 | 4/2011 | Taylor et al. | |
| 2011/0184311 A1 | 7/2011 | Parihar et al. | |
| 2011/0184432 A1 | 7/2011 | Parihar et al. | |
| 2011/0184433 A1 | 7/2011 | Parihar et al. | |
| 2011/0184435 A1 | 7/2011 | Parihar et al. | |
| 2012/0083796 A1 | 4/2012 | Grover et al. | |
| 2013/0041373 A1 | 2/2013 | Laufer | |
| 2013/0123783 A1 | 5/2013 | Marczyk et al. | |
| 2013/0131445 A1 | 5/2013 | Zerfas et al. | |
| 2014/0052018 A1 | 2/2014 | Hawkins | |
| 2014/0249541 A1 | 9/2014 | Kahle et al. | |
| 2014/0276801 A1 | 9/2014 | Juergens et al. | |
| 2014/0276913 A1 | 9/2014 | Tah et al. | |
| 2014/0288486 A1 | 9/2014 | Hart et al. | |
| 2016/0030073 A1 | 2/2016 | Isakov et al. | |

FOREIGN PATENT DOCUMENTS

| | | |
|---|---|---|
| WO | 2014158880 A1 | 10/2014 |
| WO | 2015084769 A1 | 6/2015 |

OTHER PUBLICATIONS

Ouyang, Bo, "Office Action Re U.S. Appl. No. 14/805,358", Dec. 24, 2015, p. 40, Published in: US.

Schneider, Laura A., "Response to Office Action Re U.S. Appl. No. 14/805,358", Mar. 2, 2016, p. 16, Published in: US.

Schneider, Laura A., "Response to Office Action Re U.S. Appl. No. 14/805,358", Jul. 5, 2016, p. 17, Published in: US.

Olympus America Medical, "Four-Wire Basket", Retrieved from http://medical.olympusamerica.com/products/basket/four-wire-basket, Known to exist as early as Oct. 1, 2015, p. 2, Published in: US.

Applied Medical, "Alexis Contained Extraction System", Retrieved from http://appliedmedical.com/products/ Alexis_CES.aspx , Known to exist as early as Oct. 1, 2015, p. 1, Published in: US.

Barbieri, Robert L., "Options for reducing the use of open power morcellation of uterine tumors", Retrieved from.http://www.mdedge.com/obgmanagement/article/80652/surgery/options-reducing-use-open-power-morcellation-uterine-tumors, Mar. 26, 2014, p. 5.

Covidien, "Principals of Electrosurgery", Known to exist as early as Sep. 30, 2015, p. 28, Publisher: Covidien AG, Published in: US.

Duck, A .Francis, "Physical Properties of Tissue", 2012, p. 5, Publisher: IPEM, Published in: US.

Covidien, Specimen Retrieval Products, Retrieved from http://www.covidien.com/surgical/products/hand-instruments-and-ligation/specimen-retrieval-products, Known to exist as early as Oct. 1, 2016, p. 2, Published in: US.

Covidien, "Endo Catch 15mm Specimen Pouch", Retrieved from http://products.covidien.com/pages.aspx.?page=ProductDetail&id=134638,&cat=Devices&cat2=Model, Known to exist as early as Oct. 1, 2016 , p. 2, Published in: US.

Covidien, "Endo Catch Gold", Retrieved from http://products.covidien.com/pages.aspx.?page=ProductDetail&id=174186&cat=Devices&cat2=Model, Known to exist as early as Oct. 1, 2015, p. 1, Published in: US.

Ethicon, "Endopouch Specimen Retrieval Bag", Retrieved from http://www.ethicon.com/healthcare-professionals/products/other/lap-hand/specimen-retrieval, Known to exist as early as Oct. 1, 2015, p. 2, Published in: US.

Friedrichs, et al., "A New Dual Current-Mode Controller Improves Power Regulation in Electrosurgical Generators", "Transactions on Biomedical Curcuits and Systems", Feb. 2012, p. 6, Publisher: IEEE, Published in: US.

Hackethal, Veronica, "Morcellation Isolation Bag: Expert Quesitons Technique", Retrieved from http://www. medscape.com/viewarticle/829476, Aug. 6, 2014, p. 2, Publisher: Medscape.

Heim, Warren P., "How Electrosurgery Really Cuts Tissue", Jan. 8, 2015, p. 3, Publisher: Team Medical, LLC, Published in: US.

Applied Medical, "Inzii Retrieval Systems", Retrieved from http://www.appliedmedical.com/Products/Inzii.aspx, Known to exist as early as Oct. 1,2015, p. 1, Published in: US.

(56) References Cited

OTHER PUBLICATIONS

Isakov, et al., "A New Laparoscopic Morcellator Using an Actuated Wire Mesh and Bag", "Journal of Medical Devices", Mar. 2014, p. 7, Publisher: ASME, Published in: US.
Young, Lee W., "International Search Report and Written Opinion re Application No. PCTUS1541407", Nov. 27, 2015, p. 14, Published in: WO.
Karl Storz, "Urology", Retrieved from https://www.karlstorz.com/us/en/urology.htm, Known to exist as early as Oct. 1, 2015 , p. 7, Published in: US.
Cook Medical, "LapSac Surgical Tissue Pouch", Retrieved from https://www.cookmedical.com/products/uro_lapsac_webds/, Known to exist as early as Oct. 1, 2015, p. 2, Published in: US.
Lattis Surgical, "Lattis Contained Tissue Extraction (CTE) Device", Retrieved from http://www.lattissurgical.com/lattis-cte-vs.-morcellation.html, Known to exist as early as Oct. 1, 2015, p. 1.
Lina Medical, "LinA Bipolar Loop", Retrieved from http://www.linamed.com/products/lina-loop-range/lina-bipolar-loop/, Known to exist as early as Oct. 1, 2015, p. 6, Published in: US.
Lina Medical, "LiNA Gold Loop", Retrieved from http://www.linamed.com/products/lina-loop-range/lina-gold-loop/, Known to exist as early as Oct. 1, 2015, p. 6.
Lina Medical, "LiNA Gold Loop HC", Retrieved from http://www.lina-medical.com/products/lina-loop-range/lina-gold-loop-hc/, Known to exist as early as Oct. 1, 2015 , p. 6, Published in: US.
Mechcatie, Elizabeth, "Study finds insufflated collection bag successfully used in power morcellation cases", Retrieved from http://www.mdedge.com/obgynnews/article/86182/surgery/study-finds-insufflated-collection-bag-successfully-used-power, Aug. 5, 2014, p. 2, Publisher: Ob.Gyn. News.
Tissue Extraction Task Force, "Morcellation During Uterine Tissue Extraction", "AAGL Advancing Minimally Invasive Gynecology Worldwide", p. 15, Publisher: AAGL.
Palanker, et al., "Electrosurgery With Cellular Precision", "Transactions on Biomedical Engineering", Feb. 2008, p. 4, Publisher: IEEE.
Copenheaver, Blaine R., "International Search Report and Written Opinion re Application No. PCT/2014/020649", Mar. 14, 2013, p. 15, Published in: US.
Pearce, John A., "Electrosurgery", "Biomedical Engineering Program", 1986, p. 20, Publisher: University of Texas at Austin, Published in: US.
Olympus America Medical, "Handpiece Morcellators PKS PlasmaSORD", Retrieved from http://medical.olympusamerica.com/products/handpiece/pks-plasmaord-962000pk, Known to exist as early as Oct. 1, 2015, p. 2, Published in: US.
Olympus America Medical, "Handpiece PK Instruments PKS Bill", Retrieved from http://medical.olympusamerica.com/products/pks-bill-bl0533, Known to exist as early as Oct. 1, 2015, p. 2.
Olympus America Medical, "Loop Ligating Device PolyLoop", Retrieved from http://medical.olympusamerica. com/products/polyloop, Known to exist as early as Oct. 1, 2015, p. 2, Published in: US.
Cook Medical, "Disposable Hysteroscopic Polyp Snare", Retrieved from https://www.cookmedical.com/products/wh_dhps_webds/, Known to exist as early as Oct. 1, 2015, p. 2, Published in: US.
Gardner, Elizabeth K., "Purdue Technology Used in First Fluorescence-Guided Ovarian Cancer Surgery", Sep. 18, 2011, p. 4, Published in: US.
Olympus America Medical, "Resection in Saline Electrodes", Retrieved from http://medical.olympusamerica.com/products/resection-saline-electrodes, Known to exist as early as Oct. 1, 2015, p. 2, Published in: US.
Olympus America Medical, "SnareMaster", Retrieved from http://medical.olympusamerica.com/products/snaremaster, Known to exist as early as Oct. 1, 2015, p. 2.
Olympus America Medical, "Stiff Wire Basket", Retrieved from http://medical.olympusamerica.com/products/basket/stiff-wire-basket-fg-402q, Known to exist as early as Oct. 1, 2015, p. 1, Published in: US.
Megger, "A Stitch in Time the Complete Guide to Electical Insulation Testing", "Retrieved from https://www.instrumart.com/assets/Megger-insulationtester.pdf", Jun. 8, 2016, p. 67.

* cited by examiner

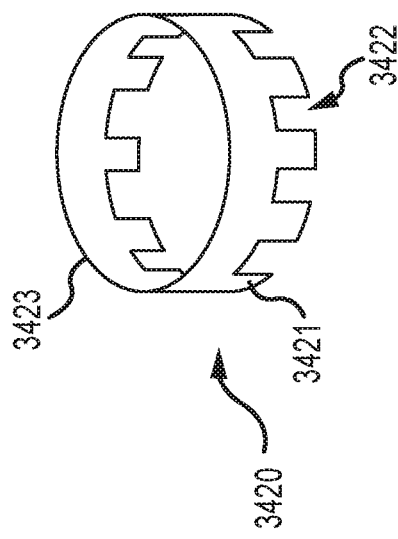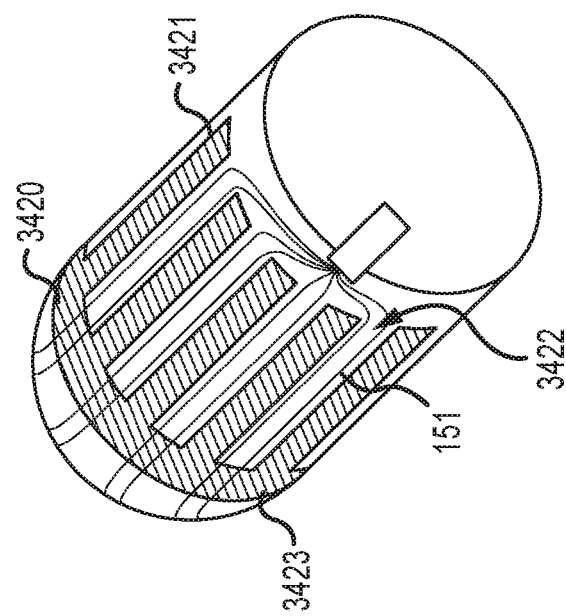
FIG. 34

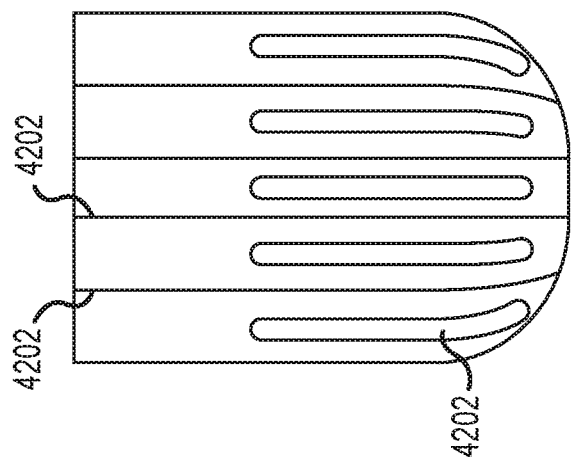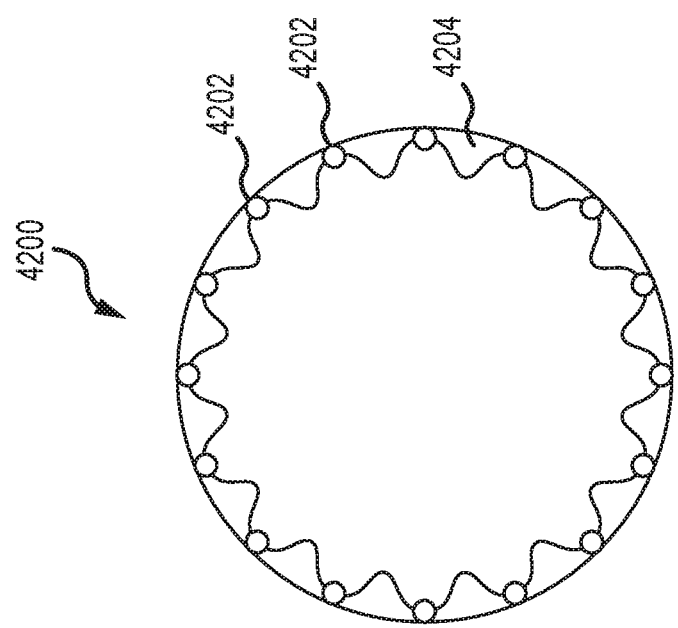
FIG. 42

ELECTROSURGICAL DEVICE AND METHODS

CROSS-REFERENCE TO RELATED APPLICATIONS

This application claims priority to U.S. Provisional Application No. 62/220,179 filed Sep. 17, 2015 and entitled "Electrosurgical Device and Methods," U.S. Provisional Application No. 62/279,565 filed Jan. 15, 2016 and entitled "Electrosurgical Device and Methods," and U.S. Provisional Application No. 62/327,852 filed Apr. 26, 2016 and entitled "Electrosurgical Device and Methods," the entire disclosures of which are hereby incorporated by reference for all proper purposes, as if fully set forth herein.

BACKGROUND

Field

The present invention relates generally to surgical devices and methods, and more specifically to electrosurgical devices and methods.

Background

In U.S. patent application Ser. No. 14/805,358 entitled Large Volume Tissue Reduction and Removal System and Method, to Johnson et al., a method and device for removing large tissue masses from a patient are described. However, there remains a need for other new and innovative features.

SUMMARY

An exemplary tissue segmentation device is disclosed. The exemplary device has at least one active electrode, a return electrode, a mechanical force application mechanism, a voltage sensor, a current sensor, and a controller. The exemplary controller is configured to control a power output of the segmentation device. The exemplary controller has a processing component, responsive to the voltage sensor and the current sensor, configured to execute the following: (a) derive a power factor of power applied to the at least one electrode; and (b) responsive to the deriving a power factor, assign a circuit status to a circuit comprising the at least one electrode, according to the following: IF (PF≈0) and ((Vrms/Irms)≥T), THEN the circuit status is "open". IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

An exemplary controller for a tissue segmentation device having at least one active electrode, a return electrode, a voltage sensor, a current sensor, and a mechanical force application mechanism is disclosed. The exemplary controller has a processing component, responsive to the voltage sensor and the current sensor, configured to execute the following: (a) derive a power factor of power applied to the at least one electrode; and (b) responsive to the deriving a power factor, assign a circuit status to a circuit comprising the at least one electrode according to the following: IF (PF≈0) and ((Vrms/Irms)≥T), THEN the circuit status is "open". IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

An exemplary method of tissue segmentation is disclosed. The exemplary method includes providing a tissue segmentation device having at least one active electrode, a return electrode, a mechanical force application mechanism, a voltage sensor, and a current sensor. The exemplary method includes deriving a power factor of power applied to the at least one electrode, and responsive to deriving a power factor, assigning a circuit status to a circuit comprising the at least one electrode according to the following: IF (PF≈0) and ((Vrms/Irms)≥T), THEN the circuit status is "open"; IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

Another exemplary tissue segmentation device is disclosed. The exemplary device has at least one active electrode, a return electrode, a mechanical force application mechanism, a voltage sensor, a current sensor, and a controller. The exemplary controller is configured to control a power output of the segmentation device. The exemplary controller has a processing component, responsive to the voltage sensor and the current sensor, configured to execute the following: (a) derive an impedance to power applied to the at least one electrode; and (b) responsive to the deriving the impedance, assign a circuit status to a circuit comprising the at least one electrode, according to the following: IF (Z>T1), THEN the circuit status is "open"; and IF (Z<T2), THEN the circuit status is "short"; where Z is the impedance; T1 is a first threshold value; and T2 is a second threshold different from the first threshold value.

BRIEF DESCRIPTION OF THE DRAWINGS

FIG. 34 illustrates a partial transparent perspective view and a partial transparent side view of a removal bag;

FIG. 42 illustrates top and side views of a tissue removal bag;

FIG. 87b illustrates various features of the wrap-around removal bag in FIG. 87a, and FIG. 87c illustrates various features of the wrap-around removal bag in FIG. 87a;

FIG. 97b illustrates a side section view of the components in FIG. 97a, and FIG. 97c illustrates a side-section view of the components in FIG. 97a;

DETAILED DESCRIPTION

The word "exemplary" is used herein to mean "serving as an example, instance, or illustration." Any embodiment described herein as "exemplary" is not necessarily to be construed as preferred or advantageous over other embodiments.

Figure 1:
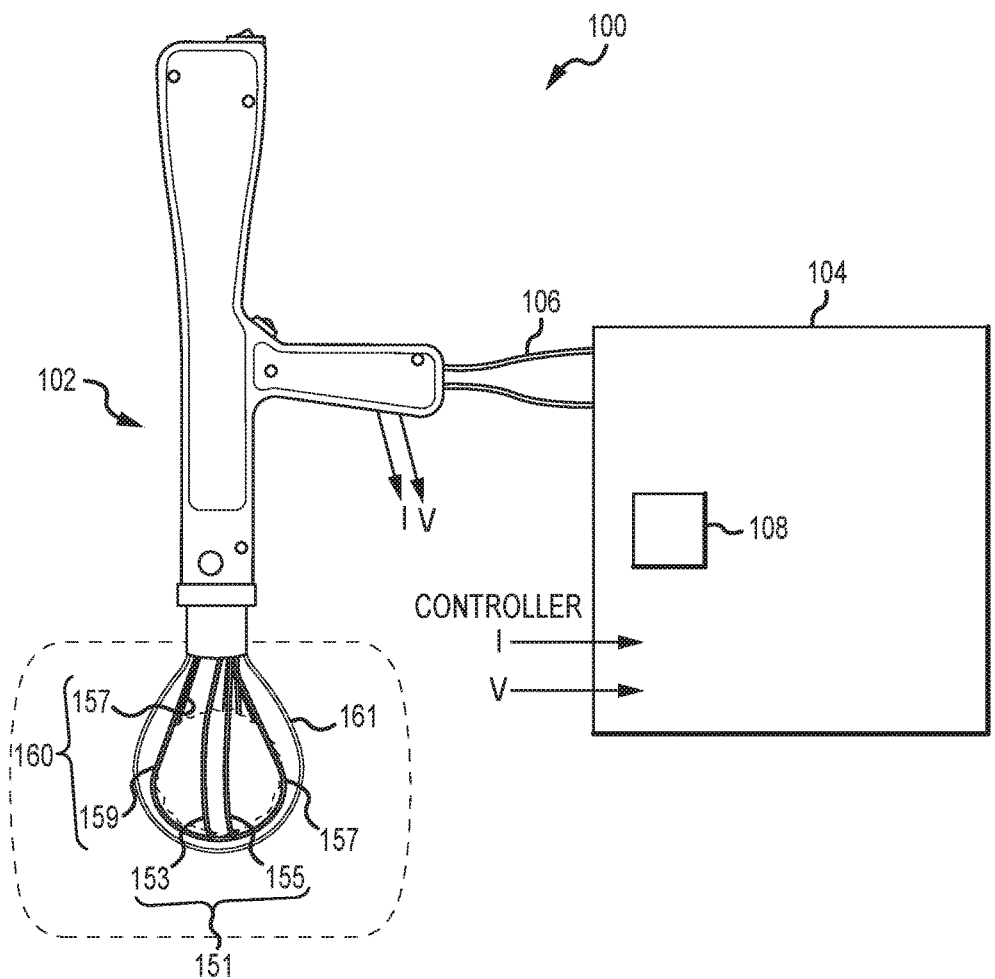
FIG. 1 illustrates a tissue segmentation device according to some embodiments.

In one exemplary application, and as illustrated in FIG. 1, an advanced electrosurgical system 100 may be provided. The system 100 may be configured to perform some or all of the functions, such as tissue segmentation and/or removal, described in Applicant's International Application PCT/US15/41407, entitled Large Volume Tissue Reduction and Removal System and Method, filed on Jul. 21, 2015, and having a priority date of Jul. 22, 2014, the entire contents of which are incorporated herein by reference for all purposes, as if fully set forth herein. The system 100 may include an electrosurgical device 102 and a generator 104 coupled together by a number of leads 106. The generator 104 may include a controller 108.

Except as where otherwise stated herein, the term "segmentation device" shall be understood to include a device for dividing tissue, and may include a mechanical segmentation action, and/or an electrosurgical dissection action, for example a bipolar segmentation action, or a monopolar action.

Figure 2:
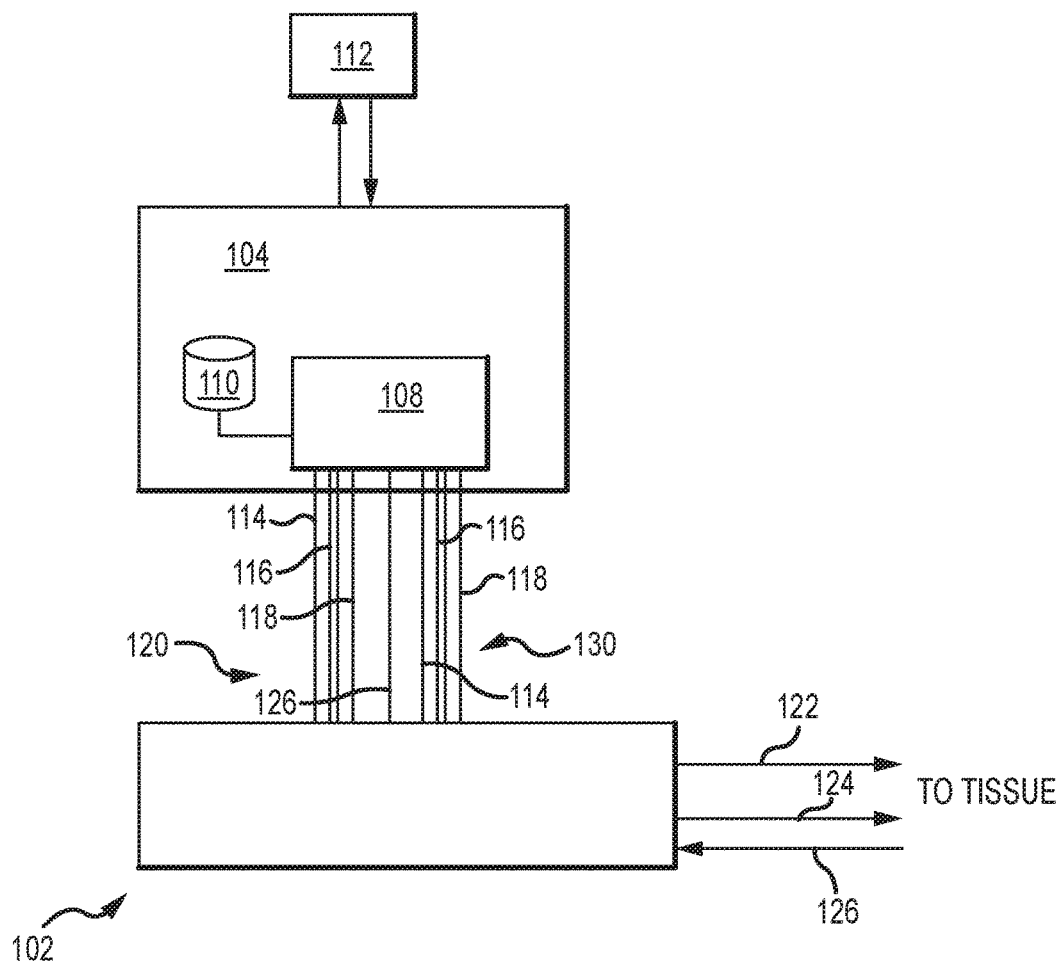
FIG. 2 is a diagram of some electrical and mechanical components of an exemplary electrosurgical device.

In some embodiments, and as illustrated in FIG. 2, the generator 104 may include a datastore 110 for storing one or more sets of tissue segmentation parameters. The tissue segmentation parameters may include parameters associated with a normal or expected response during an electrosurgical procedure, and may be related to tissue segmentation voltage, current, power factor angle, impedance, power, energy, electrode or wire rate of travel, electrode or wire distance of travel, and/or mechanical segmentation force applied to tissue by the electrode(s) or wire(s). The datastore 110 may be a component of or separate from the controller 108.

The tissue segmentation parameters are obtained by analytical and/or experimental methods and are targeted boundary values that ensure optimal operation of the system 100 or components thereof, preferably while maintaining a safe tissue temperature.

In some embodiments, a tissue segmentation voltage parameter Vmin is defined as the minimum voltage required to begin the initiation of a segmentation cut by providing an arc through an active electrode exposure area between the electrode/wire and the tissue. In some embodiments, the tissue segmentation voltage parameter Vmin is defined as the minimum voltage required to sustain the segmentation cut. The tissue segmentation voltage parameter Vmin can be calculated by considering the dielectric value of the electrode or wire coating, the coating thickness, and the uniformity of the coating. The tissue segmentation voltage parameter Vmin may also or alternatively be determined experimentally by measuring the voltage between the electrode/wire and return at initiation and/or during a segmentation cut of a control tissue.

In some embodiments, the tissue segmentation current parameter Imin is defined as the minimum current required to meet the current density needed to create a tissue segmentation cut. In some embodiments, the tissue segmentation current parameter Imin is defined as the minimum current required to sustain a cutting effect. The tissue segmentation current parameter Imin value may be calculated by multiplying a known current density that achieves a desired cutting effect in a control tissue by an active electrode surface area. The tissue segmentation current parameter Imin may also or alternatively be determined experimentally by increasing the RF current applied to a control tissue until cutting occurs and measuring the current delivered to the control tissue. In some embodiments, the control tissue may be tissue of the patient during an electrosurgical procedure.

In some embodiments, a power factor angle PFAcut variable is measured during an electrosurgical procedure on a patient. The power factor angle PFAcut variable may be determined by measuring the phase angle between the voltage and current waveforms delivered to the electrosurgical device, and is a representation of the complex load impedance provided by the system, including the tissue, to the generator during the electrosurgical procedure. The power factor angle PFAcut variable may be measured and tracked, to determine if a short circuit condition or open circuit condition between an active electrode or active segmentation wires and a return electrode exists.

A direct impedance measurement from the controller 108 to determine a short circuit is difficult as the series cable inductance becomes dominant Applicant has determined that the power factor angle PFAcut during a short circuit will appear mostly inductive and have a phase angle near 90 degrees. Therefore, a short circuit power factor angle parameter PFAshort may be experimentally determined by measuring the lowest, or least inductive, power factor angle PFAcut variable while a short circuit is intentionally applied between the active and return electrodes during RF activation. The lowest power factor angle PFAcut variable may then be defined as the short circuit power factor angle parameter PFAshort.

Similarly, a direct impedance measurement for an open circuit is difficult, due to the parallel system capacitance. The power factor angle PFAcut variable during an open circuit will appear mostly capacitive and have a phase angle near −90 degrees. The open circuit power factor angle parameter PFAopen, may therefore be experimentally determined by measuring the highest, or least capacitive, power factor angle PFAcut variable while an open circuit condition is known to exist between the active and return electrodes during RF activation. The highest power factor angle PFAcut variable may then be defined or assumed as the open circuit power factor angle parameter PFAopen.

In some embodiments, an open circuit and/or short circuit may be determined using the power factor PF instead of the power factor angle PFA previously described. The power factor is the ratio of the actual power being delivered, or real power Preal, to the product of the RMS voltage Vrms and the RMS current Irms. The product of the RMS voltage Vrms and the RMS current Irms may be referenced herein as the apparent power. This ratio is 1.0 when the real power and apparent power are the same, as would be the case when a purely resistive load is applied. As a more inductive or a more capacitive load is applied, the phase shift of these loads reduces the value of the ratio to approach zero as the real power reduces but the apparent power remains the same. In this manner, the power factor PF may be used instead of the power factor angle PFA, thereby providing or enabling the detection of a minimum power factor threshold for cutting, PFcut, a short circuit power factor threshold, PFshort and an open circuit power factor threshold, PFopen.

As illustrated in FIG. 7A, to measure, detect, and/or derive the Power Factor PF, the controller 108, 708 may be coupled to or responsive to voltage and current sensors (not illustrated) that are designed with a bandwidth that will accommodate a fundamental RF frequency of the wire(s) (e.g. wire(s) 151 in FIG. 1).

In some embodiments, an analog/digital converter (A/D converter) may be provided and coupled to a field programmable gate array (FPGA), microcontroller, or other processing component 712 to sample the voltage and current sensors. A sampling rate of at least greater than 2 times the fundamental RF frequency may be provided in some embodiments. In some embodiments, the sampling rate may be greater than 5 times the fundamental RF frequency, thereby reducing sampling error.

The controller 108, 708 may calculate the average real power of the electrical load by using the instantaneous sampled voltage multiplied by the instantaneous sampled current values, averaged over a sampling window having N cycles of the fundamental RF Frequency. Those skilled in the art understand that the value of N may be selected based on the accuracy of the measurement; as N increases, the accuracy of the measurement increases. The value of N may be selected based on the system response time. As N decreases, the system response time will decrease. The value of N may be selected based on simplification of the calculations, for example selecting N as a power of 2. N may be selected based on other means, including, but not limited to, balancing system response time, simplification of calculations, and/or accuracy of the measurements.

Continuing with FIG. 7A, the controller 108, 708 may calculate or derive the RMS voltage Vrms by squaring the instantaneous sampled voltage averaged over a window of N cycles of the fundamental RF frequency. The controller 108, 708 may calculate or derive the RMS current Irms by squaring the instantaneous sampled current averaged over a window of N cycles of the fundamental RF frequency.

Using the calculated values of voltage Vrms, current Irms, and power Preal previously described, the power factor, PF, is the real power, Preal, divided by the product of the RMS voltage Vrms and RMS current Irms. As previously described, if the load impedance is an open or short circuit, the power factor PF, approaches zero.

If the apparent impedance Z (Z=Vrms/Irms), is above a predetermined threshold and the power factor PF is near zero this identifies an open circuit. In some embodiments, an open circuit may indicate a cut is complete. In some embodiments, an open circuit in combination with a detected distance of proximal travel of one or more wires/electrodes 151 may indicate a cut(s) is complete.

Continuing with FIG. 7A, if the apparent impedance Z is below this threshold, and the power factor PF is near zero, this indicates a short circuit between an active electrode or wire (e.g. wire 122, 124) and a return electrode 126.

In some embodiments, the average real power Preal may be detected or derived using the voltage and current sensors as previously described; however the output of the sensors may be connected to an analog multiplier to obtain the instantaneous real power Preal. The output of the multiplier may then be coupled to an analog circuit with an inherent capacitance to provide the window for averaging the real power Preal. The average RMS voltage Vrms and RMS current Irms may also be measured using an analog RMS voltage and RMS current sensing circuit that provides an RMS analog output. The RMS output of these sensors may also be connected to a multiplier to obtain the instantaneous apparent power and, as previously described for the real power measurement, the output of the multiplier may be connected to an analog circuit with an inherent capacitance to provide the window for averaging the apparent power. This circuit may be read with an A/D converter so that the power factor PF can be easily calculated by dividing the average real power analog output by the average apparent power output.

In some embodiments, the output of the real power multiplier and the output of the apparent power multiplier may be coupled directly to an analog divider to obtain the instantaneous power factor PF. This output may be read with an A/D converter to directly measure the power factor, or may be connected to an analog circuit with an inherent capacitance to provide a window for averaging the power factor.

In some embodiments, a purely analog method of power factor calculation may include the use of comparators as threshold detectors to provide an analog short circuit and/or open circuit detection that does not require a microprocessor, FPGA or other software, or RTL programmable instruction set to perform.

The impedance Zcut variable may be deduced from the voltage V and current I variables (see, e.g. FIG. 2) at leads 114, 116, and may be used to compare against a minimum tissue impedance parameter Zmin and a maximum tissue impedance parameter Zmax. The tissue impedance parameters Zmin, Zmax are affected by the active electrode surface area, the coating properties of the active electrode wire, the tissue type, and the tissue hydration, and may be experimentally determined by measuring the range of impedance values during a cutting process in a control tissue or the patient tissue under controlled conditions.

Relatedly, the power variable Pcut may be deduced from the voltage V and current I values (see FIG. 2) at leads 114, 116, and may be compared against the minimum power parameter Pmin and the maximum power parameter Pmax. The minimum power parameter Pmin may be determined or defined by the minimum power Pmin required to meet the power density needed to initiate or sustain a cutting effect, as previously described herein. The maximum power parameter Pmax may be determined or defined as a value that will deliver a segmentation or cutting effect without excessive charring, desiccation of tissue, and/or steam or smoke generation. In some embodiments, the minimum and maximum power parameters Pmin, Pmax may be calculated by multiplying the desired power densities by the active electrode surface area. The active electrode surface area may be defined or determined as illustrated and described in Applicant's co-pending application PCT/US15/41407. The minimum power parameter values Pmin, may also be determined experimentally by adjusting RF power until the desired cutting effect is observed and measuring the power delivered to the tissue.

In some embodiments, a method of improving the power efficiency delivered from the generator to the tissue may be provided. In some embodiments, the controller may use power factor correction. Power factor correction may be achieved by the use of a variable capacitance that may be adjusted by the controller (see e.g. FIG. 2) to cancel out the cable inductance of the system. The controller 108 may continuously monitor the power factor phase angle PFAcut and may use this value to adjust a variable capacitance applied in parallel between an active electrode or wire 122, 124 and a return electrode 126 coupled to the controller 108. This changes the PFAcut angle allowing the controller to control the phase to achieve a near 0 degree phase angle resulting in the maximum power efficiency to perform the cut. This technique can be used to maximize the power delivered to the tissue which can provide faster cutting or allow larger tissue specimens to be cut effectively.

The energy variable Etissue delivered to the tissue, is defined by the accumulated energy applied to the tissue during the RF activation. The energy variable Etissue may be deduced by accumulating the real power component from the voltage V and current I values (see FIG. 2) such as at leads 114, 116 on a cycle by cycle basis. Using the energy variable Etissue delivered to the tissue, a relationship between the energy delivered to the tissue and a resulting temperature rise of the tissue specimen may be determined using a control tissue sample of known volume and/or size. Using this relationship, the energy variable Etissue may be compared to a maximum energy parameter Emax, to ensure that the tissue temperature does not exceed an intended value or beyond a temperature deemed safe.

The rate of travel variable Rtravel is defined as the distance of travel of a tensioning mechanism or cutting electrode or wire over a fixed period of time, and may be compared to a minimum rate of travel parameter Rmin and a maximum rate of travel parameter Rmax, to confirm if the cutting electrode or wire (see e.g. FIG. 1) is travelling at a rate that is consistent with a safe cutting rate and properly functioning system 100. The rate of travel variable Rtravel of the electrode is an important variable to ensure the low temperature cutting desired. With a fixed power delivery, as the rate of travel Rtravel of the electrode through the tissue is reduced, the total energy delivered to the tissue increases and the resulting temperature of the localized tissue near the electrode will increase at a faster rate. If the resulting temperature rise is too much or too fast, patient injury may occur.

The minimum rate of travel parameter Rmin may be determined experimentally by adjusting the power P, derived from the voltage V and current I applied to the active electrodes or wires, and measuring the rate of travel that achieves the maximum allowable temperature rise on the surface of a control tissue specimen. In some embodiments, the mechanical force F may be adjusted to a known mechanical force F of zero pounds-force or more. In addition to varying power and force, a vibration or other dynamic load may be applied to the wires to speed its progress upon sensing a low rate of travel.

The maximum rate of travel parameter Rmax may be determined experimentally by measuring the rate of rise with no mechanical F on the tensioning mechanism or electrode(s) or wire(s). This value indicates a condition where the wires are not applying a force to the tissue specimen, such as a broken wire.

Figure 6:
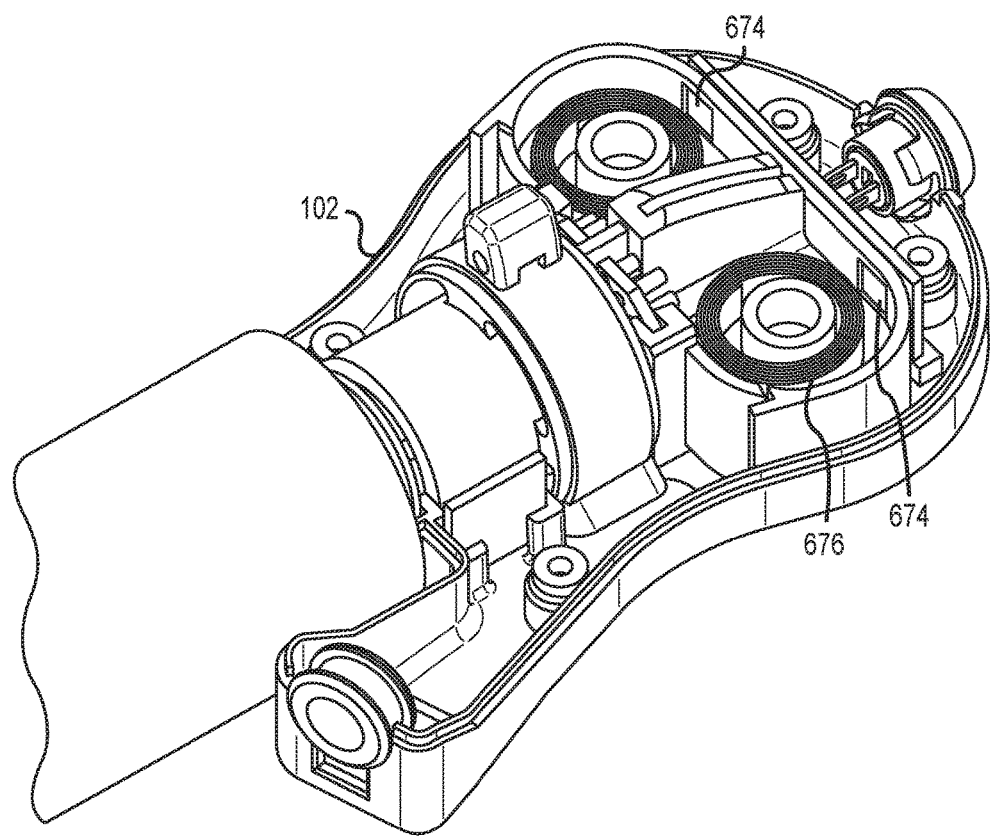
FIG. 6 illustrates a sensing device.

Many methods may be used to measure or determine the rate of travel. In some embodiments, and as is illustrated in FIG. 6, an optical motion sensor 676 is provided in near proximity to a spring or force application mechanism 674. The optical motion sensor may be focused on a location of the spring such that as the spring moves, the optical sensor area of focus could detect this motion as linear translation. In some embodiments, the motion may be detected as a motion within a plane.

In some embodiments, a plurality of motion sensors may be provided. The plurality of motion sensors may be configured to compare images at time T0 against images at time T0+1 to determine a direction and/or a distance of movement of the tensioning mechanism, cutting electrode, and/or wire.

In some embodiments, the sensor(s) have one or more integrated circuits, a sensor optical lens, and a light source. In some embodiments, the sensor(s) have separate components specifically for the application. The area of focus on the spring may be near the spool of the spring cylinder on the flat side of the spring coil so that the movement of the spring appears as a horizontal, transverse, or X direction motion. In some embodiments, the area of focus of the optical sensor is along the extended portion of the spring away from the spring spool or cylinder. In some embodiments, the area of focus is on the top of the spool cylinder such that as the spring moves, the sensor is configured to detect rotational movement that is detected as both X and Y movement or transverse and longitudinal movement.

In some embodiments, one or more optical sensors are provided and configured to detect contrast changes rather than creates images. The contrast changes can be surface irregularities in the spring or force application mechanism or can be patterns that are created on the spring surface. In some embodiments, preselected or known and regular intervals of contrasting patterns may be provided on the moving component, such as the tensioning mechanism, cutting electrode, or wire, and one or more optical sensors are configured to count the number of patterns moving past the area of focus to determine rate of travel and distance of travel. In some embodiments, the patterns are configured to provide a reference interval to measure the rate. The patterns may be separate patterns integrated or modulated into a primary pattern or near a primary pattern as a secondary pattern, so as to provide additional information, such as absolute distance traveled, beginning or end of travel markers, and/or key points of distance traveled.

In some embodiments, the device may be configured to adjust a power in response to information detected and/or communicated by the sensor or plurality of sensors. For example, the device may be configured to increase a segmentation power being applied to a cutting electrode in response to a determination that the tensioning mechanism, electrode, or wire is translating or moving at a less than preferred rate. As another example, the device may be configured to decrease a segmentation power being applied to a cutting electrode in response to a determination that the tensioning mechanism, electrode, or wire is translating or moving at a greater than preferred rate.

In some embodiments, a wheel having a known diameter may be provided in contact with the spring or force application mechanism, and a measured rotation of the wheel provides an indication of spring travel. The rotation of the wheel can be measured by including spokes in the wheel of known width or angle and optically counting the number of spokes observed by a light source and detector located on opposing sides of the wheel.

In some embodiments, the wheel is mechanically coupled to a potentiometer or variable resistor. As the wheel rotates, the resistance of the potentiometer changes; the change in resistance may be used to calculate the corresponding change in travel of the spring.

In some embodiments, a resistive film is provided on an exposed top surface of the wheel. A variable resistance along the surface may be provided, varying from a low impedance value to a high impedance value as the wheel rotates. A pair of contacts can be placed in the center and edge of the resistive film surface such that rotation varies the resistance, and the rotation can be calculated by tracking these changes in resistance.

In some embodiments, the device may be configured to detect a capacitance change to determine a rate or distance of travel. In some embodiments, an electrical plate that does not cover the entire wheel surface is provided, such as a semicircle, having a second conductive semicircle. Applying a time varying voltage between these two plates, the change in capacitance may be measured as the wheel rotates. In this approach the change in travel of the spring can be calculated in a similar manner as the previous example with a resistive film.

In some embodiments, an encoder is mechanically coupled to the spring or force application mechanism to indicate a rate or distance of travel. The encoder may provide waveforms that can be used to determine a rate of travel using the phase of the two waveforms.

In some embodiments, and output of one or more sensors or a sensing circuit provides information that is used to calculate or infer a rate of travel. The electrosurgical instrument 102, which may also be referenced herein as a segmentation instrument, may use this information directly to determine if the rate of travel is acceptable. The segmentation instrument may include a processing device, an analog circuit, and/or a digital circuit to calculate, process, and/or track a sensor output. In some embodiments, the device may initiate an action responsive to the information from the one or more sensors, such as, for example only when a distance or rate of travel is outside an acceptable or expected range.

It may be beneficial to scale this information into units that are meaningful to users such as cm/second. In some embodiments, the device has a processor configured to scale a digital, analog, or other signal into an informative output in a manner known to those skilled in the art. One benefit of using this method is that the motion of the spring can be quantified in a traceable manner that can be compared to external measurement equipment. An additional benefit is that correction algorithms can be applied if a non-linearity is observed in the rate of travel through the entire range of travel of the spring or force application mechanism.

In some embodiments, the segmentation instrument has a processing device in communication with the sensor(s). In some embodiments, the segmentation device may have a microprocessor, state machine, and/or field programmable gate array (FPGA) to perform the processing and/or allow a user to configure the segmentation device.

In some embodiments, the signals are transmitted from the segmentation instrument to a separate device, such as a controller or another processing unit on-site or off-site, to perform this processing. The distance of travel variable Dtravel may be measured directly from a tensioning device in the electrosurgical device 102, and may be used to compare against a pre-tension distance of travel parameter Dpreten and a cut complete distance of travel parameter Dcomplete. The pre-tension distance of travel and cut complete distance of travel parameters Dpreten, Dcomplete are calculated by the tensioning mechanism and active electrode assembly design such that the pre-tension distance of travel parameter Dpreten indicates the minimum distance achieved during pre-tensioning with the largest intended tissue specimen, and the cut complete distance of travel parameter Dcomplete indicates the maximum distance achieved when the active electrode wires have finished the cut. See Applicant's application PCT/US15/41407 for details of the tensioning device. The variable Dtravel may also be used to measure the travel of each separate tensioning mechanism after pre-tension is applied. These values may be used to approximate the volume and/or shape of the tissue specimen by comparing the Dtravel at the completion of pre-tension against Dpreten. By using this approximation, the maximum energy delivered to the tissue parameter Emax, may be adjusted to accommodate the tissue specimen being segmented.

Those skilled in the art will recognize that the methods and or components employed to measure the rate of travel previously described herein may be used to determine, calculate, or infer a distance traveled. In some embodiments, a distance traveled is calculated or determined as a relative distance. In some embodiments, a measured distance is calculated or determined as an absolute distance, for example, where an initial position is known or if absolute position indicators are included, such as previously described.

In some embodiments, the device may be configured to transmit a signal or information related to the segmentation to the user. For example, the segmentation device may be configured to indicate a percentage of completion of a segmentation procedure, a rate of completion, a rate of travel, an absolute distance traveled, and/or a relative distance traveled.

In some embodiments, the segmentation device may be configured to transmit an auditory or visual warning signal to the user where the rate of segmentation, rate of travel, and/or other parameters are not within an expected range, such as an expected range that would be associated with a segmentation power being applied to the electrode(s). That is, an expected range of a travel rate may be associated with a particular power level and/or segmentation force. If the actual travel rate is outside the expected range, this may be an indication of a problem with the procedure, and the user may need to halt and/or adjust the procedure.

Figure 20:
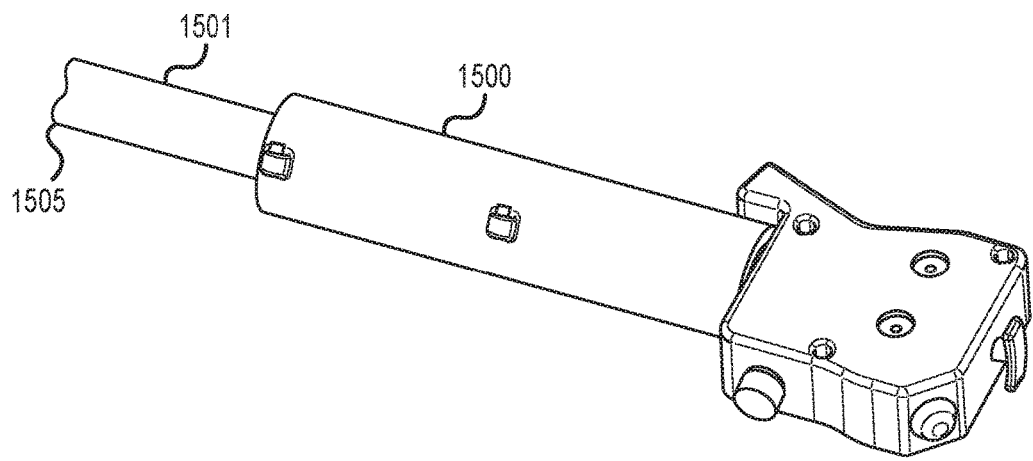
FIG. 20 is a perspective view of a removal device with an introducer.
Figure 21:
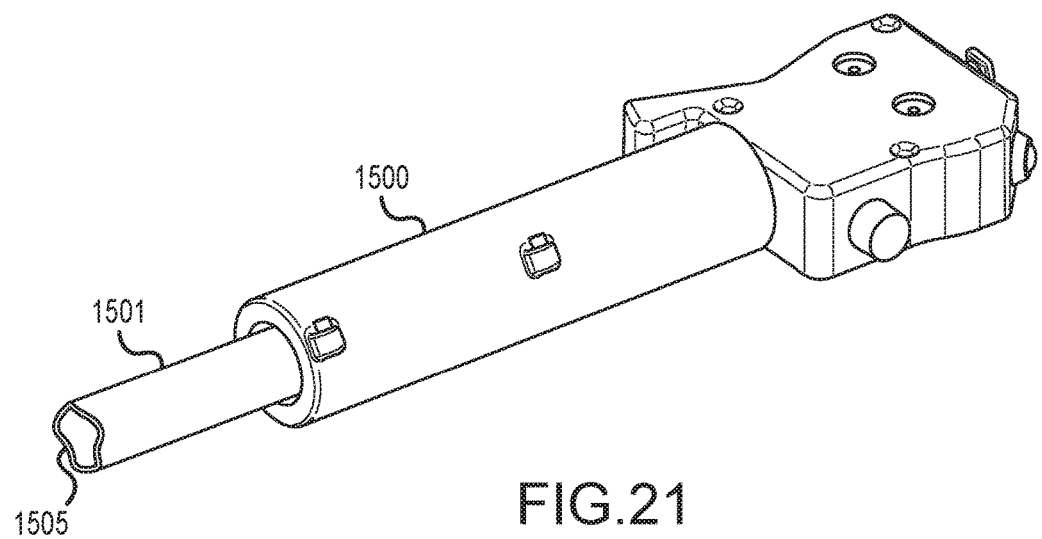
FIG. 21 is another view of the device in FIG. 20.
Figure 22:
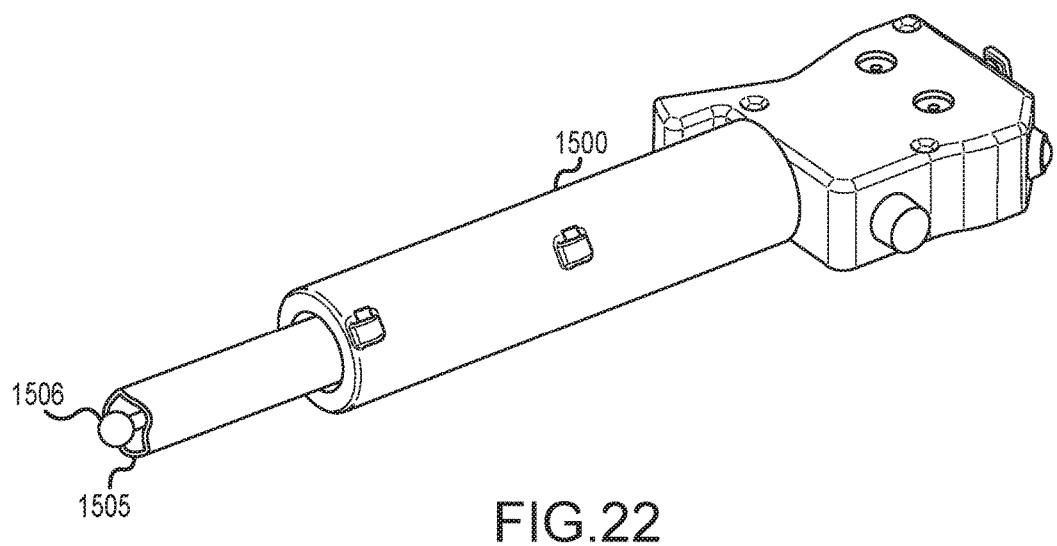
FIG. 22 is another view of the device in FIG. 20.

With brief reference now to FIGS. 20-22, the pre-tensioning of active electrode wires is now described. In some embodiments, an introducer tube mechanism 1500 may be provided to enable a user to pre-tension the wires against the tissue sample, that is, to bias the wires towards the tissue sample. Upon initiating this mechanism 1500, the introducer tube 1501 will extend in length towards the tissue sample (instead of pulling the tissue sample back towards the introducer tube). This mechanism 1500 may include a nested, spring-loaded tube which telescopes out towards the specimen upon release of the mechanism. This extending introducer tube may include, but is not limited to, a jackscrew mechanism which unscrews to extend the introducer tube, inflatable bladders which extend the multi-piece introducer tube, and/or manually extending the nested introducer tube with the aid of self-locking teeth to prevent the extended introducer tube from collapsing back on itself.

The extendable distal end portion of the segmentation instrument may be inserted into the cavity of the patient and in direct contact with the tissue to be segmented. This distal tip of the instrument tube, termed the introducer tube 1501, may have the opportunity to be a point of high frictional drag between the active segmenting wires and the tissue/introducer tube interface. Some embodiments therefore include dentals 1505 (see e.g. FIG. on a distal end of introducer tube—which allows the introducer tube to be firmly contacted with the tissue specimen, yet gives space for the segmentation wires to freely retract through the tissue and into the segmentation instrument without getting pinched between the tissue specimen and the distal tip of the introducer tube.

Some embodiments include a standoff platform 1506 to reduce friction. In some embodiments, the standoff 1506 may be a spherical standoff. Those skilled in the art will understand, however, that the platform 1506 may be in the form of any shape, as long as the platform provides intimate contact with the tissue and provides a clear space through which the active segmentation wires can travel. In some embodiments, the platform provides intimate instrument/ segmentation tissue contact while still offering an open space where the segmentation wires can more freely travel between the tissue and the distal tip of the introducer tube 1501 (on the segmentation instrument).

Figure 3:
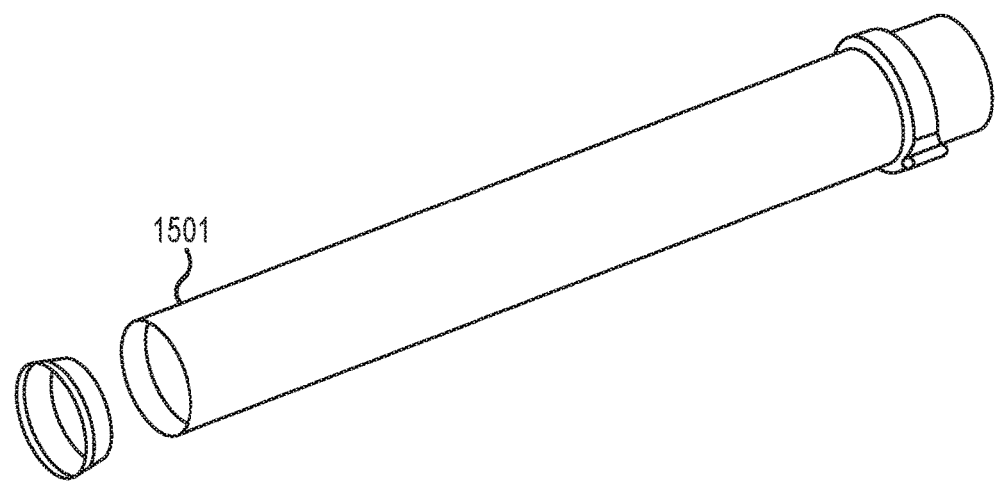
FIG. 3 illustrates a perspective view of an introducer.

In some embodiments, a distal tip of the introducer contains a lubricious and high temperature insert, such as PTFE, that reduces the friction of the wires traveling through the tube and into the instrument, as is illustrated in FIG. 3.

Figure 4:
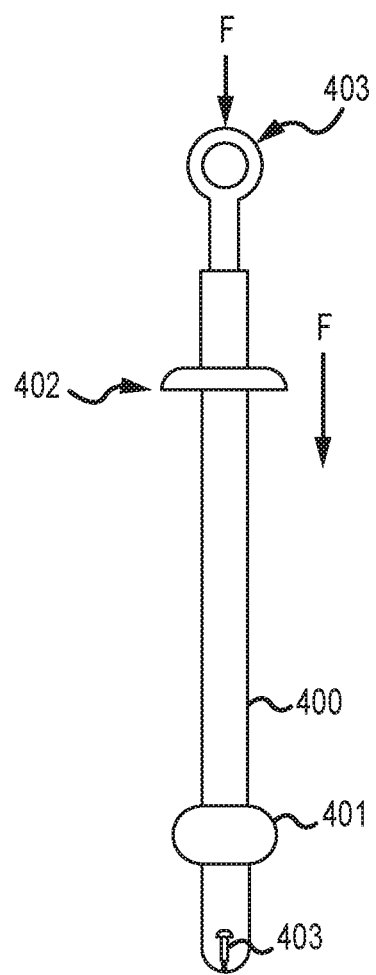
FIG. 4 illustrates an introducer.

Returning now to FIG. 4, the introducer 400 may have two or more features to maintain pneumoperitoneum. The introducer may have an inflation ring 401 around the distal portion of the device that is placed near the inside surface of the peritoneum. in some embodiments, a second mechanical sealer 402 is provided, that may be adjusted downward toward the incision in a manner that compresses the tissue between the inflatable ring 401 on the inside of the peritoneum and the mechanical sealer 402 on the outside of the peritoneum. In some embodiments, inflation may be achieved by using a separate syringe attached to the introducer when desired. In some embodiments, a syringe-like feature is incorporated into the handle of the introducer 403 such that as the proximal handle is moved it creates a pressure that is channeled to the inflatable ring.

Figure 5:
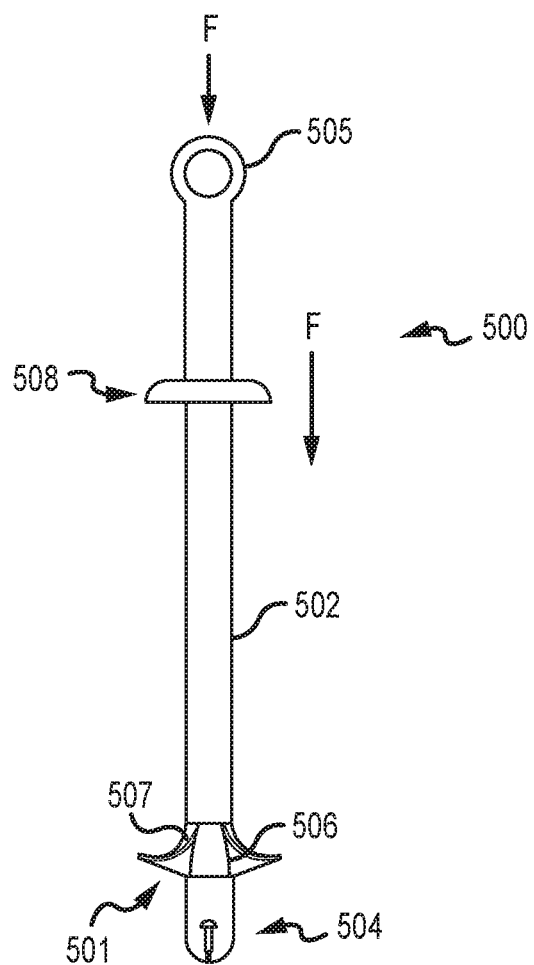
FIG. 5 illustrates an introducer.

Turning now to FIG. 5, some embodiments include a flexible membrane 501 near the distal end of the introducer 500. A proximal section of the introducer 502 may slide toward the distal end of the introducer 504 by applying a force on the handle 505, causing an interference between a ramp 506 on the distal end and semi-rigid fingers 507 coupled to the proximal section. The interference may cause the semi-rigid fingers to expand outward causing the flexible membrane 501 to expand outward away from the introducer creating a protrusion that can be used to seal the inside of the peritoneum. A mechanical sealer 508 can be applied as previously described to provide compression at the incision site.

In some embodiments, a flexible membrane is located near the distal end of the introducer. Semi-rigid "fingers" may be arranged around the circumference of the introducer shaft, under the membrane, and coupled to the proximal section of the introducer. Under the "fingers" is a ramp coupled to the distal most portion of the introducer located such that the ramp begins at the distal edge of the fingers in the normal position. When the proximal portion of the shaft is advanced toward the distal end of the introducer, the fingers are extended away from the introducer also extending the flexible membrane. This creates a protrusion that can be used to seal the inside of the peritoneum. A mechanical sealer can be applied as previously described to provide compression at the incision site.

In some embodiments, the introducer has a film attached near the distal end of the device. This film is arranged in a cross sectional axis of the introducer so that when the introducer is withdrawn to the proper location, the film may provide a seal to the incision site. In this embodiment, the introducer will be hold in place the by the user to maintain pneumoperitoneum or the use of the seal on the outside surface as previously describe can be used to help with holding the introducer in the proper location.

Those skilled in the art can understand that any combination of flexible membrane, inflation ring, or mechanical sealer can be used on the inside and/or outside surface of the incision site to provide a seal that maintains pneumoperitoneum. In addition, the distal most portion of the handle can incorporate many user interface features to enact the sealing features, including a slide that applied inflation or motion, a section of the tube that can be moved up or down along the shaft of the introducer, or a protrusion that acts and a lever to create the motion required to initiate the sealing.

In some embodiments (see e.g. FIG. 4), the coupling of the drawstring to the distal portion of the introducer 403 can be included with the sealing feature to provide multi-functionality of the introducer. This increases the efficiency of the procedure by minimizing the effort required to perform the bag insertion, sealing of the peritoneum during tissue loading and allowing easy withdrawing of the introducer while at the same time pulling the bag opening through the incision site.

In some embodiments, the generator 104 may be coupled to a first set 120 of first, second, and third leads 114, 116, 118 for detecting and/or sending analog and/or digital signals associated with tissue segmentation. For example, the analog and/or digital signals may include signals for controlling tissue segmentation variables, including, but not limited to voltage, current, impedance, power, rate of travel, distance of travel, and/or mechanical segmentation forces to be adjusted or applied during a tissue segmentation procedure. The first set 120 of leads may be associated with a first cutting wire 122 coupled to the electrosurgical device 102. A second set 130 of leads, which may likewise include first, second, and third leads, may be associated with a second cutting wire 124. The sets 120, 130 of leads may include more or fewer leads per set, and more or fewer sets.

In some embodiments, the controller 108 may be configured to cause the cutting wires 122, 124 to apply radio frequency (RF) power to a tissue specimen (not shown) for segmentation and removal. Although just two wires 122, 124 are illustrated in FIG. 2, the controller 108 may be configured to control a number of tissue segmentation variables associated with a number of wire sets.

Figure 7:
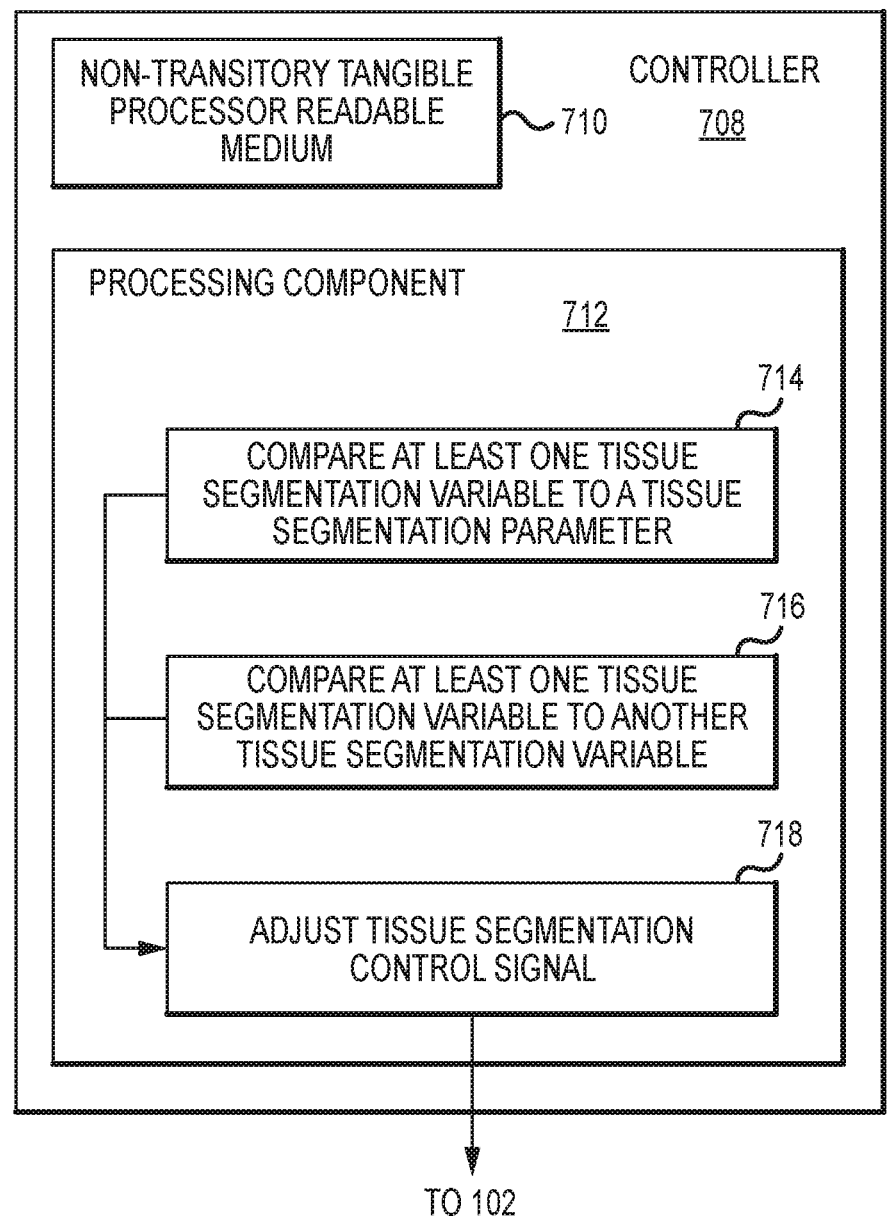
FIG. 7 is a flowchart depiction of a controller and method.

With reference now to FIG. 7, the controller 108, 708 may be configured to control a number of tissue segmentation wires in a time multiplexed manner. For example, the controller 108, 708 may include a non-transitory tangible processor-readable medium 710 including instructions to effectuate the methodologies described herein. For example, the non-transitory instructions may be accessible by a processing component 712 to execute one or more methods.

One method may include comparing 714 at least one detected tissue segmentation variable with a tissue segmentation parameter and/or comparing 716 at least one detected tissue segmentation variable with a second tissue segmentation variable, and adjusting 718 a tissue segmentation control signal in response to either comparing 714, 716.

The controller 108, 708 may be further configured to control the tissue segmentation variables so that a plurality or all of the cutting wires 122, 124 complete tissue segmentation cuts at substantially the same time. Completing the tissue segmentation cuts at substantially the same time may help manage temperature accumulation at each wire location.

The controller 108, 708 may be configured to cause substantially simultaneous cut completion by switching RF power between each of the cutting wires intended to apply the RF power. This may be achieved by switching the RF energy in a sequential algorithm for a fixed time period, switching the RF energy such that the slowest rate of travel mechanism receives the most energy, to control the cutting wires 122, 124 to have the same length of travel during the cuts or based on the electrical parameters such that those cutting wires 122, 124 indicating a different or lower impedance values or a lower length of travel during the same time span may receive more RF power on average than the remaining wire sets to maintain the cuts. Those skilled in the art will recognize that, if the electrode is not travelling, the steam pocket may collapse, resulting in a lower impedance; in contrast, if the cutting is active, the steam pocket may increase the impedance.

Particularly when using the multiplexed approach, the inactive time should be limited to maintain the steam or higher impedance around the wire to sustain cutting.

Inactive time should also be limited when a first tensioning mechanism or cutting wire 122, 124 is not advancing, or not advancing as quickly, as a second tensioning mechanism or cutting wire 122, 124, such as due to a highly calcified tissue specimen or some other means of failure (such as encountering a staple in tissue sample). In this case, the cutting wire 122, 124 or wire set that is not properly advancing may be excluded from receiving RF power. In some embodiments, the remaining cutting wires 122, 124 or wire sets can complete the cut.

Figure 8:
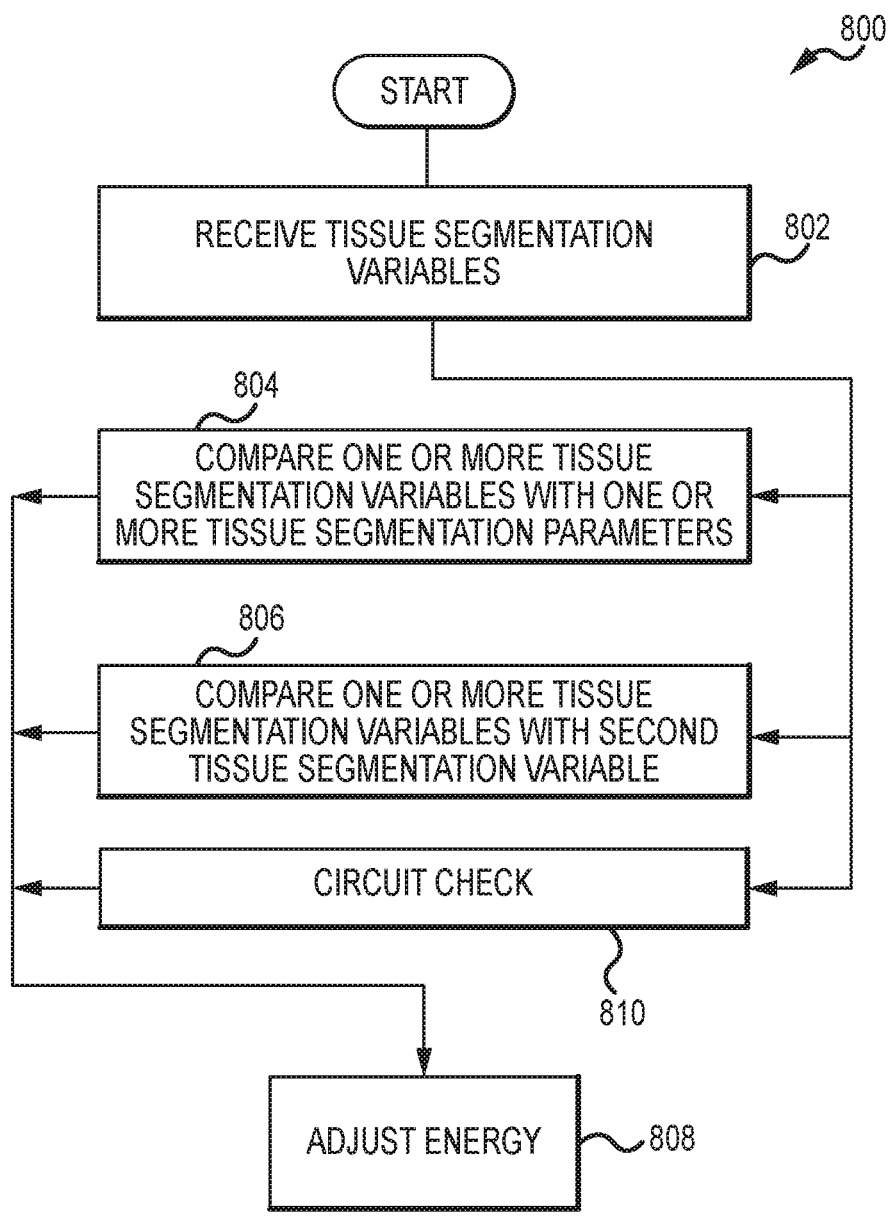
FIG. 8 is a flowchart of a method of controlling a tissue segmentation procedure.

Turning now to FIG. 8, further details of a method 800 of tissue segmentation are now described. As illustrated, the method 800 includes receiving 802 a plurality of tissue segmentation variables. The tissue segmentation variables may be associated with a tissue segmentation procedure being performed, such as segmenting a large tissue specimen prior to removal through a small incision site. The tissue segmentation variables may include variables applied to a tissue specimen by a tissue segmentation wire, such as energy, power, voltage, current, mechanical force, and/or feedback variables such as impedance, resistance, rate of travel and distance traveled.

Receiving 802 may include receiving the plurality of tissue segmentation variables over time.

The method 800 also includes comparing 804 one or more of the tissue segmentation variables with a respective tissue segmentation parameter, or comparing 806 one or more of the tissue segmentation variables with a second tissue segmentation variable, and, responsive to the comparing 804 or comparing 806, adjusting 808 an energy and/or segmentation force to a tissue specimen.

The method 800 may be achieved using the device illustrated in any of FIGS. 1-3 or otherwise described herein.

The method 800 may include comparing a detected power factor angle PFAcut variable with a short circuit power factor angle parameter PFAshort and/or an open circuit power factor angle parameter PFAopen. The power factor angle parameters PFAshort, PFAopen are described in preceding sections of this disclosure.

Returning now to FIG. 1, the system 100 and/or method 800 may optionally include a circuit check 810 having a short circuit and/or open circuit check. That is, in some embodiments, the system 100, controller 108, 708, and/or generator 104 may be configured to send a short, small pulse of electricity at a power well below the full or operating power level to check 810 for an electrical short or open without damaging the segmentation wire/bag assembly. The power during the circuit check 810 may be at a level of 10 Watts or less, so that an electrosurgical effect does not occur.

For example, in the system 100, current and voltage sensors may be provided to give a separate real and imaginary component of the complex load impedance applied by the system 100 to the tissue. Those skilled in the art will understand that imaginary, or reactive, components of cable impedance may make measurement accuracy by a generator of a short circuit very difficult. However, by providing a system 100 or method 800 in which the real and imaginary components of the complex impedance are known, the real component may be used to provide a better measurement for shorts, opens and intermediate impedance values. In some embodiments, the system 100 or method 800 may include a short circuit and open circuit check and/or a mechanism for a short circuit and/or open circuit check.

The phase and amplitude of the complex load impedance may also be used as relative comparisons as with a short circuit, the cable inductance will be a significant contribution to the load resulting in a positive phase angle and at an open circuit the cable and system capacitance will be a significant contribution to the load resulting in a negative phase angle. Methods to calculate the phase include using an analog phase detector, comparing zero cross-over points and peak amplitudes, or using digital sampling and software methods such as a Goertzel algorithm.

In some embodiments, the system 100 may be configured such that the power or RF energy delivered to the tissue can be adjusted during the cut to provide controlled outcomes. For example, power variables applied to the wire(s) 122, 124 may be monitored and adjusted as desired, using the first and/or second sets 120, 130 of leads, or any suitable number of leads for monitoring and adjusting power to the wire(s) 122, 124, and any number of cutting wires 122, 124 may also be provided.

Those skilled in the art will understand that the leads 120, 130 may be configured to transmit digital and/or analog signals associated with the power variables or control signals. The RF power may be amplitude modulated to control the cut rate of travel. Using the rate of travel feedback, the power may be adjusted to maintain a substantially constant desired rate of travel, to maintain the rate of travel above a minimum value, Rmin, to ensure low temperature cutting, and/or to maintain the power below a maximum value to reduce the power delivered at the completion of the cut.

In some embodiments, a force gauge may be coupled to the tensioning mechanism, and the power may be adjusted to assist the spring in maintaining a substantially constant force and/or a force above or below a desired threshold for suitable tissue segmentation. These methods may be used for other means of applying the tissue segmentation force, such as a linear actuator or manual pull.

In some embodiments, the controller 108, 708 may be a box that is set on the generator 104 and has a separate power cord, or, in some embodiments, the controller 108, 708 may be unitary with, and a component of, the generator 104, as illustrated in FIG. 1 or 2, or may be unitary with, or a component of, the electrosurgical instrument 102. The controller 108, 708 may have only the power such as RF power connections attached to the generator 104 or may have an additional connection to communicate with a generator 104, a datastore 110, the electrosurgical instrument 102, and/or a user interface 112, as illustrated in FIG. 2. This additional communication allows information to be transferred to and from the generator 104. This information may include power and mode settings, return electrode impedance information, error information such as deviation from tissue segmentation parameters as previously described herein, storage and statistical information of the procedure parameters and variables, and historical statistical information of the procedural parameter database.

The controller 108, 708 may also be embodied as a battery powered device making it more portable and easier to use by reducing the need to duplicate AC power connections to perform the electrosurgical procedure.

The controller 108, 708 and/or generator 104 employing the controller 108, 708 may have the ability to measure the current I, voltage V, and/or other variables associated with the power delivered by the generator 104 prior to connecting the generator 104 output to the electrosurgical device 102. This allows the controller 108, 708 to ensure that the user has selected the proper generator setting before applying electrosurgical RF energy to the wire(s)/electrode(s) 122, 124, to ensure that the integrity of any coating on the wire(s)/electrode(s) 122, 124 is maintained for initiation.

In some embodiments, an internal resistor or resistors, selected to ensure that the proper voltage, current and power range Vmin, Vmax, Imin, Imax, Pmin, Pmax are being delivered by the generator 104, may be provided to ensure that the integrity of any coating on the wire(s)/electrode(s) 122, 124 is maintained. In some embodiments, the controller 108, 708 or system 100 is configured to alert the user, to recommend corrective action, and/or to initiate a communication with the generator 108, 708 to change a power setting in response to a determination that the integrity of a coating is compromised.

In some embodiments, the controller 108, 708 may have a means to apply power such as RF energy to individual tensioning mechanisms and wire sets in the electrosurgical device 102 so that the controller 108, 708 may selectively and/or sequentially energize the wires 122, 124.

In some embodiments, the user may select the proper sequence through a user interface 112 with the generator 104 or controller 108, as is illustrated in FIG. 2, although those skilled in the art will recognize that the user interface 112 may be located on or a component of the electrosurgical device 102 and/or any other component of the system 100. That is, the user interface 112 may include one or more means for inputting, receiving, viewing, and/or manipulating how the device 102 handles the tissue.

In some embodiments, the controller 108 may be configured to determine a crest factor of the generator output, and to confirm the user has selected the proper output mode setting. In some embodiments, measuring the RMS or average voltage (current, power) and the peak voltage (current, power) are employed to deduce the crest factor.

Figure 9A:
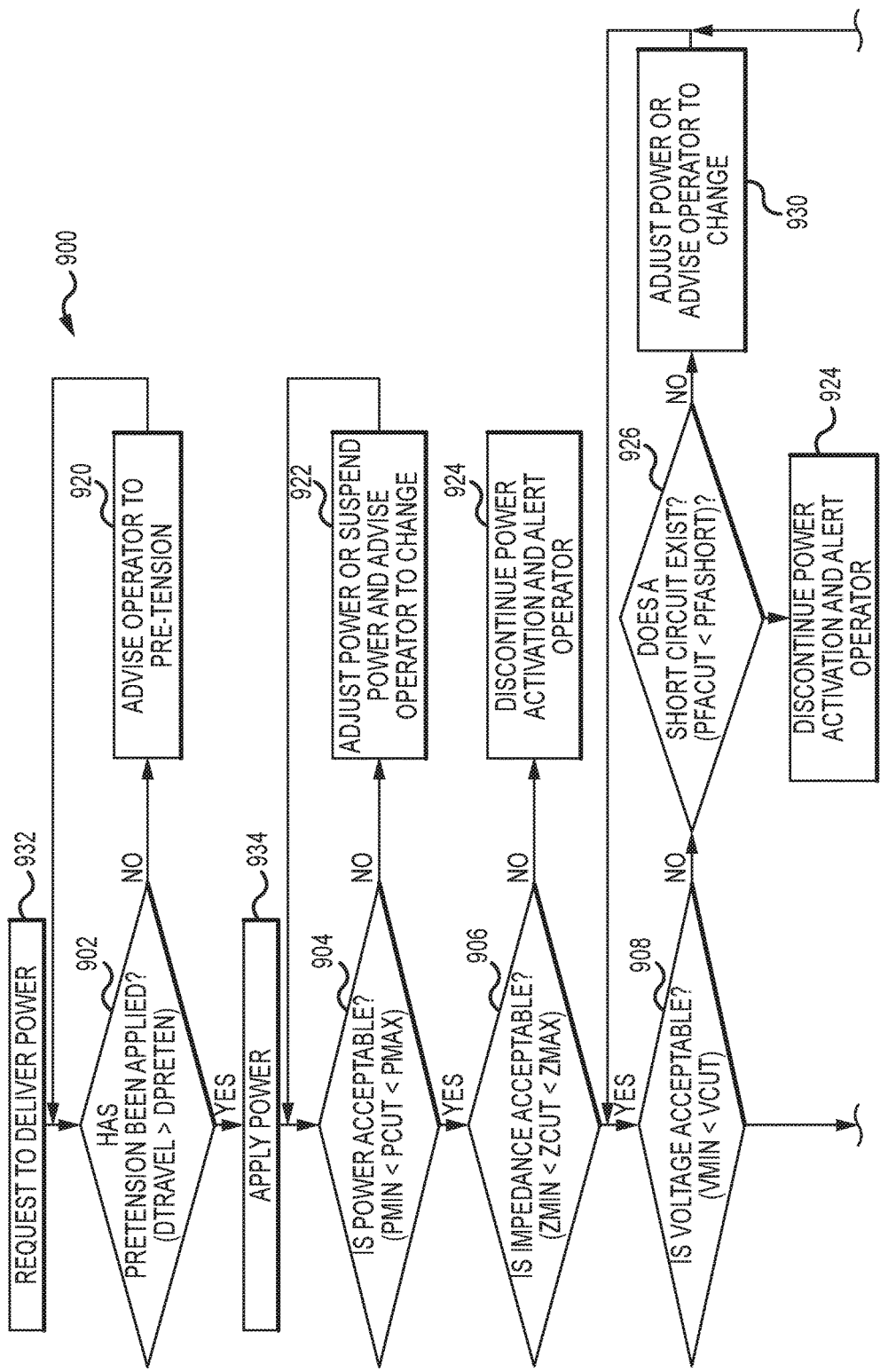
FIG. 9A is a first portion of a flowchart of a tissue segmentation control method.
Figure 9B:
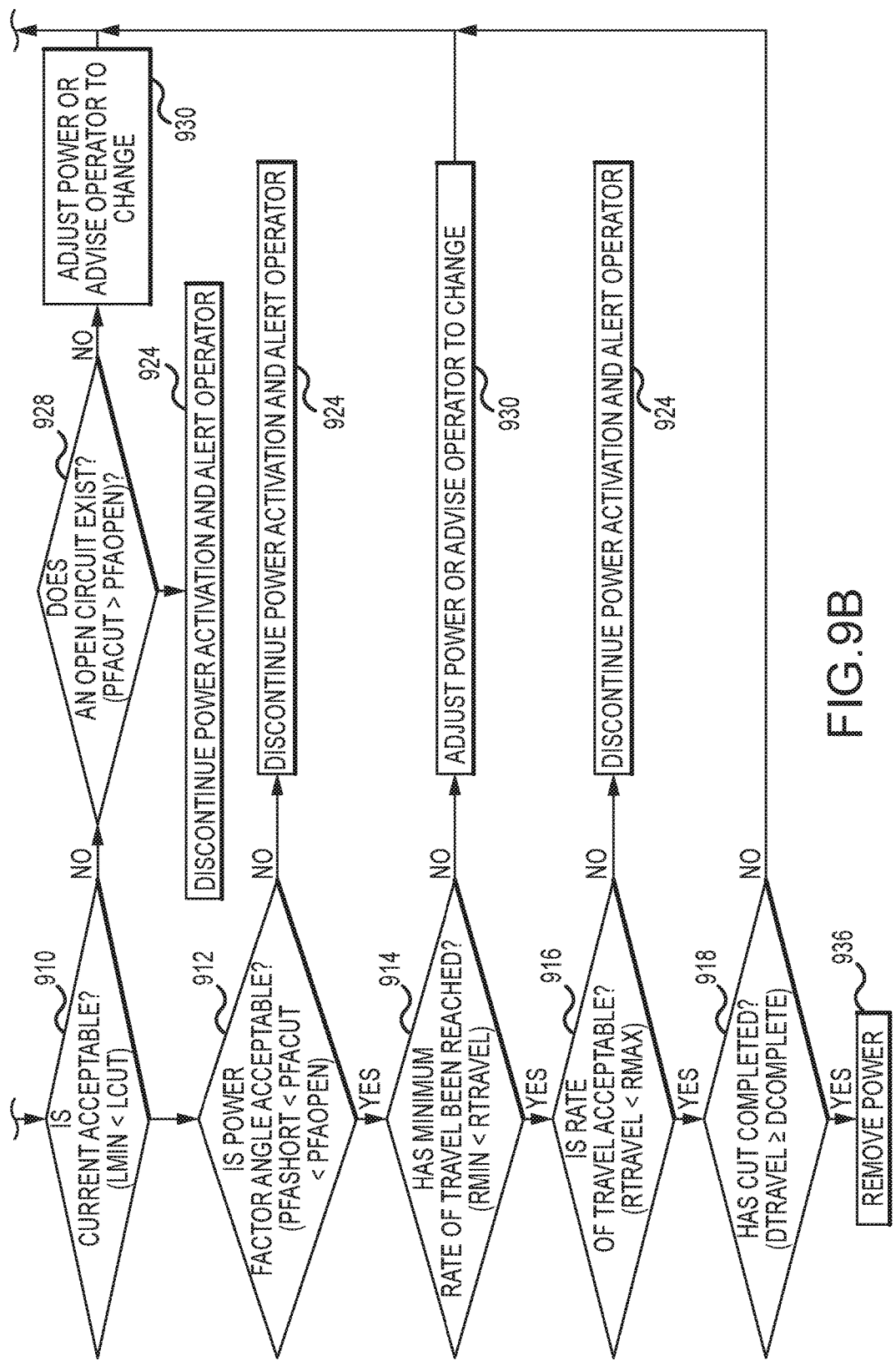
FIG. 9B is a continuation of the flowchart in FIG. 9A.

FIGS. 9A-B illustrate first and second portions of a flowchart of a method 900 of tissue segmentation control. The method 900 may be achieved using the controller 108, 708 or system 100 previously described herein. In some embodiments, the method 900 includes one or more of (a) determining 902 if a pretension force has been applied to tissue, (b) determining 904 if a power applied to the tissue is acceptable, (c) determining 906 if an impedance between a wire 122, 124 and the tissue is acceptable, (d) determining 908 if a voltage applied to the tissue is acceptable, (e) determining 3010 if a current applied to the tissue is acceptable, (f) determining 912 if a power factor angle is acceptable, (g) determining 914 if a minimum rate of travel has been reached, (h) determining 916 if the rate of travel is acceptable, and/or (i) determining 918 if a cut has been completed.

Responsive to one or more of determining 902, 904, 906, 908, 910, 912, 914, 916, 918, the method 900 may include one or more of (a) advising 920 the operator to pre-tension the device 102, (b) adjusting power or suspending power and advising operator to change the power 922, (c) discontinuing 924 power activation and alerting operator, (d) determining 926 if a short circuit exists, (e) determining 928 if an open circuit exists, or (f) adjusting power or advising operator to change the power 930.

The method 900 may include, responsive to determining 926 that a short circuit exists, discontinuing 924 power activation and alerting the operator or adjusting power or advising operator to change the power 930.

The method 900 may include, responsive to determining 928 that an open circuit exists, discontinuing power activation and alerting the operator 924 or adjusting the power or advising the operator to change the power 930.

The method 900 may include requesting 932 to deliver power, applying 934 power, and removing 3036 power. Applying 934 power may be responsive to determining 902 that pretension has been applied. Removing 936 power may be responsive to determining 918 that the cut has been completed.

Figure 10A:
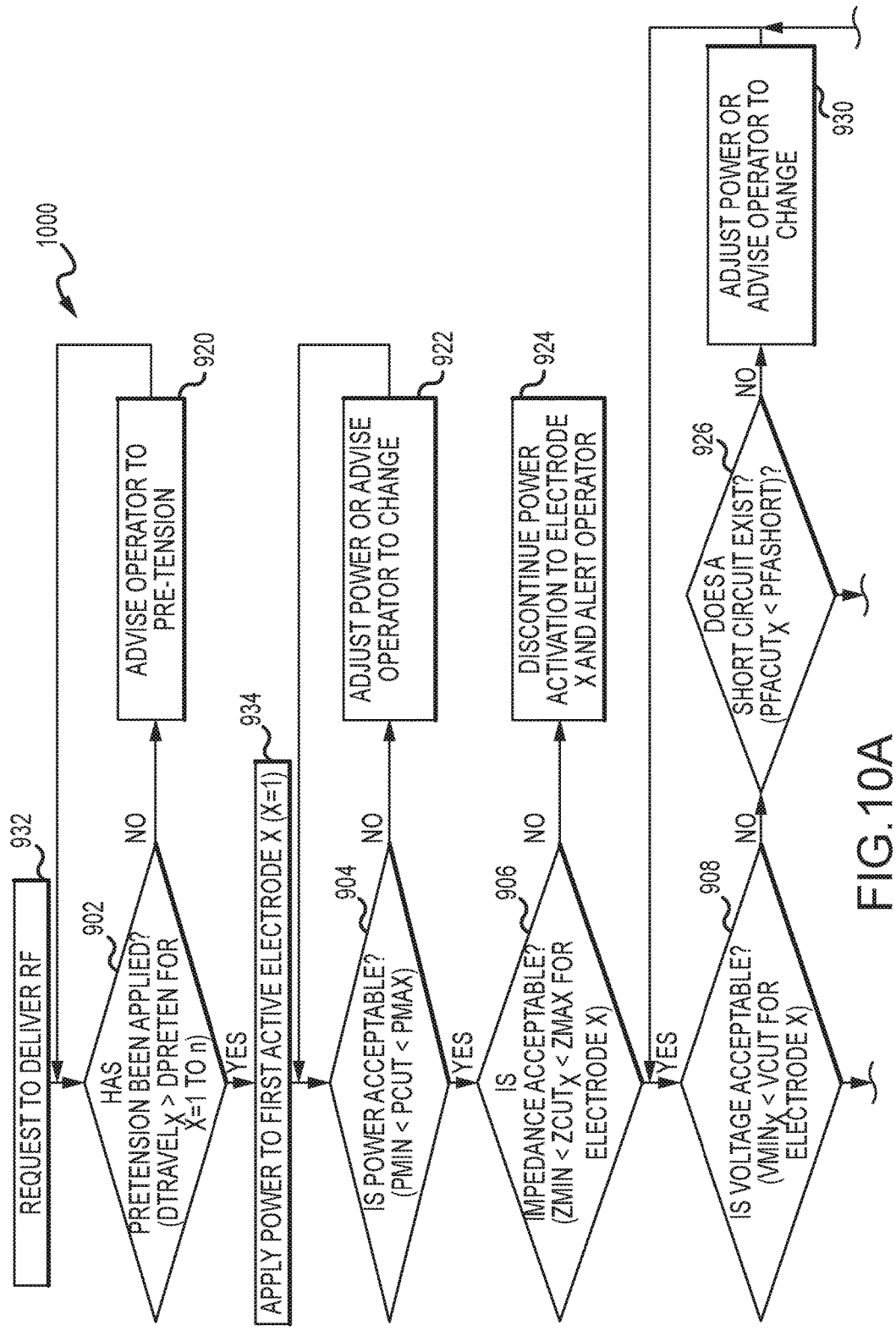
FIG. 10A is a first portion of a flowchart of a multiplexed tissue segmentation control method.
Figure 10B:
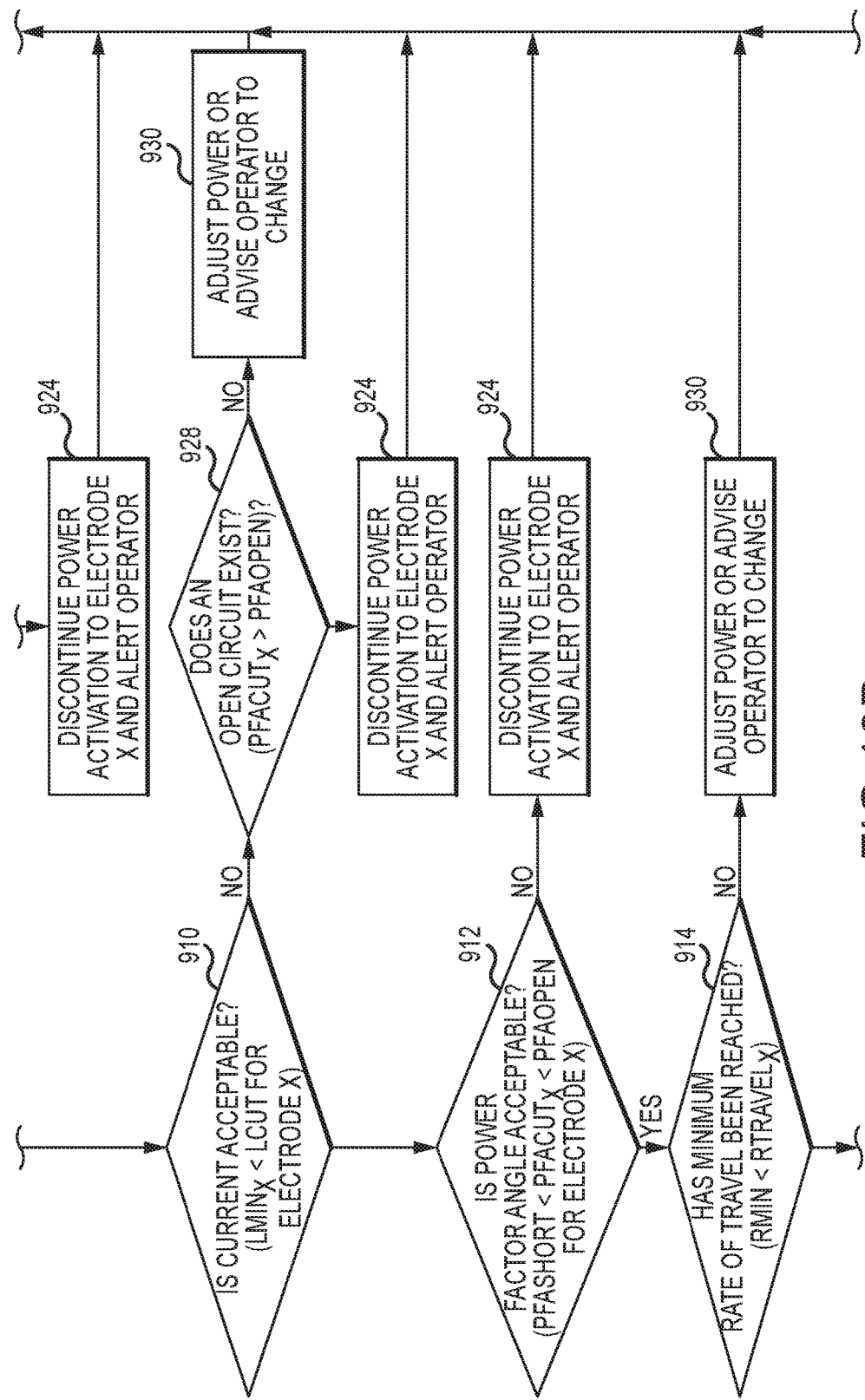
FIG. 10B is a continuation of the flowchart in FIG. 10A.
Figure 10C:
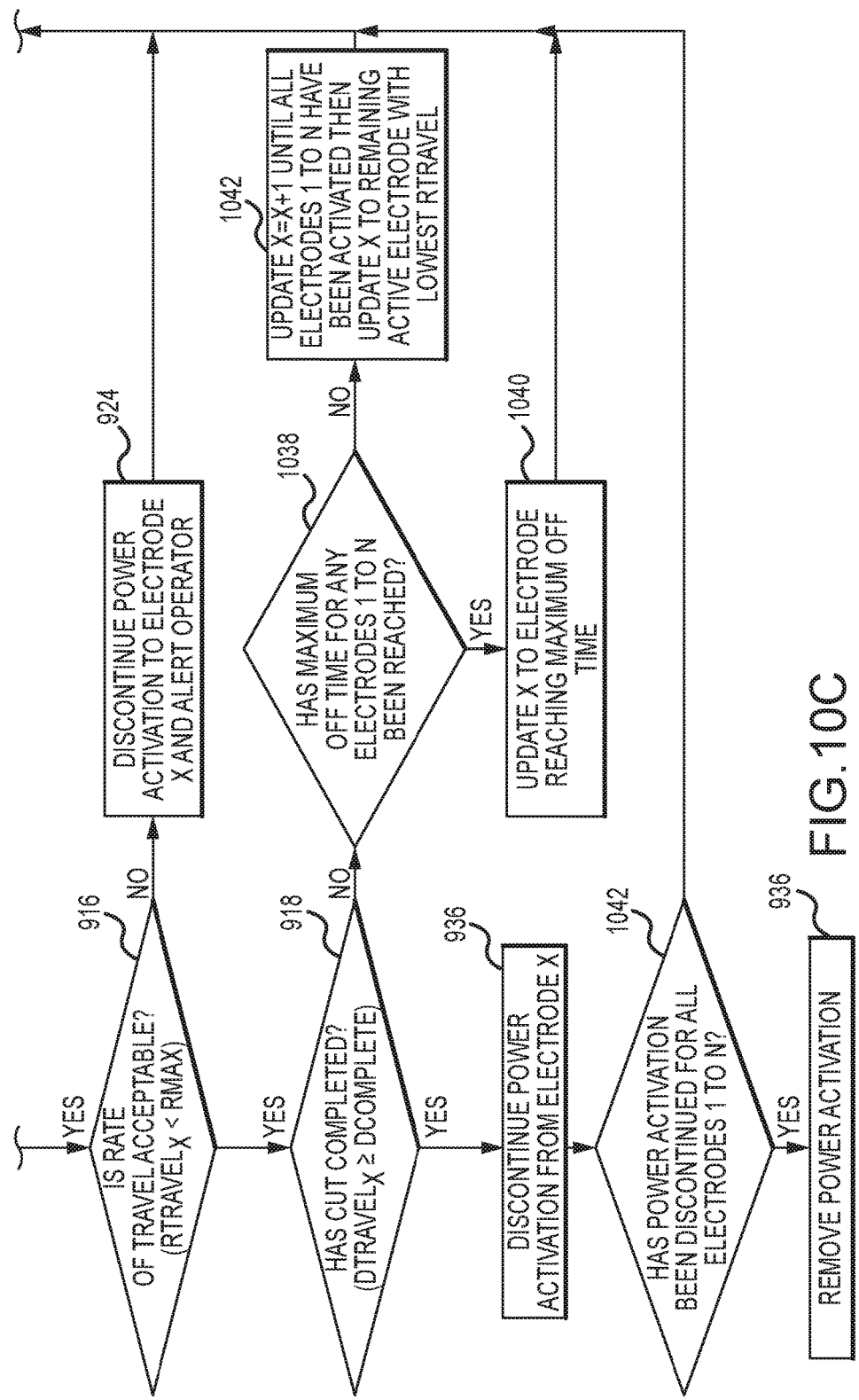
FIG. 10C is a continuation of the flowchart in FIG. 10B.

FIGS. 10A-C illustrate, together, a flowchart of a method 1000 of multiplexed tissue segmentation control. The method 1000 may be achieved using the controller 108, 708 or system 100 previously described herein, and may include some or all of method 900 previously described herein applied to each electrode X of a plurality of electrodes 1-N. The method 1000 may additionally include determining 1038 if a maximum off time for any of electrodes 1-N has been reached, and, responsive to the determining 1038, updating 1040 X to electrode reaching maximum off time or updating 1042 X=X+1 until all electrodes 1-N have been activated, then updating X to remaining active electrode with lowest Rtravel, and/or determining 1042 if power activation has been discontinued for all electrodes 1-N. In other words, the system 100, 200 may be configured such that, if one of the electrodes has reached a max off time, then the system will use that electrode next. If no electrodes have reached the max off time, then the system will apply power to the electrode that is moving the slowest.

Figure 11:
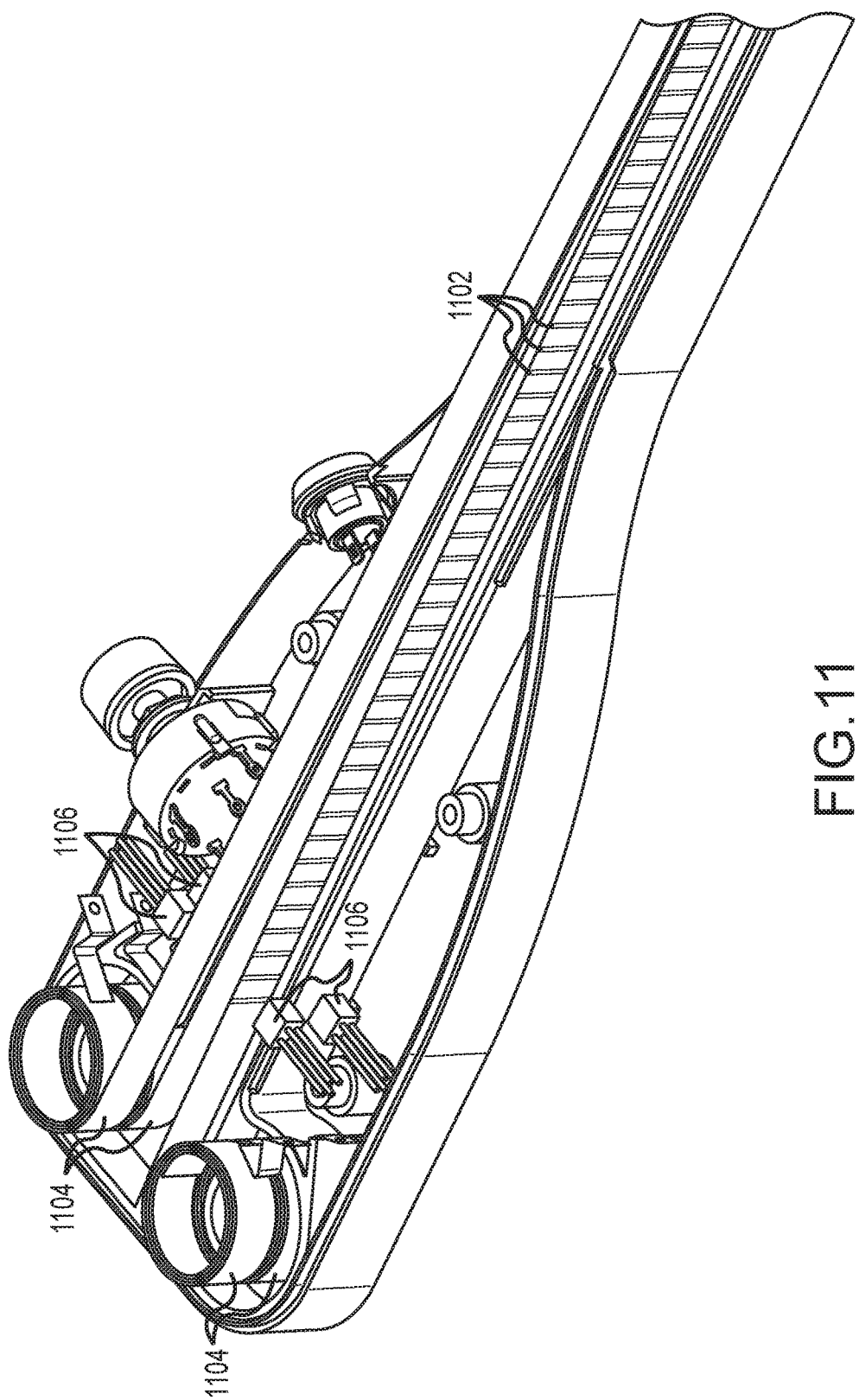
FIG. 11 illustrates an electrosurgical device and system for detecting a distance of electrode travel.

Turning now to FIG. 11, in some embodiments, various methods and systems for detecting a distance and velocity of travel of one or more wire electrodes 122, 124, such as electrodes 1-N related to methods 3000, 4000, are herein disclosed. In some embodiments, for example, a plurality of visual or electrical markers 1102 on one or more constant force springs 1104 may be provided. The markers 1102 may include lines (colored, or electrically isolated) placed at uniform distances along each spring 1104, and, relatedly, optical or electrical sensor(s) 1106 may be provided to detect or count each time a spring mark 1102 is encountered, and thereby infer the distance traveled DTravelX and/or rate of travel RTravelX. These marks may also include a larger width that is periodically included at a different uniform distance than previously described to act as a major graduation mark. This major graduation mark may be used as a gross distance measure and/or may be used for count correction, such as if the rate of travel RTravelX approaches the upper limit of the ability of the device 102 or system 100 to measure the rate of travel RTravelX. In some embodiments, the spring marks 1102 are color coded or otherwise modified verses a distance along the spring 1104, such that a color photosensor or other identifying means may determine a position of the cutting wire assembly ore wires 122, 124.

Figure 12:
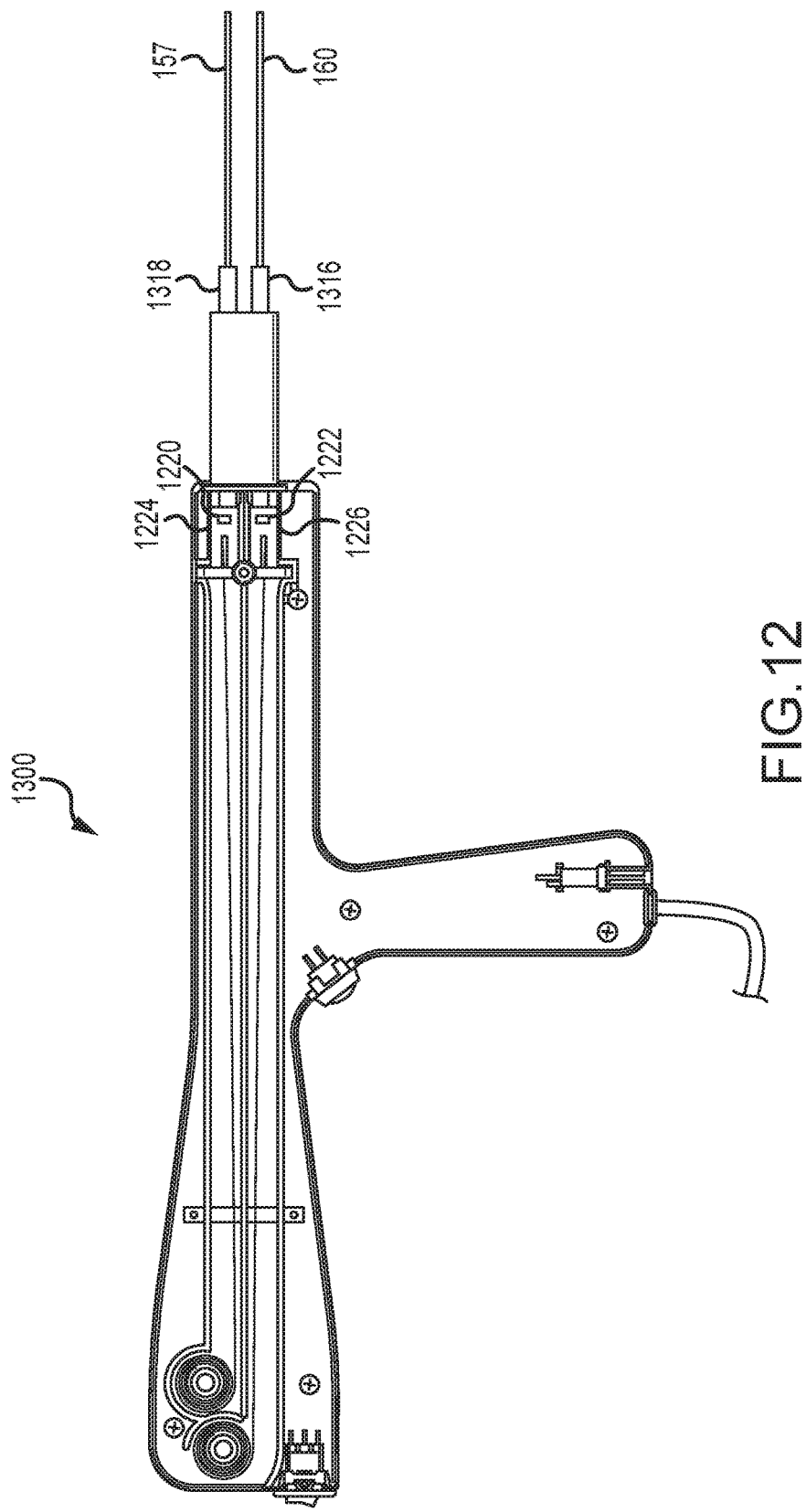
FIG. 12 is a side section view of a tissue segmentation device.

Similarly, in some embodiments, and as illustrated in FIG. 12, a first RFID tag 1220 may be mounted to a first connector block 1224 such that a single sensor (not illustrated) in segmentation instrument 102, or controller 108, 708 or generator 104 may determine a position of a first cutting assembly 151 having a plurality of wires or electrodes 153, 155 (see e.g. FIG. 1) during instrument operation. A second RFID tag 1222 may similarly be mounted to a second connector block 1226 for determining a position of a second cutting assembly 160 having a plurality of wires or electrodes 157, 159 (see e.g. FIG. 1).

In some embodiments, a force gauge or wheatstone bridge-like device may be provided to measure a deflection of a touch probe to test deflection at the spring coil. Those skilled in the art will understand that greater deflection means more spring material is deflected, and in turn meaning further travel of the electrode or wire or sets 153, 160 of electrodes or wires.

In some embodiments, a bearing mount for each constant force spring 1904 may be provided. A measurement of the rotation of each bearing mount may be used to determine travel distance (and rate) of each spring and electrode or wire.

In some embodiments, a micro 'radar' optical measurement of each connector block along the axis of the connector block travel may be provided, to visually measure how far away each connector block is from the measuring sensor—thereby determining the travel distance (and rate) of each spring and electrode or wire.

In some embodiments, a resistive strip or set of strips or films may be applied in close proximity and along the travel of the tensioning mechanism. A contact may be attached to the tensioning mechanism or tensioning block near the distal end such that it is provided electrical coupling to the resistive strip or film. As the tensioning mechanism moves, the contact acts in a similar manner as a "wiper" on a variable resistor. By using an electrical circuit that applies a voltage cross the end of to the resistive film and the contact, a change in resistance can be measured that is related to the distance of travel. The rate of resistance change can also be measured and is related to the rate of travel.

In some embodiments, the contact and resistive strip as previously described are provided, but with a second conductive strip that is in parallel but not electrically coupled to the resistive strip. The contact provides an electrical coupling to both the resistive strip and the conductive strip. In some embodiments, the electrical circuit may apply the voltage across the fixed ends of the resistive and conductive strips. Those skilled in the art will understand that this approach may be modified to utilize a contact that is not directly connected to the strip but would operate in near proximity for the duration of travel. This approach allows an electrode to apply a variable capacitance or mutual inductance that could be used to measure the distance of travel or rate of change.

The mechanical segmentation force variable Fseg may be measured by a force gauge on the tensioning mechanism. The force gauge may be any gauge suitable for the intended purpose, including any analog, digital, or mechanical signaling mechanism. The mechanical segmentation force variable Fseg may be compared to a minimum mechanical segmentation force parameter Fmin to ensure that the correct mechanical load is being applied to the tissue specimen. The minimum mechanical segmentation force parameter Fmin may defined by the design specification of the tensioning mechanism force characteristics. In some embodiments, the minimum mechanical segmentation force parameter Fmin may be defined experimentally by measuring a force associated with a desired rate of travel of the electrode(s) at a known power level in a control tissue.

Figure 13:
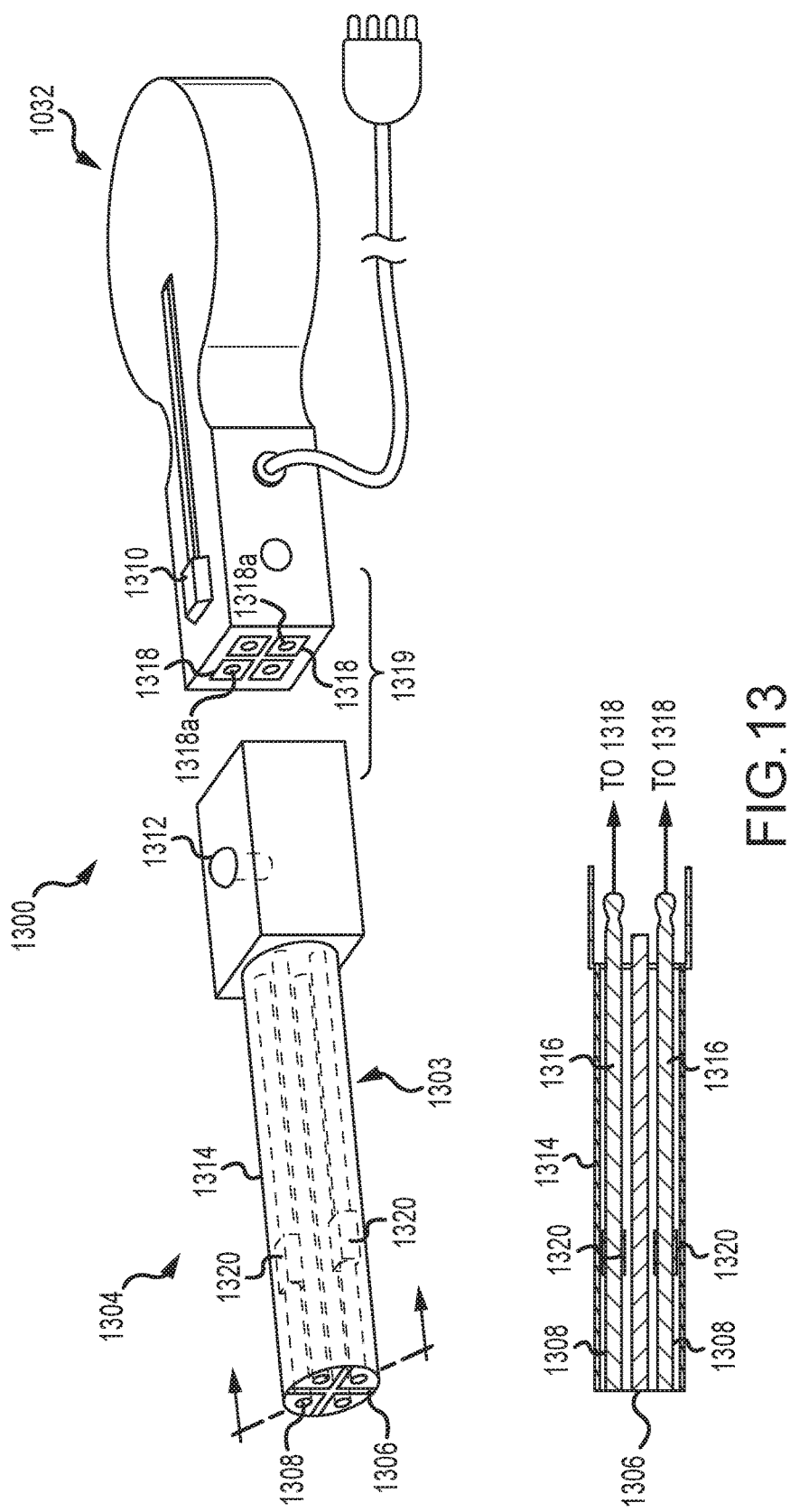
FIG. 13 is a perspective view of a disposable lumen assembly.
Figure 14:
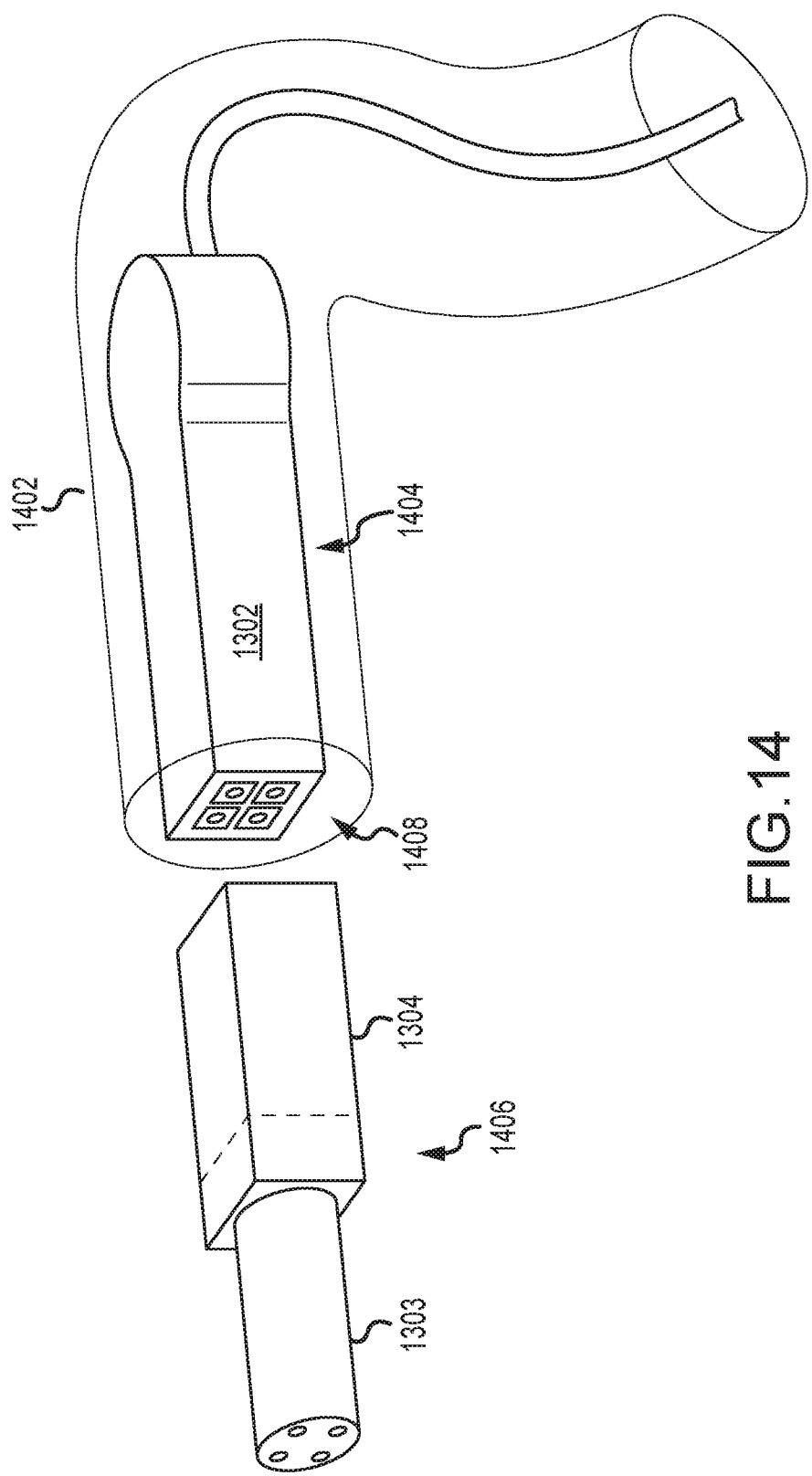
FIG. 14 illustrates a device having disposable and reusable portions.
Figure 15:
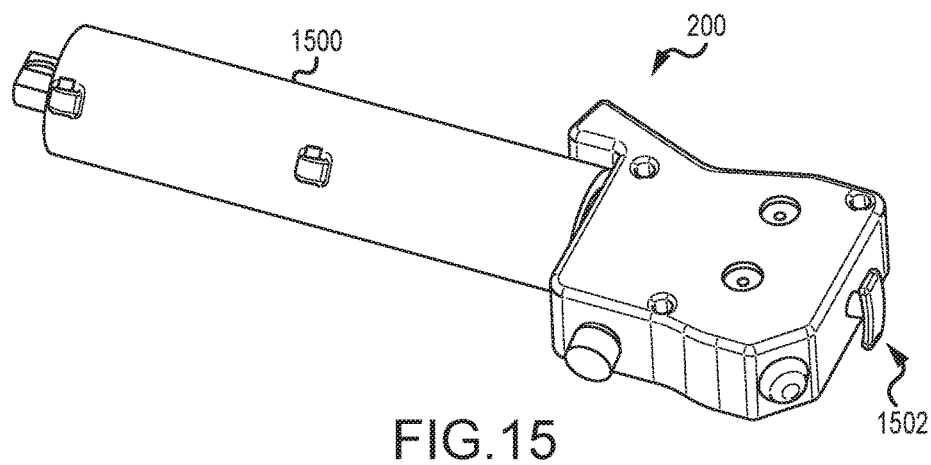
FIG. 15 is a perspective view of a removal device.
Figure 16:
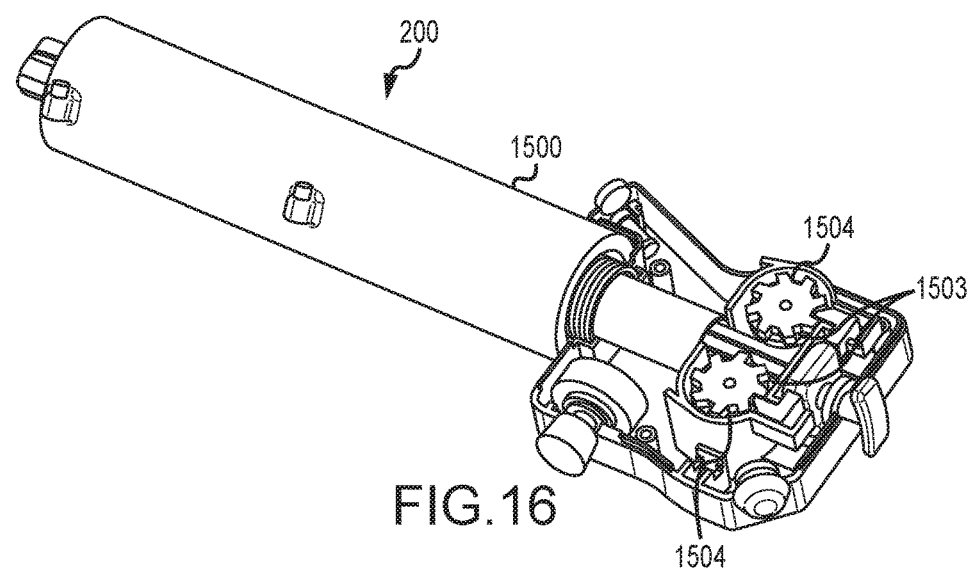
FIG. 16 is a perspective view of the device in FIG. 15 with some components removed.
Figure 17:
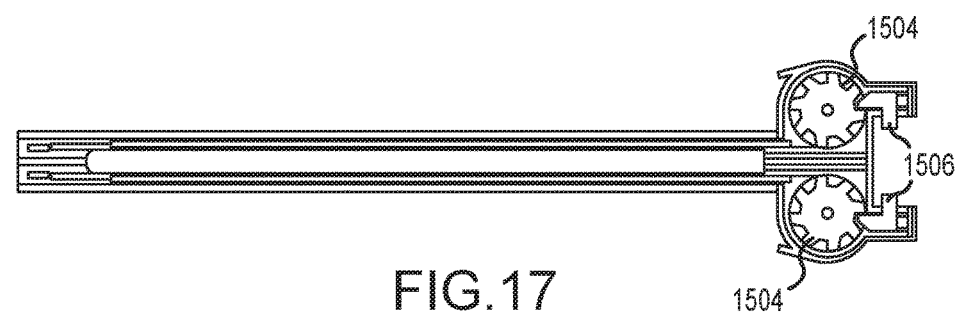
FIG. 17 is a top view of some components of the device in FIG. 15.
Figure 18:
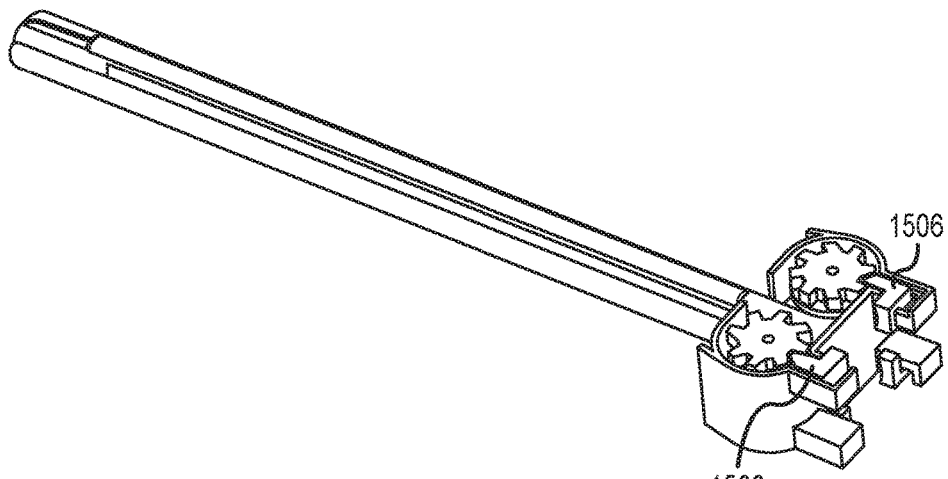
FIG. 18 is a perspective view of some components of the device in FIG. 15.
Figure 19:
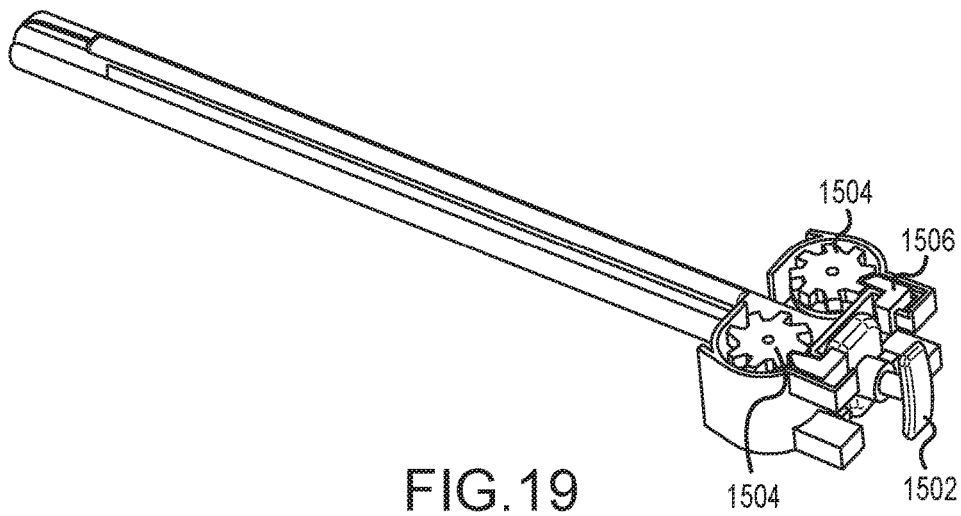
FIG. 19 is a perspective view of some components of the device in FIG. 15.

Continuing now with FIGS. 12-14, a reusable tissue segmentation device 1300 may be provided. The reusable tissue segmentation device 1300 may be configured to perform some or all of the functions previously described herein with reference to device 102 or system 100 previously described herein and the device described in Applicant's application PCT/US15/41407.

The device 1300 may include a proximal portion 1302 that is detachably connected or connectable to a distal portion 1304. A connection region 1319 between the proximal portion 1302 and the distal portion 1304 may be a block of a wire tensioning mechanism, such that a disposable lumen 1303 is attached. The disposable lumen 1303 may provide a guide 1306 for one or more tensioning mechanisms having a post 1316 that connects to tensioning blocks 1318 on the proximal portion 1302, and may have connection points to enable the distal end 1308 to connect to the active electrode wire connections (not illustrated). The disposable lumen 1303 may also include a means 1310 to advance tensioning springs (or tensioning force mechanism) to a pre-tension position, a pre-tension mechanism 1312 that allows the user to pre-tension the tensioning mechanisms and an introducer 1314 for placement in the incision site and a bag (see e.g. FIG. 1).

With continued reference to FIGS. 13 and 14, a method of using the disposable lumen 1303 is now described in further detail. In some embodiments, a control 1310 may be provided to allow the springs and the tensioning blocks 1318 of a proximal portion 1302 to be advanced to a distal position. The control 1310 may be a control tab. The springs and tensioning blocks 1318 may be held in a distal position by a locking mechanism (not illustrated) within the proximal portion 1302.

The user may connect the distal portion 1304 to the proximal portion 1302 by sliding the portions 1304, 1302 together such that the post(s) 1316 (see FIG. 13) in the distal portion 1304 snaps/slides/locks into receiving openings 1318a of the terminal blocks 1318 at the end of the tensioning mechanisms in proximal portion 1302. This attachment may also cause the control 1310 or control tab to slide proximally, or back away from the distal portion 1304 and allow alignment of the pre-tension mechanism control 1312 with the locking mechanism in the proximal portion 1302. The proximal and distal portions 1302, 1304 may be configured such that pressing the pre-tension mechanism control 1312 after attachment will release the locking mechanism and pre-tension the four tensioning mechanisms. Those skilled in the art will appreciate that a number of different release methods may be provided.

Continuing with FIGS. 13 and 14, in some embodiments, the tensioning mechanisms 1306 may be connected to active electrode connectors (not illustrated) prior to pre-tensioning, and may be contained within the guides 1306 during pre-tensioning and cutting.

The applied force generated by the tensioning mechanism in the proximal portion 1302 may be mechanically and electrically coupled from tensioning blocks 1318 through the posts 1316, through the alignment blocks 1320, through the distal end 1308 and through the active electrode connectors. In some embodiments, all patient contact areas may be part of a disposable lumen 1303, which may provide for simplified cleaning and reprocessing of the reusable portion including the proximal portion 1302.

In some embodiments, and as illustrated in FIG. 14, a reusable portion 1404 or reusable portions of the segmentation device may be enclosed by or carried within a sterile bag(s) 1402 with an aseptic transfer process. The sterile bag(s) 1402 may enclose the reusable portion(s) 1404, and a disposable portion 1406 may be attached to the reusable portion(s) by the user. Access through the bag may be made through an access opening 1408 in the bag 1402. In some embodiments, the access opening 1408 is open or opened behind a sleeve that can be moved, translated or folded away, and/or punctured by a feature of the disposable portion when the user connects the disposable and reusable portions. In some embodiments, a sterile adapter is integrated into the sterile bag(s) 1402 to facilitate connection of the sterile disposable portion(s) of the device and the non-sterile reusable portion(s), while retaining sterility in the sterile field. Those skilled in the art will readily recognize a number of means of providing a reusable portion(s) 1402 and a disposable portion(s) 1404 and enabling connection of the portions. Any and all means now known or as yet to be developed are contemplated herein.

Some embodiments providing means for separating the reusable components from the patient contact components may include a disposable insert inside the reusable tissue segmentation device 1300. The disposable insert may capture the wires after the cut. In some embodiments, a device that can be easily disassembled so that the interior area that contains the wires after the cut can be cleaned, reassembled and re-sterilized.

Turning now to FIGS. 15-22, in some embodiments, a tissue segmentation device 200 may provide multi-wire tissue segmentation in a manner that provides a user with the ability to tension only the wire set(s) to be activated with a power, such as radio frequency (RF) energy. This ability may be helpful in isolating the entire power or RF energy application to only those wires currently involved in tissue segmentation. Specifically, those performing tissue segmentation procedures may find it helpful to have the ability to tension only wires in one planar direction, for example, all "X" direction wires for the activation of those wires, or wire sets, with the introduction of power or RF energy. These "X" direction wires may be configured to not overlap each other in physical space so as to reduce the likelihood of these active wires electrically coupling with the inactive wires. Those skilled in the art will readily envision a multitude of ways to make a mechanism 1502 which would selectively impart tensioning force to only the wire(s) to be activated, or to all wires in one planar direction.

In some embodiments, constant force springs 1503 are wound around a gear-like spool 1504 which can be locked into place, such as by a flange or tab(s) 1506 prior to tensioning or power activation.

Figure 23:
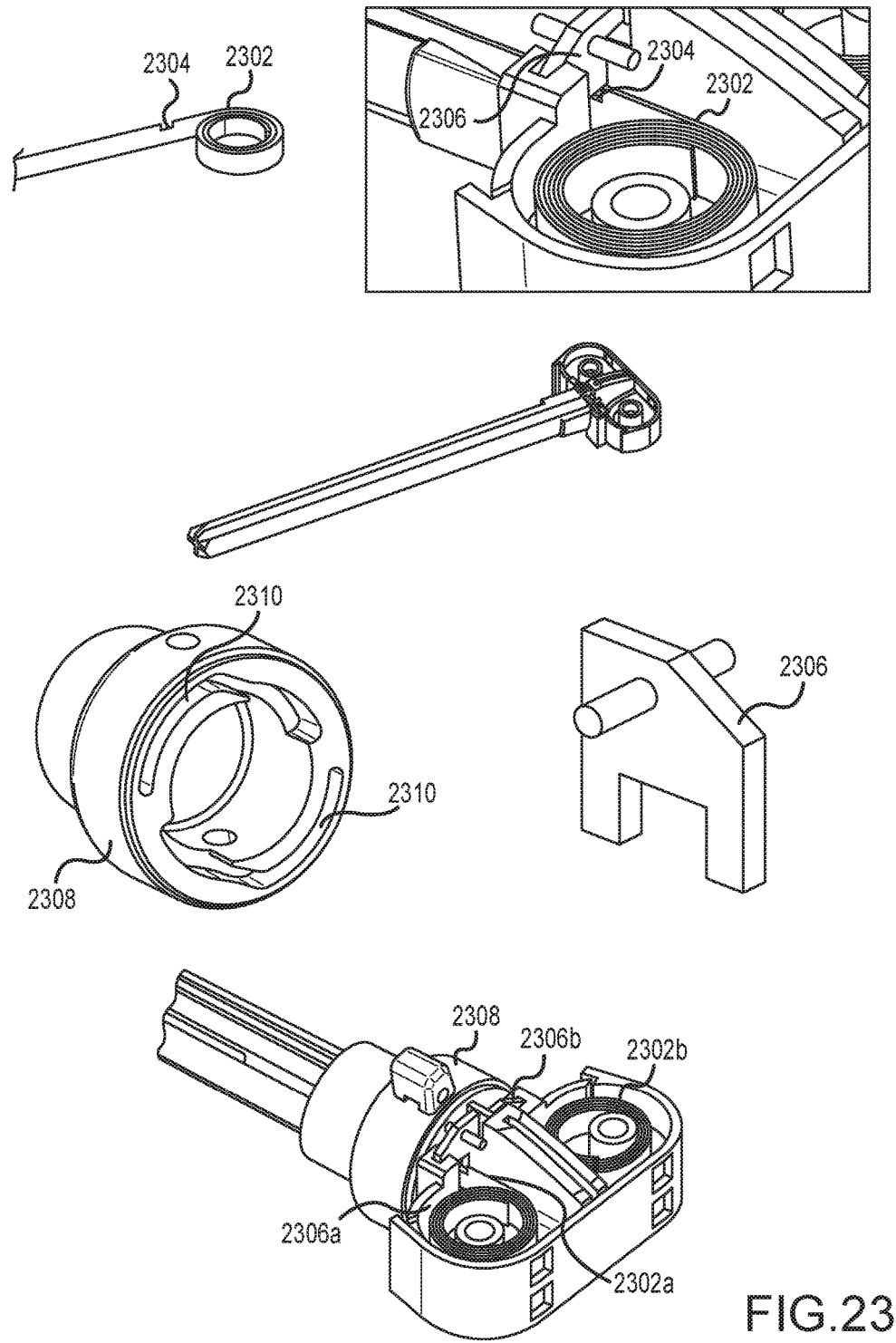
FIG. 23 illustrates a tensioning instrument.

In some embodiments, and with reference to FIG. 23, a constant force spring 2302 is provided with a notch 2304 or additional engagement feature. A detent gate 2306 or gates can be temporarily inserted into the engagement feature or notch 2304 so that the constant force spring 2302 is configured to be temporarily maintained in an extended state. The detent gate(s) 2306 can be selectively lifted, rotated, or slid to unlock one or both of the constant force springs 2302 and enable the spring(s) 2302 to tension the wires 122, 124 or wire sets 153, 160. In some embodiments, a slotted collar 2308 may be provided so as to enable a user to lift or disengage the gate(s) 2306, such as by rotating the slotted collar 2308. The slot(s) 2310 may be oriented such that a rotational movement will translate to a linear or vertical motion at a pre-selected rotational location.

In some embodiments, a plurality of detent gate(s) 2306, such as four, are provided to engage each spring 2302 of a 4-spring assembly. In some embodiments, the gates 2306 are configured to lift or raise at a specified rotational angle of the collar 2308. In some embodiments, a first gate 2306a is configured to lift or disengage from a first spring 2302a before a second gate 2306b lifts or disengages from a second spring 2302b. The collar 2308 may be configured to control the disengagement in this manner.

In some embodiments, a motorized spring and/or a bivalve pneumatic instrument may be used in place of the slots 2310 in the collar 2308.

Figure 24:
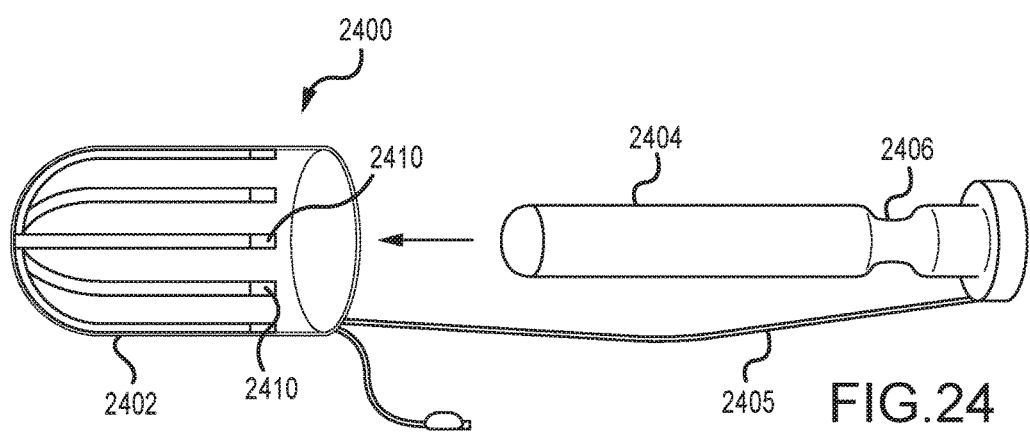
FIG. 24 is a perspective of an introducer prior to insertion preparation.
Figure 25:
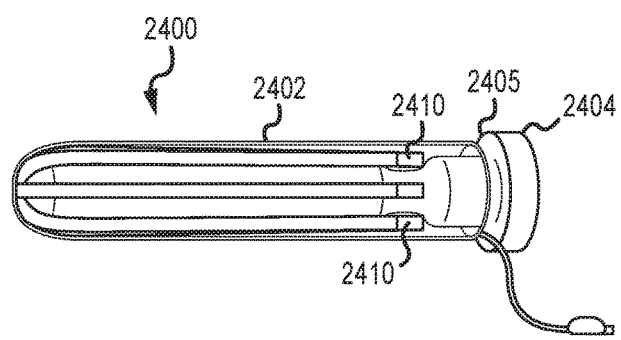
FIG. 25 is a perspective view of the introducer in FIG. 24 prepared for insertion.

Turning now to FIGS. 24 and 25, in some embodiments, a tissue segmentation device may be provided with a removal bag 161, 2400. The bag 2400 may include a flexible container 2402 substantially as described in other portions of this document, and an introducer 2404 to assist in inserting the bag 161 through an incision site. In some embodiments, the introducer 2404 may include a mandrill with a distal shape that protects the wire(s)/electrode(s) from kinking. The introducer 2404 may be a separate component that is removed after the bag 161 is fully placed in a patient cavity, or, in some embodiments, may be an attachment to a distal end of the tissue segmentation device, and may be removed after the bag 161 is placed, or can be a feature designed into the distal end of the tissue segmentation device. The introducer 2404 may be placed into the bag 161, 2400, and the flexible container 2402 may be collapsed around the introducer 2404 and held in place during insertion. A recessed area 2406 of the proximal end of the introducer 2404 may be provided to allow the active electrode connectors 2410 to be recessed during insertion to reduce the chance of catching on the patient incision site.

In some embodiments, and with reference still to FIGS. 24-25, an introducer 2404 may have a means for mechanically coupling a drawstring 2405 to a semi-rigid ring around the bag opening. In some embodiments, the introducer 2404 may be withdrawn from the bag such that the drawstring 2405 is accessible through the incision site by a user or grasping instrument, thereby aiding user access to the drawstring 2405 when exteriorization of the bag opening is desired. The means for coupling the drawstring 2405 may be any means known to those skilled in the art, now developed or as-yet to be developed, and may include binding, gluing, welding, fastening (such as a screw fastener), or any other means.

Those skilled in the art will also understand that the drawstring 2405 and/or other components described herein may be made of or have a surgical steel, a flexible metallic material, a metallic coating, a flexible metallic coating, a sterile polymeric material, a spring, a coil, a memory-retaining material, and/or other materials selected for the intended use in a surgical environment and for minimizing transfer of contaminates to the patient. In some embodiments, the drawstring 2405 may be configured to bias the introducer 2404 and bag 161, 2400 to a prepared-for-insertion or compressed configuration.

Figure 26:
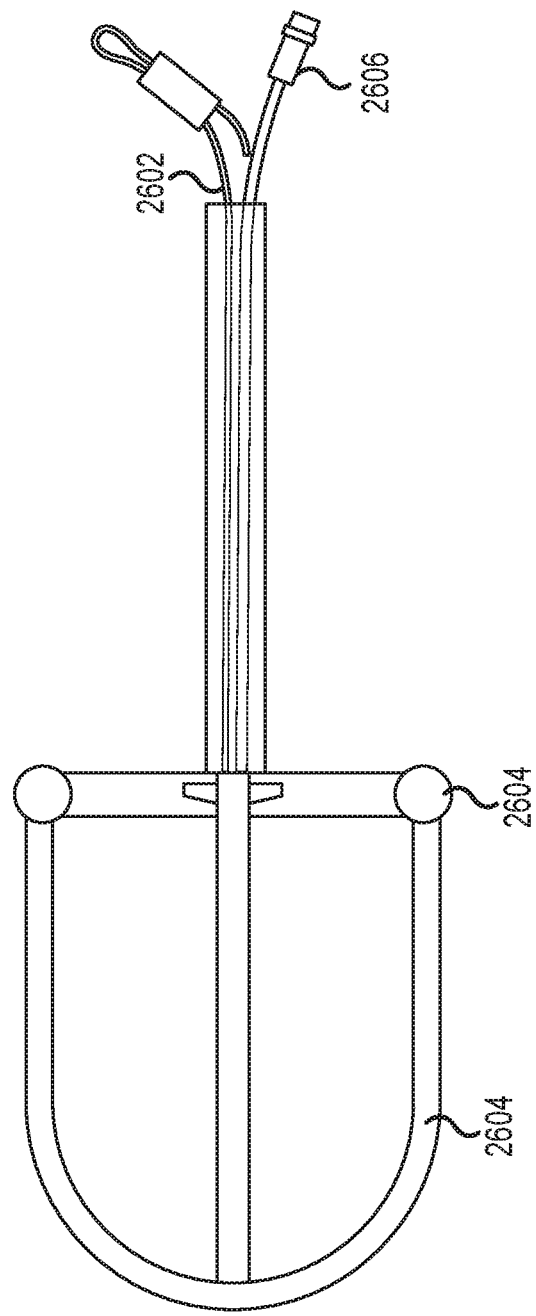
FIG. 26 is a side section view of an inflator.

In some embodiments, and as illustrated in FIG. 26, a return cable integrated with tubing to form a secure tether may be provided to enable a user to exteriorize the bag 161. In some embodiments, the removal bag 161 includes a plurality of inflation areas 2604 within the bag that can be inflated using low pressure air. These inflation areas 2604 are used to provide rigidity to the bag opening and/or the side walls of bag 161 to assist in loading the tissue specimen into the bag 161. The inflation areas 2604 may include or be coupled to a common inflation tube 2606 that, along with the return electrode cable 2602, protrudes out of the patient when the removal bag 161 is inserted to load the tissue specimen.

In some embodiments, the return electrode cable 2602 and inflation tube 2606 are mechanically attached together and mechanically supported where they exit the removal bag 161 such that they can be used as a means to pull the bag 161 toward the incision site after the tissue specimen is loaded. After deflating the bag 161, the bag opening may be pulled through the incision site by pulling the return cable/inflation tube assembly 2602, 2606 until the bag opening or a portion of the bag opening is exteriorized allowing the user to pull the remaining bag opening out of the patient. This integration of the return electrode cable 2602 and tubing 2606 may be a molded assembly, a film applied around both components, layered together as one assembly, tied together along the length of common attachment, or can bonded using adhesive or other means.

Figure 27:
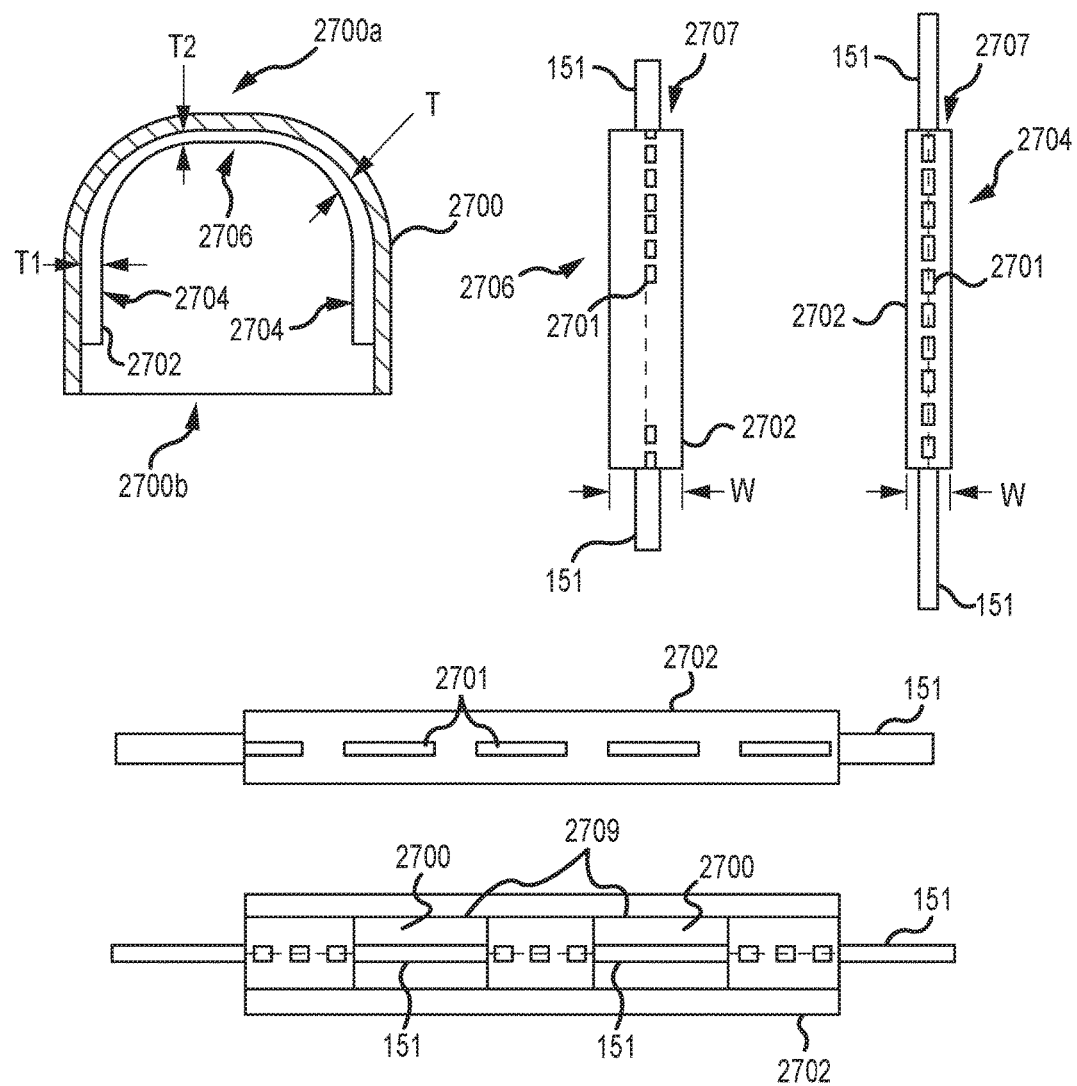
FIG. 27 illustrates several views of tissue removal bag components.

Turning now to FIG. 27, a tissue removal bag 2700 for the system 100 may be provided. The bag 2700 may utilize a thin layer of film 2702 that contains perforations 2701 to secure the electrode(s)/wire(s) to the interior surface of the bag 2700. These perforations 2701 may be designed to control the release of the electrode(s)/wire(s) during the pretension step, or may be designed to partially release the electrode(s)/wire(s) at select locations and to release the electrode(s)/wire(s) at the remaining locations during the travel of the electrode(s)/wire(s) during cutting. In some embodiments, the perforations 2701 may be sized/spaced to be approximately 4-5 perforations per centimeter (or about 12 perforations per inch). In some embodiments, 3-4 perforations per centimeter (or about 8 perforations per inch) may be selected. Control of the release of the electrode(s)/wire(s) during pre-tensioning may be achieved by selection of the perforation per length configuration, combined with the thickness T and elasticity of the film 2702 containing the perforations 2701, along with the thickness and rigidity of the material in which the perforation layer is attached.

In addition, the width W of the dimension in which the film 2702 is not attached to the bag 2700 defines a wire channel 2707. This wire channel 2707 is an important dimension related to the ability of a wire (e.g. wire 151 as illustrated, or any wire 122, 124 or electrode described herein) to find the perforation 2701 when the tensioning force is applied so that it creates the separation required to release the electrode(s)/wire(s) 151, 122, 124. This width W, combined with the elasticity and/or thickness T of the material 2702, can be adjusted in addition to the perforation per length values and patterns previously described to provide the optimal wire release performance.

In some embodiments, the width W of the wire channel 2707 for a tissue removal bag 2700 is less than 0.5 centimeters (or less than about 0.200 inches); in some embodiments, the width is less than about 1.63 centimeters (or less than about 0.064 inches). Another means to help increase the probability of the wire 151 separating the perforations is to have multiple perforation lines 2701 in parallel to each other in the film 2702 so that as the wire 151 is routed in the channel 2707, the chance of finding the line of perforations 2701 is greater.

Selection of the appropriate combination of these values can provide the release of the electrode(s)/wire(s) in a manner that advances as the electrode(s)/wire(s) advance during cutting, and can guide the electrode(s)/wire(s) along a perforation channel 2707, resulting in a more predictable segmentation cut. This may be accomplished with the same perforation per length values across some or all sections having the perforations 2701, can be enhanced by using different perforation per length values in different sections, can be a linear, logarithmic, or other pattern of increasing or decreasing perforation per length values, or can be patterns of perforations 2701 followed by open areas 2709 to enhance the separation as the electrode(s)/wire(s) travel(s).

Those skilled in the art will appreciate that as multiple wires are used within the bag, intersection points are created where a wire set intended to apply power such as RF energy to the tissue crosses in close proximity to the wire sets that are not intended to have power or RF energy. Some amount of power will tend to couple, either capacitively, inductively or conductively, to the inactive wire sets. This can result in cutting of unintended wire sets which can lower the current density, as the total active electrode surface area is increased, such that the desired cutting performance is not achieve. As such, this coupling must be managed to avoid unintended wire set cutting.

Figure 99:
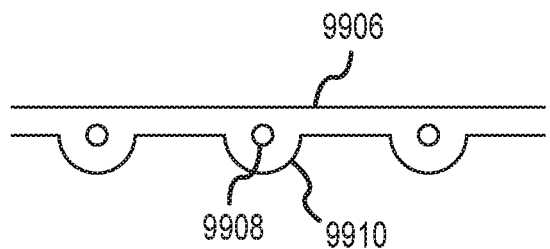
FIG. 99 illustrates some components for wire management.

With brief reference to FIG. 99, in some embodiments, one or more electrode wires 9908 may be molded in or contained in a film 9910 or portion of a bag wall 9906. FIG. 99 illustrates a top view of how some electrode wires 9908 might be positions.

In some embodiments, the coupling can be managed electrically by providing a higher isolation between the intended and unintended wire sets. This can be achieved by aligning the perforation portion of the channels at the intersection points. This provides the greatest benefit for conductive coupling and provides a higher dielectric for capacitive coupling.

In addition to increasing the isolation, the overall amplitude of the electric field can be reduced. This is achieved by controlling the amount of exposure the active wire has with the tissue. As the contact between the wire and tissue is increased, the effective impedance is reduced resulting in a lower electrical field amplitude along the wire. In addition, as the voltage on the wire sets reaches a level where arcing begins, the arc path will preferentially be through the tissue and not to the unintended wire sets.

The coupling can be managed mechanically be providing a higher mechanical load to the wire sets intended to cut verses the unintended wire sets. This can be achieved with separate pre-tension forces, or with different forces applied for the duration of the cutting process. If the coupling is observed between the intended and unintended wire sets, the differential force between the two wire sets will increase the separation between the two as the intended wire set advanced through the tissue. The increased separation will reduce the amplitude of the coupling between the two wire sets, and ultimately to an insignificant level.

With continued reference to FIG. 27, perforations 2701 in the bag material may be used as a temporary method to secure or contain the wires until a force or force aided by temperature rise can allow the release of the wire. Those skilled in the art will understand that if the material containing the perforations or attaching the wires is a film that has a very low temperature melting point, the wire channels may be configured to release primarily with the temperature created form the power or RF energy activation. In this manner, the mechanical force is a secondary means of releasing the wires from the bag and the active electrode wires activated for cutting will more easily release from the channels upon initiation.

A feature may be combined with the wires to enhance the ability of the wire sets to break away from the bag perforations. For example, the wire 151 may have a wedge shape feature that is attached to the wire or Teflon tubing to cut or improve the tearing of the perforations as the wire moves through the tissue.

Some embodiments may be configured to reduce the likelihood of a cut tissue segment that is too large to remove through the incision site. In some embodiments, multiple layers of active electrode wire sets are attached with perforations to layers of the bag.

For example, if an electrosurgical device 102 is designed to have four tensioning mechanisms that apply power to four separate active electrode wire sets, the bag may include an outer layer, a second layer that has the return electrode coupled to the outer layer, and a series of internal layers stacked inside the bag. Each of these internal layers may be an insulated layer with perforations running the length of the layer that has four active electrode wire sets attached with perforations. These layers may conform to the shape of the outer layer so that they can be easily inserted into the outer layer. The layers may also have an opening in the bottom area of each layer so that the return electrode is exposed to the tissue when the internal layers are in place. The user may attach the connectors of the active electrode wire sets from the innermost layer to the electrosurgical device 102.

The tissue segmentation may be performed as described in Applicant's co-pending application PCT/US15/41407. When the segmentation is completed and the wires are removed from the layer, the layer may be removed by the surgeon by hand, such as by pulling on the exposed portion of the inner layer and causing the perforations in of the layer to separate, allowing the film to be removed. This removal exposes the next set of active electrode wire set connectors. A second electrosurgical device 102, or a device that can be reloaded to the fully extended position, can now be connected to the tissue removal bag in the same manner as previously described. Those skilled in the art can understand that this increases the number of segmentation cuts and reduces the chance that a large tissue segment will remain after all segmentation steps are completed. The layers of the bag may be constructed such that each internal layer is rotated slightly from all other layers to further reduce the likelihood of leaving a large tissue segment after all segmentation steps are completed.

Continuing with FIG. 27, in some embodiments, the film 2702 is separated into a plurality of different regions, and in some embodiments, two regions. The bottom of the bag 2700*a* may include the bottom region 2706, which may be a hemisphere region as illustrated, although those skilled in the art will understand that a box shape or any other shape may be selected depending on the particular purpose of the bag 2700. The sides of the bag 2700 may have the side region 2704. Due to the forces applied to the tissue specimen by the electrode(s)/wire(s) during pre-tension and cutting, the force in the bottom region 2706 may be less than the forces in the side region 2704, thereby biasing a release of wires from the side before a release from the bottom. To counteract this tendency, those skilled in the art will understand that it may be desirable to provide a film 2702 having a first thickness T1 at a side portion that is different from, such as thicker than, a second thickness T2 at a bottom portion. It may be desirable to provide a side section of the film 2702 having a first pattern of perforations 2701 and a bottom section of the film 2702 having a second pattern of perforations 2701 different from the first pattern of perforations 2701.

For example, FIG. 27 illustrates an embodiment in which the bottom region 2706 has a 0.001 inch (25.40 um) thick film and a 12 tooth per inch (about 4.72 tooth per centimeter) perforation to provide a lower break force to separate the perforations 2701. The side region 2704 may have a film 2702 that is about 0.0022 inches (about 55.88 um) thick and an 8 tooth per inch (about 3.15 tooth per centimeter) perforation 2701 to ensure that a slightly higher force is required to separate the perforations 2701 in the side region 2704 as compared to the bottom region 2700*a*. This embodiment takes advantage of the fact that during manipulation and loading of the tissue specimen, higher forces occur on the side regions 2704 than the bottom region 2700*a*, allowing a lower perforation force to be used in the bottom region 2700*a* without concern for failure during the loading process. This configuration also takes advantage of the higher side region force so that the electrode(s)/wire(s) do not fully and/or prematurely release with or during a pre-tension step. This allows the electrode(s)/wire(s) to release during cutting such that the perforations 2701 act as a guide to align the travel of the wires through the tissue with the perforations 2701.

Other examples of perforation patterns are illustrated in FIG. 27. In some embodiments, a method of manufacturing a retrieval bag for an electrosurgical device may be provided. The method may include providing a flexible bag 2700 having an interior region at least partially coated with a film 2702, and perforating the film in a pattern, the pattern configured to control a release pattern of at least one electrosurgical electrode or wire. The method may include providing a film 2702 having a first thickness T1 on a side portion and a second thickness T2 on a bottom portion, the second thickness T2 different from the first thickness T1.

In some embodiments, providing open windows 2709, or omission of the perforation layer at desired intervals or location(s), aides in wire release from the bag, as illustrated in FIG. 27. These windows 2709 do not constrain the wire(s) 151, and enable direct contact between the active electrode wire 151 and the tissue. The area(s) of perforation, or perforation walls, provide a temporary attachment of the wires 151 to maintain alignment.

The ratio of windows 2709 to perforation walls may be adjusted or selected in a manner similar to the perforation per length value, to control the force required to release the wire 151 through the perforations. In addition, because the perforation walls cover the active electrode wire(s) 151 prior to release, the perforation walls may provide an isolation layer and/or the isolation layer may have the perforation walls.

Cut initiation and the early cut performance may be enhanced in embodiments having windows 2709 placed in desired locations around the tissue specimen. For example, due to the mechanical load and electric field distribution of the wire(s) 151, the active electrode wire(s) may preferentially begin cut initiation at a first portion of the bag side walls. Placing a window 2709 at or near the first portion will enhance this initiation. Placing a wall at or near a second portion, in contrast, moves the cut initiation towards the second portion. By contrast, placing a perforation wall at or near the first portion may restrict the cut initiation at the first portion, unless the voltage created on the active electrode wire 151 can create an arc through the perforation wall. The windows and/or perforation walls may thus be configured such that a selected portion of the bag will provide the first portion of the tissue being cut.

That is, the cut may be controlled so as to travel from a first region of the tissue to a second region of the tissue.

Figure 28:
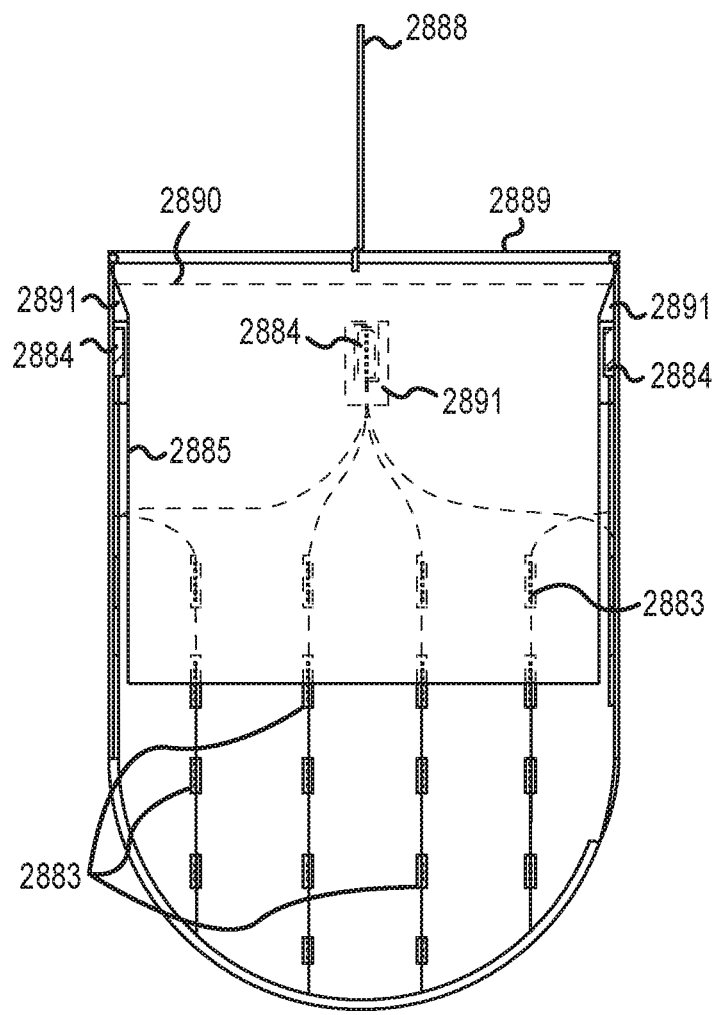
FIG. 28 illustrates a bag having an apron.

Turning now to FIG. 28, the perforations 801 or perforation walls 2883 do not extend in some embodiments to the bag opening region, allowing the proximal end of the electrode(s) or wires(s) to be easily terminated into connectors 2884 during manufacturing and/or to allow the user to easily guide the wire set connector, or termination of the wire(s) to the corresponding receptacle in the segmentation instrument or other device intended to attach to the wire connectors. Having the portion of the electrode(s) or wire(s) not secured by the perforation walls near the bag opening allows the wires to freely extend away from the interior surface of the bag.

Figure 100:
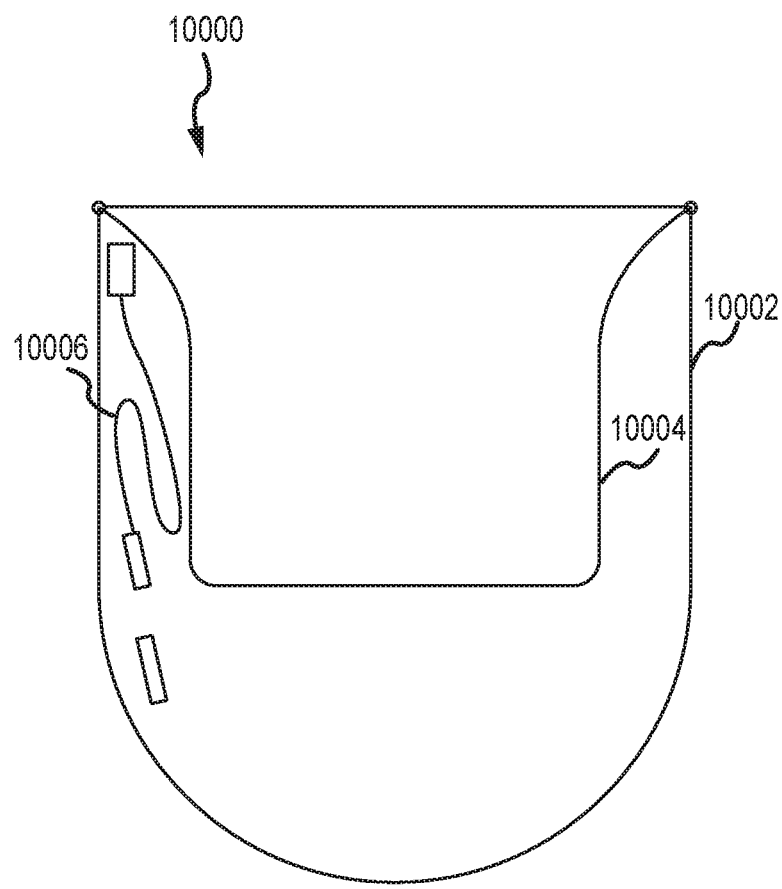
FIG. 100 illustrates a side section view of some components of a wire management system.

With brief reference to FIG. 100, a bag 10000 may include an outer bag 10002 and an apron 10004 for managing placement of the wires/electrodes 10006.

Turning now to FIG. 28, an "apron" or additional layer of film 2885 is provided in the bag to protect the wires from damage during loading. This apron may be attached to the bag opening at the proximal end or near the bag opening.

The apron may be of a cylindrical shape that is continuous or a series of segments that extend around the circumference of the inside of the bag. The apron may be positioned so that the wires and/or wire connectors are located between the apron and another feature in the bag. The apron may extend distally along the interior surface of the bag to a point near or beyond the perforations so that any wire not contained by the perforations will remain beneath the apron. With the apron, the tissue will not directly contact the wires or wire connectors and may be easier to load. The apron may also protect the wires during loading, manipulation of the bag and exteriorization.

The apron 2885 may have one or more pouches 2881 to temporary hold proximal portions or connectors of the wire sets.

Those skilled in the art will understand that the apron may have benefit with any feature located on the bag surface that can interfere with loading of the specimen, and/or may be a benefit to protect during the loading, manipulation, exteriorization or other procedural steps. In some embodiments, an apron 2885 may isolate or protect an electrode or wire 151 as previously described, a mechanical member such as a wire, cable or mesh, a protrusion of the bag surface, monitoring electrodes, temperature sensors, pressure sensors, features embedded into the bag, and/or other items that are located in the bag, placed in the bag or used in proximity of the interior surface of the bag.

Figure 29:
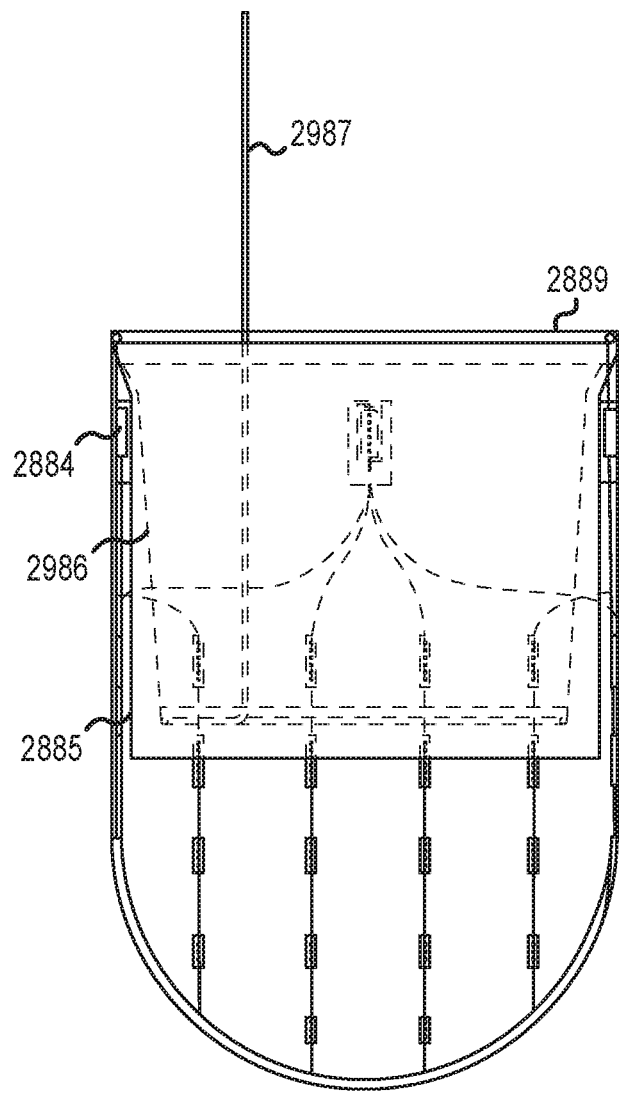
FIG. 29 illustrates a bag having a drawstring.

The apron may 2885 also be used as a containment flap 2986 (see FIG. 29) to help retain the contents of the bag after loading. The containment flap 2986 may be sized to remain in between the loaded tissue specimen and the interior surface of the bag such that the apron does not restrict the tissue from being loaded into the bag. The containment flap may also be sized such that when the tissue is loaded into the bag the tissue falls, or is placed below, the distal most edge of the apron, or the distal most edge of the containment flap may be raised above the tissue after loading is complete. As a result, the apron 2885 may be configured to restrict premature or unintentional removal or displacement of the tissue.

In some embodiments, the device 102, 200 may have a bag with a removable apron 2885. The removable apron 2885 may be selectively positioned interior of the bag and one or more cutting electrode wires 151. The removable apron 2885 may be movable relative to the bag to expose the wires 151.

In some embodiments, a drawstring 2987 is provided, and may be positioned or located at a bottom or distal edge of the containment flap 2986 to enable a user to close the containment flap and therefore capture the tissue specimen as well as contain fluids. This feature may be beneficial where the contents of the bag are desired to be contained during manipulation and exteriorization of the bag, such as where the tissue specimen is believed or suspected to contain cancerous cells. The containment flap and drawstring may also protect the bag features during loading of the tissue.

In some embodiments (see FIG. 29), two apron layers may be provided, a first apron layer 2885 to protect the bag features as previously described, and a second containment flap layer 2986 that can be used to contain the tissue specimen in a manner substantially as previously described herein.

After tissue specimen loading, the containment flap 2986 may be used to assist in exteriorizing the bag opening. Using a drawstring 2987 that is coupled to the distal edge of the containment flap along the circumference, pulling the drawstring through the incision site will raise the distal edge of the containment flap around the tissue specimen and draw the opening toward the incision. The drawstring may close or substantially close the containment flap and guide it through the incision. The bag opening may follow as it is pulled through the incision opening. When the bag has reached it intended exteriorized position, the bag can be secured with a semi-rigid member 2889 around the opening, can be inflated to secure or can be held with other mechanical means including being held in place by an attending surgeon. The drawstring can be loosened and the containment flap can be spread and/or cut to provide access to the bag features on the interior surface, such as electrode(s) and or wire(s) or wire connectors.

In some embodiments, a separate means of exteriorizing the bag can be used so that the apron 2885 can remain in place until after exteriorization. The bag can be exteriorized by coupling a lead or suture 2888 (see FIG. 28) to the semi-rigid member 2889 which will help guide the bag opening toward and through the incision site. After exteriorization, the apron can be accessed and raised around the tissue specimen and out of the incision site where it can be cut or have a perforation feature 2890 that will allow the user to tear it away, providing access to the bag features on the interior surface, such as electrode(s) and/or wires(s) or wire connectors 2884. This embodiment has the additional benefit of reducing the chance of contact of the peritoneum or incision site with portions of the apron layer that have come in contact with the tissue specimen during loading and manipulation. The apron may collapse somewhat within the interior bag volume. This "curtaining" effect can cause the apron to not remain in close proximity to the interior surface of the bag. A feature can be added to the apron and corresponding location on the interior surface of the bag to help hold the distal most portion of the apron in place.

Figure 30:
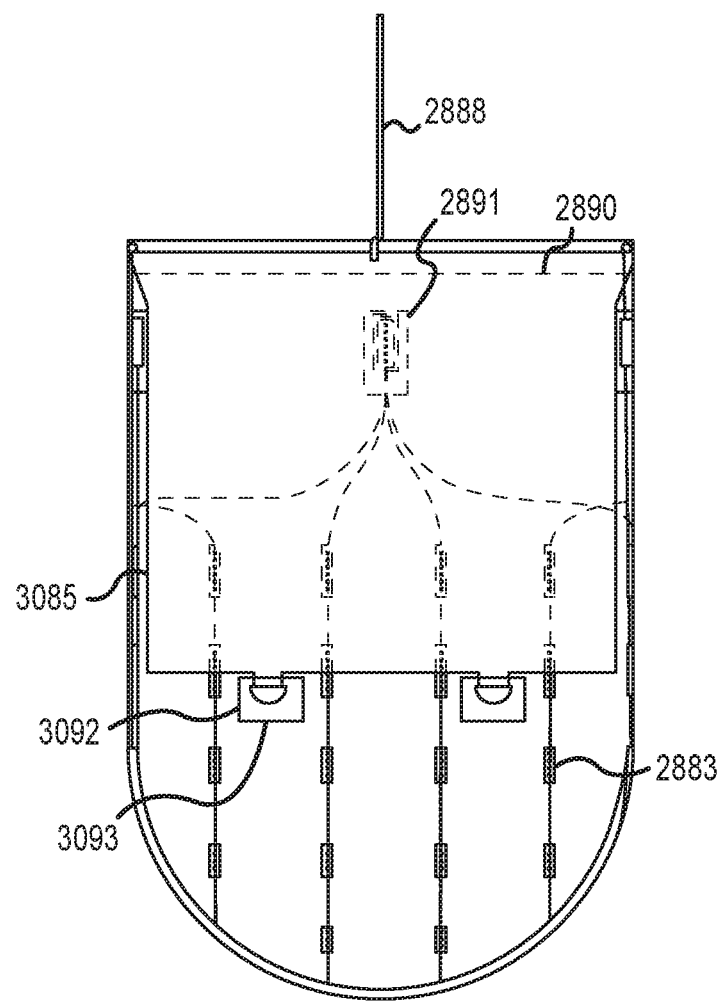
FIG. 30 illustrates a bag.

In some embodiments, and as is illustrated in FIG. 30, a feature on the apron 3085, or tabs 3092, can be provided in the bottom or distal portion of the apron. Corresponding features, slots 3093, can be provided in a film layer added to the interior surface of the bag. The tabs can be inserted into the slots during manufacturing to help retain the apron close to the bag surface until the user applies a force to pull the tabs out of the slots freeing the distal end of the apron.

A method to hold the distal portion of the apron against the interior surface of the bag is to weld or heat seal small locations around the circumference of the bag. These welds are designed to hold the bag in place but easily break free when the user applies a force to remove the apron. Additionally, a larger portion of the distal apron can be welded to the interior side of the bag with perforations added to the apron to allow it to be torn away by the user.

In some embodiments (see e.g. FIG. 28), the interior surface of the bag may have a positioning feature configured to create a location for the wire crimp connectors to reside until connection by the user. The positioning feature may be a pouch, fold, or pocket 2891 created in the interior side of the bag. This pocket can be shaped to receive one or more connectors, and/or to removably hold the connector(s) in place until the connector(s) re to be used. In some embodiments, an opening in the bottom of the pouch may be provided and sized to allow the connector(s) to be placed through the opening but not to allow the connector(s) to unintentionally fall back through the opening.

In some embodiments, the bag has a pocket with an opening on the top and a slot along the side so that the wires can be placed in the slot and the connector placed into the pocket.

In some embodiments, the location of the pocket is selected to align with the connections on the segmentation instrument to enable connection. In some embodiments, a pouch, pouches, pocket, or pockets are placed slightly below the proximal bag opening such that they remain under the apron to protect the connectors during insertion of the bag, loading of the tissue specimen and/or exteriorization.

One advantage of the apron is that it keeps the wires and connectors out of the way during loading. Multiple and different aprons might be used to cover different wire sets where one apron can be removed first to expose one or more connectors for connection to the instrument before a second apron is removed to expose one or more other connectors. In another embodiment, one apron may have openings for the wire connector(s) to allow connection to the instrument while keeping the wires out of the way and avoid inadvertent wire tangling. In this embodiment one or more first aprons with the connector openings may cover the wires while still allowing access to the connectors, while one or more second aprons could be used for the primary purpose of protecting the connectors prior to connection with the instrument.

The bag may include an additional guide that contains common sets of wires so that they maintain alignment near the bag opening above the perforations. The guide may include a heat shrink, tubing and/or other means to hold wires that are crimped or attached together in a common wire connector in close proximity One or more guides may be used at locations along the wire(s) in which the wires can perform as intended if they are held together, such as above the perforations at a location near the wire connector.

Figure 98:
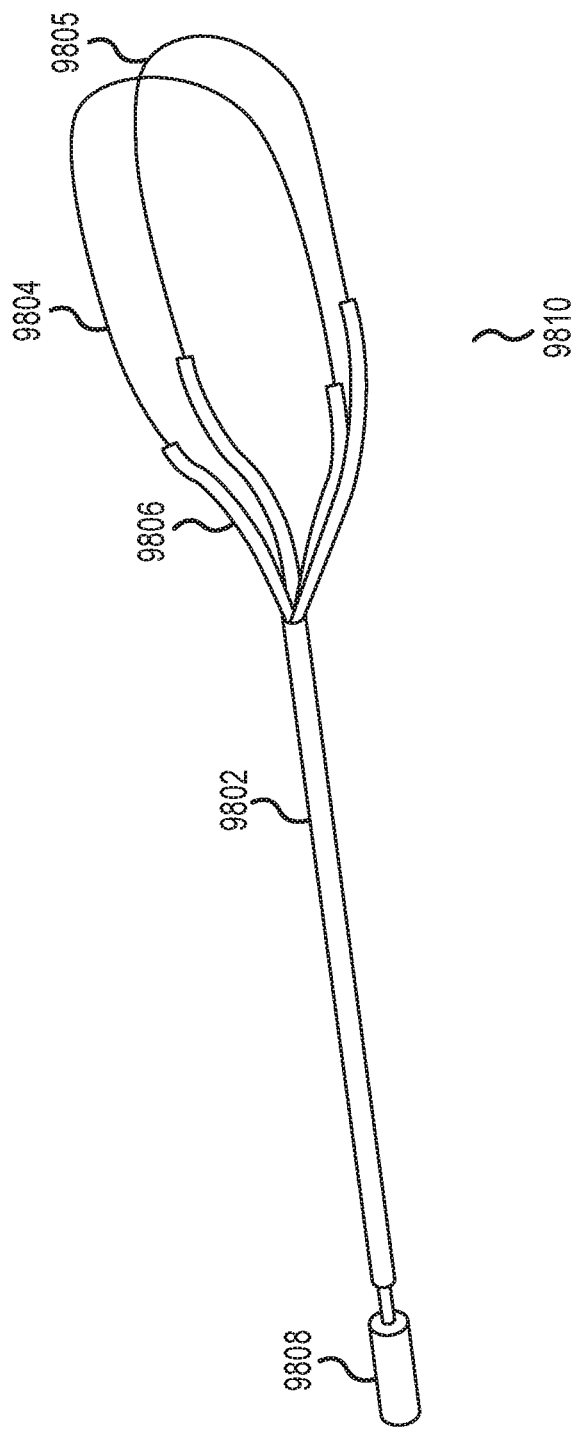
FIG. 98 illustrates a perspective view of some components for wire management.

With brief reference to FIG. 98, in some embodiments, a guide lumen 9802 may be provided for controlling relative placement of a wire set 9810 having a plurality of wires 9804, 9805 or electrodes. A proximal end of the guide lumen 9802 may be coupled to or unitary with a connector 9808 for attaching the wire set 9810 to the rest of the device 102 (see e.g. FIG. 1). The guide lumen 9802 may be flexible or relatively stiff in some embodiments. In some embodiments, an isolation zone for electrode wires may be provided by an isolating coating 9806 or material. The isolating coating 9806 or material may be configured to bias the wire electrodes 9804, 9805 away from each other, so that the wires 9804, 9805 are more suitably spaced when positioned about a tissue specimen.

The guide may extend from a position proximal the bag opening towards the point at which the wires need to separate to be routed to their corresponding wire channels. This distal termination of the guide should be selected to not create undo tension of the wire so that it will naturally remain in close proximity to the bag inner surface as it exits the wire channels and also should not interfere with the tissue loading or the process of applying pre-tension to the tissue while advancing the introducer tube.

Some embodiments for guiding the wires near the bag opening may include an extended wire channel. This may be used independently or in conjunction with the heat shrink or other means of capturing the wires as previously described. The extended wire channel may be comprised of two polyurethane films that create narrow channels for the wires to be placed in during manufacturing. The films may be extensions of the wire channels attached to the inner surface of the bag and they may be attached or not attached to the inside surface of the bag above the perforations.

In some embodiments, a common film that is attached to the side wall of the bag up to the height of the maximum tissue specimen and free of the inner surface of the bag above this location may be provided. The connector(s) may be pulled out of the bag for ease of connection to the segmentation instrument, while still maintaining containment of the wires between the wire connector and the wire channels on the bag.

In some embodiments, the two film layers are attached together by RF sealing, welding, and/or any other means to form a lumen where containment is desired. In some embodiments, perforations are provided to allow the wires to be released from the guide by the user. The films can also be designed with a thin inside film layer such that the user can "tear" the wires through the film prior to applying the pre-tension, thereby allowing unrestricted travel of the pre-tension introducer tube into the incision site in preparation for the cutting procedure.

In some embodiments, an extended wire channel is located underneath an apron, with the proximal termination near the connector temporarily attached to the inner surface of the bag. This attachment may be with a heat sealed connection that is designed with a perforation for the user to tear away when making the wire connection, may be a thin film such that the user can "tear" the extended wire channels away from the inner surface of the bag, may be attached with a slot in the side of the bag in which the extended wire channel is seated during manufacturing, and/or other methods of attaching this channel to the inner surface of the bag. In some embodiments, the attachment may be made with the wire connector by the use of a pouch or region of the bag near the opening in which the connector is placed during manufacturing in which the user can remove during wire connection.

The shape of the extended wire channels can be designed or configured to reduce the chance of twisting the wires when released from inside the bag. In some embodiments, a relatively wider extended channel may be provided. In some embodiments, a plurality of wire channels are provided and aligned in parallel on the same extended wire channel. The width of this extended wire channel resists the twisting of the wires as the user makes the connections. In some embodiments, Mylar strips or other material is attached to the wire channel film to enhance this anti-twist feature. In some embodiments, Mylar strips or other material is placed between the outer layer and a third layer of film so that the extended wire channel naturally stays aligned in the proper position.

Some embodiments provide separate channels within the segmentation instrument. For example, a tray that also aligns the tensioning mechanism during cutting may provide separate channels. Keeping the different wire sets separate within the instrument eliminates potential tangling or interfering with each of the different wire sets as they are tensioned and as the cut progresses.

The guide structures previously described become particularly important if the wire length is designed to allow a long separation of the wire connector to the specimen bag after exteriorization, or if the connections are fixed to the tensioning mechanism such as described in Applicant's co-pending U.S. patent application Ser. No. 14/805,358, the contents of which are incorporated herein by reference in their entirety.

In some embodiments, the return electrode cable extends from the distal portion, or bottom, of the specimen bag along the inner side wall of the bag and out of the bag opening. A means to ensure that the return electrode cable does not interfere with the wire sets is important to ensure unabated cutting. This return electrode cable can be separated from the wire sets by routing the cable in a location between wire sets under a return electrode cable "wire channel" composed of a polyurethane film in a similar manner as the wire channels that contain the wire set channels by bonding the cable to the inner side wall, or can be routed between layers of the polyurethane film or can be created by depositing conductive material on the bag surface with an insulation layer added to ensure electrical isolation.

The segmentation instrument may include an indication on the exterior surface that visually aligns the orientation of the instrument to a specific feature on exteriorized portion of the specimen bag. This allows the user to keep proper alignment during connection of the specimen bag wire connectors to the segmentation instrument. The alignment feature can be a label, an inserted feature, an overmolded feature, a molded feature in the housing, a silkscreened shape, a shape with a similar color, a registration number or other symbol or other means of identifying to the user. Some embodiments may include a contrasting line applied axially to the exterior housing of the distal tube such that when the line placed in alignment with the return electrode cable, the instrument is in proper alignment with the specimen bag for wire connections to be made.

With the introducer tube extended into the specimen bag and against the tissue specimen, any slack within the wires is removed and a tension is applied to all of the wire sets. This tension aligns the wires from the distal end of the introducer tube to the wire connection point inside the segmentation instrument. This alignment ensures that each wire set can advance within the instrument without interfering with the other wire sets. Without this alignment, the chance of a non-activated wire set catching or tangling with the wire set being cut increases.

Figure 31:
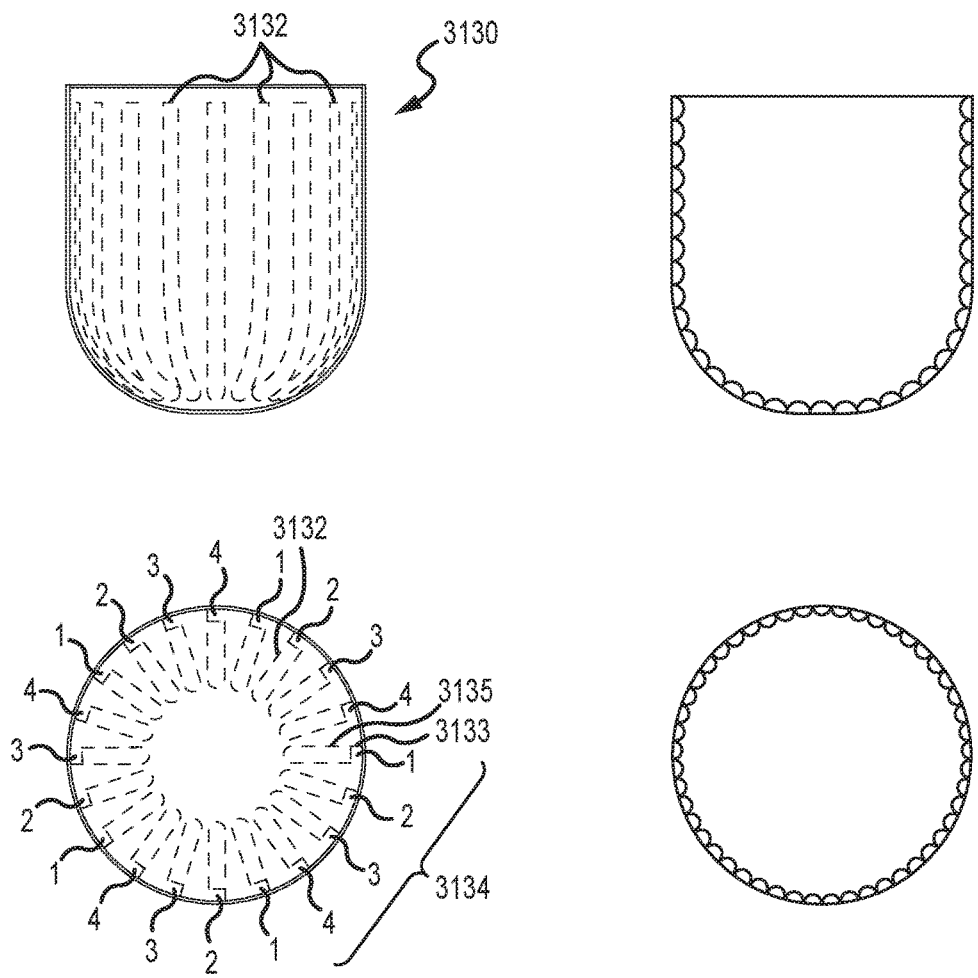
FIG. 31 illustrates several views of inflation mechanisms for a tissue removal bag.

Turning now to FIG. 31, a retrieval bag 3130 may be provided for the system 100, and the bag 3130 may include an inflatable feature. Inflation of the bag 3130 may be achieved using a honeycomb pattern of inflated or inflatable cells 3132. A plurality of inflatable cells 3132 may provide a thermal barrier between the patient and the electrode(s)/wire(s) inside the bag 3130. If the inner layer is punctured or thermally fails, the cell(s) 3132 would collapse leaving the remaining cells 3132 intact, to continue to provide thermal protection. In some embodiments, the cells 3132 may include a plurality of inflation channels 3132, some or all with a separate means to hold the pressure such as a separate syringe or stopcock. In some embodiments, the bag 3130 may include small independent areas that have static air captured under pressure.

The inflated cells 3132 provide an additional thermal insulation barrier between the tissue specimen or electrode and the adjacent structures outside of the exterior surface of the removal bag. In contrast, if the entire bag is inflated as a single cell, failure of one of the layers would cause the inflation and thermal insulation to be lost. By providing multiple independent inflation areas 3132 in the bag 3130, if one of the layers in an individual region fails, the thermal insulation of that layer may be lost or reduced; however, the remaining inflation cells 3132 will continue to provide thermal insulation, and minimize any thermal damage caused to the patient.

With continued reference to FIG. 31, a removal bag 3130 with multiple inflation areas 3134 (labeled 1, 2, 3, 4), each with a separate source of pressure or with a separate means to hold the pressure, may be provided. Those skilled in the art will understand that any number of inflation areas 3134 may be provided, and that the same or fewer means to inflate may be provided. For example, a first inflation area 3133 may be fluidly coupled to a second inflation area 3135 such that a single pressurizing source 1 may pressurize both areas 3133, 3135.

In some embodiments, inflation features or functions are integrated within the wire channels. For example, a third layer may be provided at the channels. The first layer is the perforation layer, the second is a boundary layer and third is a bottom layer. The boundary layer and bottom layer are sealed so that when low pressure air or fluid in applied, the channel will inflate providing structure directly beneath the wire channels. This has a benefit in providing thermal insulation directly beneath the wire as well as helps provide structure which aides in release of the wire from the channels.

Figure 32:
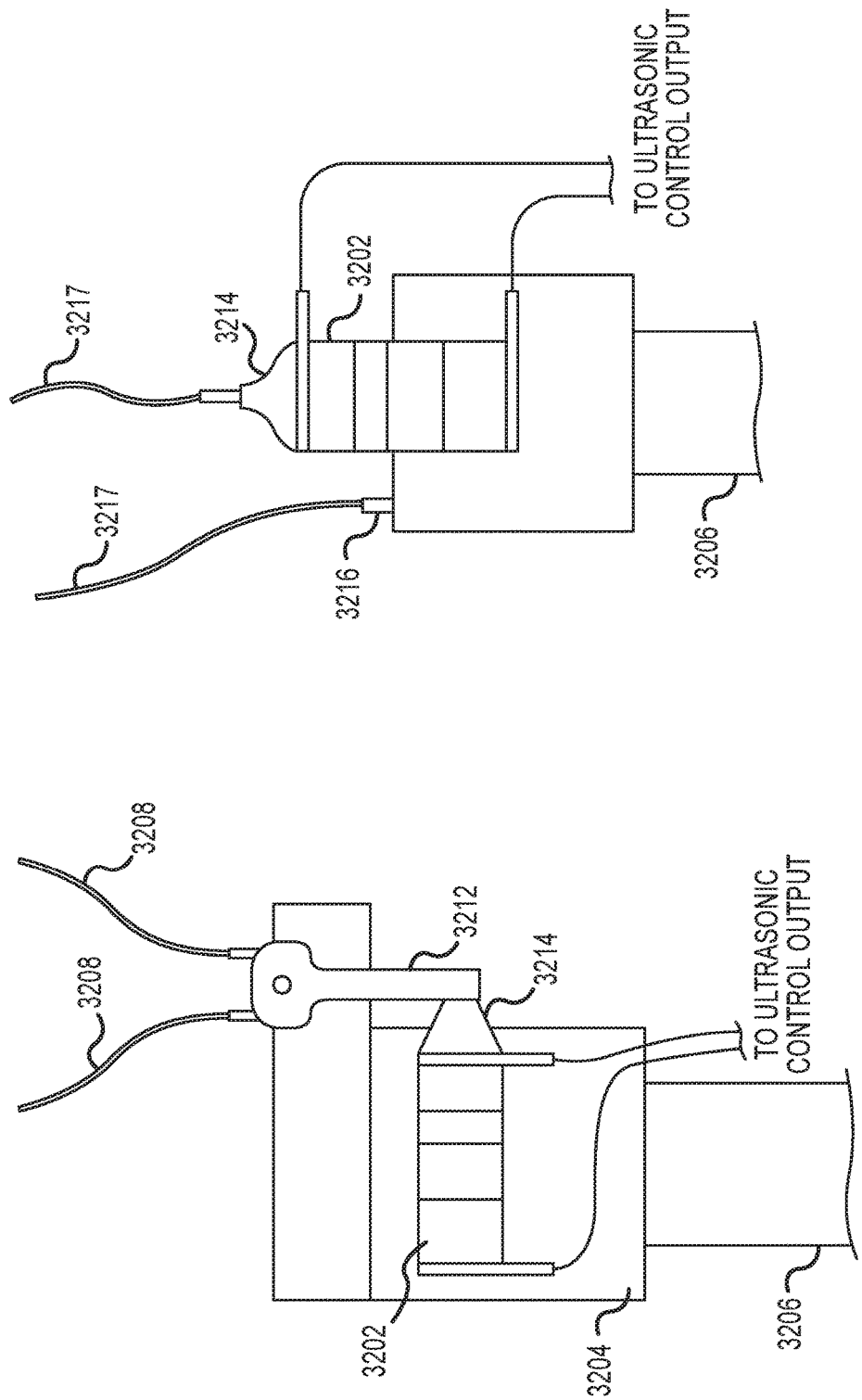
FIG. 32 illustrates two side views of components for an ultrasonic or vibratory segmentation device.

Turning now to FIG. 32, some embodiments for tissue segmentation include using ultrasonic energy to provide a vibratory motion to the electrode(s) or wire(s) in combination with or independent of a voltage and current applied to the tissue through the electrode(s) or wire(s). As previously described, the mechanical load F (see also FIG. 2) on the wire 122, 124 is critical, and may be a constant force, or may be applied dynamically. Dynamic loading may include use of vibrations where a transducer may be used to generate high frequency vibrations on the wire or wire ends. Using ultrasonics to create the vibrations may be used alone or with RF energy. In some embodiments, the ultrasonic transducer is on the segmentation instrument. When the wire connectors on the bag are connected to the segmentation instrument ultrasonic or high frequency vibrations are transmitted to the wires in the bag while the wires are pulled through the specimen using a spring or alternative means to apply the force.

In some embodiments, a piezoelectric crystal or piezoelectric stack of crystals 3202 is coupled to an end of the tensioning mechanism 3204 which may include a spring 3206 or other means of applying a mechanical load. As illustrated, an active electrode wire 3208 may be mechanically connected on an arm 3212 that vibrates perpendicularly to the tensioning mechanism 3204. The vibrating arm 3212 may be acoustically coupled to the piezoelectric crystal 3202. The crystal 3202 may use an ultrasonic horn 3214 or coupling to amplify the displacement, and may be oriented such that torsional motion in the ultrasonic range causes vibration axially or longitudinally along the electrode(s) or wire(s).

A control system may be applied to the electrodes of the piezoelectric crystal to drive the oscillation at the optimal frequency. The control system may utilize a phase-locked-loop to control to an optimized frequency that provides the highest ultrasonic power transfer through the wire and into the tissue. The phase-locked-loop may also have an amplitude modulated gain stage designed to maintain oscillation from the lowest force applied to the highest force applied by the tensioning device. Other control systems may be utilized such as a Wein-bridge oscillator or a fixed oscillation that does not maintain constant displacement used as a compliment to RF energy cutting.

In some embodiments, an introducer (see FIG. 5) may act as a protective sleeve for the incision site. In some embodiments, and with reference again to FIG. 32, one side of the electrode/wire 3217 is terminated in a fixed position 3216 on the tensioning mechanism 3204, and the other side of the wire 3217 is connected to the vibrating portion of the piezoelectric crystal 3202. The wire 3217 therefore is configured to expand and contract, and allow a tissue segmentation to occur with the agitation and frictional thermal response of the wire 3217 to tissue interface. The wire(s)

3217 may be configured to capture the entire specimen and cut the large segments, or may be configured to cut smaller portions of the tissue specimen that would be removed as a smaller tissue segment, in some cases in a similar manner as a mechanical morcellator.

Figure 33:
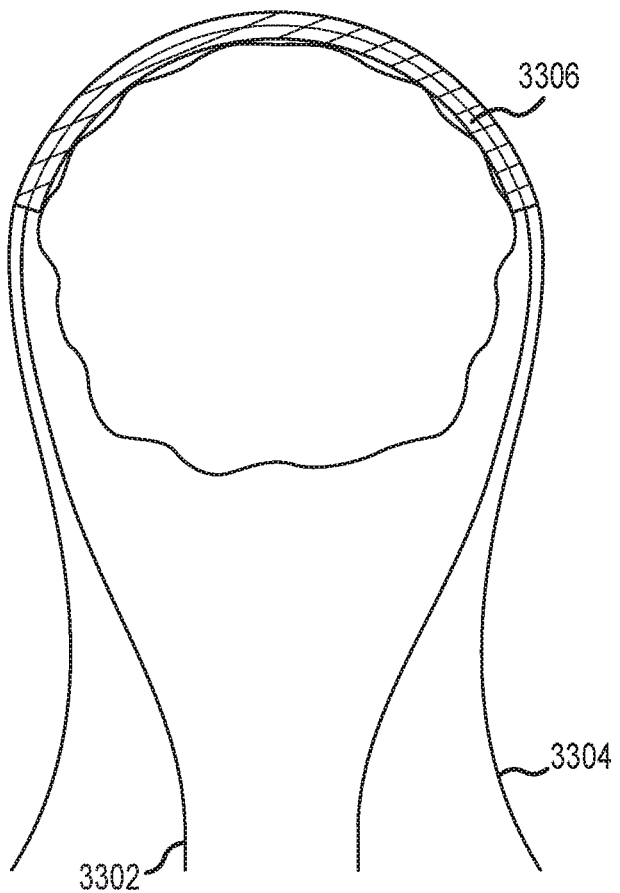
FIG. 33 illustrates a side section view of some components of an electrosurgical device.

Turning now to FIG. 33, a tissue segmentation device 102, 200 (see e.g. FIG. 1 or FIG. 2) may be provided, having one or more wire electrodes 3302 and a tissue removal bag 3304. The wire electrodes 3302 may be coupled to the tissue removal bag 3304 by embedding the wire electrodes 3302 into a film 3306 on an interior of the removal bag 3304. A tissue cutting effect may be initialized by applying power to the wire electrode 3302, causing the film 3306 to break down, whereby the wire electrode 3302 is released from the bag and a spark between the tissue and the wire electrode 3302 is initiated to achieve the tissue cutting effect.

Those skilled in the art will understand generally that initiation of the wire to begin the cutting effect results from a separation between the wire electrode 3302 and the tissue when power such as RF energy is applied, and that coating on the wire electrode or a film material in the bag 3304 or any other component may be suitable for achieving this effect.

In some embodiments, a separate means to pre-tension the tissue sample and an insulative layer between the wire electrode 3302 and the tissue are provided for this purpose. This layer may be a pressurized air layer, a non-conductive fluid layer, an insulating film or layer applied between the wire and tissue, which may serve the alternative function of applying the tension of the tissue sample, or could be achieved with the design of the bag, the wire attachment, and the pre-tension mechanism such that a gap results in the tissue wire/bag interface during operation. The desired wire set to be activated may have power such as RF energy applied and after sufficient power having a voltage is applied, the wire set may either be pulled to the surface of the tissue or may mechanically, electrically or with temperature break through the separation layer and begin the cutting effect. Generally stated, any easily electrically removable (or degradable) adhesive or retaining volume to hold the wire electrode in place may be provided, as illustrated in FIG. 33. Upon electrical input, the bare wire electrode 3302 will cut through the retaining medium (adhesive/retaining volume) or film 3306. This easy to degrade medium or film 3306 may also provide a pseudo air-gap, to promote initiation of the tissue cutting effect.

Turning now to FIG. 34, a return electrode 3420 that has is attached to the bag and contains extensions 3421 longitudinally down the bag side walls. These extensions 3421 are located in-between the active electrode channels 3422, and are electrically connected using a ring 3423 at the distal portion of the bag side walls. In the illustrated configuration, the wires 151 only cross over the return electrode 3420 at the ring 3423; those skilled in the art will therefore recognize that the return electrode 3420 should be isolated from the wires 151 at the ring 3423, such as by a film 802 as previously described herein. The isolation required to insulate the active electrode/wires 151 from the return electrode 3420 is reduced in the illustrated embodiment by the use of the extensions 3421. That is, in some embodiments, the device 102 or system 200 may include a plurality of electrically conductive elongated portions or extensions 3421 coupled to a base or ring portion 3421. In addition, this configuration provided the lowest observed impedance occurring at the beginning of the cut (e.g. near the bottom of the bag or ring 3421). As the wire 151 travels into the tissue, the impedance will slightly increase providing more energy to sustain the cut as the wire travels away from the return electrode 3420.

One additional advantage of the return electrode 3420 is that the bag assembly will more easily compress to a small diameter to aide in insertion through the incision site.

Figure 35:
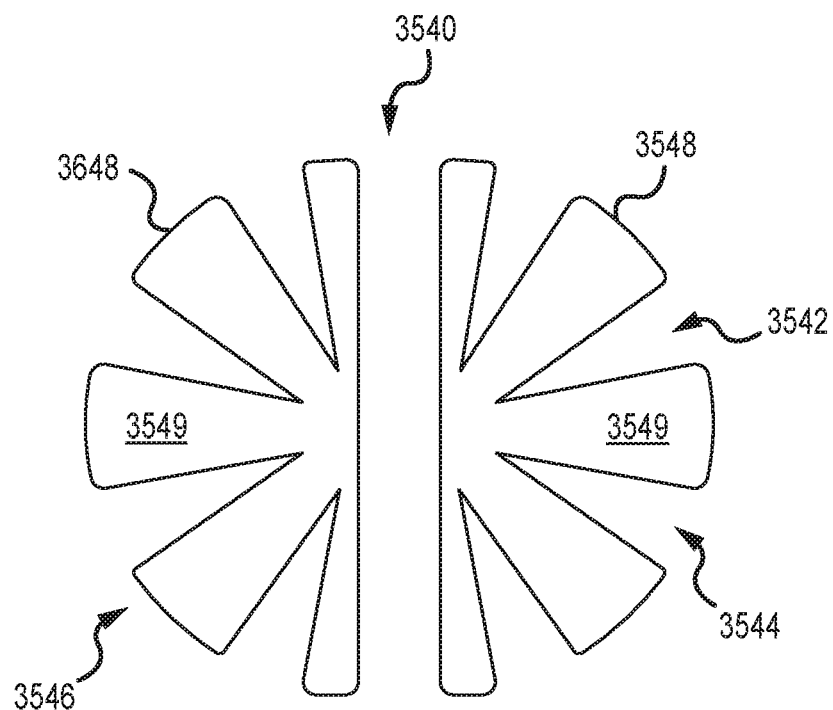
FIG. 35 illustrates a top view of a return electrode.

In some embodiments, and as is illustrated in FIG. 35, the return electrode 3540 may include areas for the return electrode 3540 to be folded or collapsed, to aid in insertion through the incision site. For example, the return electrode 3540 may be a dual return electrode 3540, having a first return portion 3544 and a second return portion 3546, which are attached to the inside surface of the distal portion of the bag. The portions 3544, 3546 may have recessed areas 3542 that allow the extensions 3548 to collapse, similar to an umbrella. At least a portion of the extensions 3548 may have a pie shape, or taper between a wide distal portion towards a narrow proximal portion, relative to a center of the return electrode 3540. In some embodiments, a first portion 3544 of the dual return electrode 3540 has about 5 extensions 3548, and a second portion 3546 of the dual return electrode 3540 has about 5 extensions 3548. In some embodiments, the first and second portions 3544, 3546 mirror one another.

The dual return electrode 3540 may be configured to collapse against the introducer allowing easier insertion, while providing a large surface area 3549 when the tissue is loaded and tension is applied to the bag. Those skilled in the art can see that the number of recessed areas 3542 and the ratio of return electrode surface area 3549 to recessed areas 3542 can be adjusted to ensure the surface area 3549 remains large enough to maintain lower return electrode heating during power activation, and ease of collapsing during insertion of the bag into the incision site.

Methods of making a return electrode such as those described herein may include bonding a return electrode and cable to the bag, or forming the electrode on the surface of the bag with a vapor deposition, spray coating or a conductive printing process. A deposition or conductive printing method may provide improved flexibility of the finished bag to allow easier insertion. Bonded return electrodes and return electrode cables may be made from flexible circuits bonded with adhesive, or may be integrated into the bag layers by heat sealing at the boundary of the cable and/or return electrode.

In some embodiments (not illustrated) tissue segments may be marked for identification through the use of power modulation of each wire or wire set, such as providing a different power setting or waveform so as to leave a characteristic desiccation layer or pattern as part of the segmentation cut. This different power setting or waveform may be a modulated higher frequency waveform that is combined with the fundamental waveform delivering the RF power to the tissue. As such, the primary function of controlling the RF power delivered to the tissue to perform the cut can be relatively unaffected by the modulated waveform by the use of an analog or digital low pass or band pass filter in the control system feedback loop. That is, the method 10000 may include adjusting a power setting so as to cause the wire to leave an identification pattern in the cut associated with each of wires 1-N. In some embodiments, the identification pattern may be different for each wire, or some wires may have the same identification pattern as others (e.g. some may simply identify a direction, or which wire was the first or last, etc.).

Figure 36:
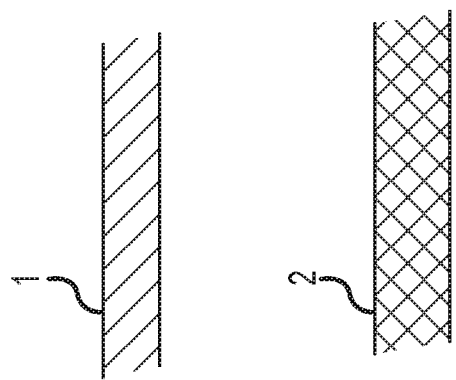
FIG. 36 depicts an electrode color coding means.

Turning now to FIG. 36, the electrodes/wires may have a color coded powder applied to the surfaces such that each electrode/wire has a different color, and the distal end of the tissue specimen becomes marked when the wires are pre-tensioned against the tissue specimen. For example, a first wire 1 may have a powder coating having the color A, and a second wire 2 may have a powder coating having the color B. The resulting markings on the tissue specimen may be used to recreate the orientation of pieces of the segmented tissue specimen.

Figure 37:
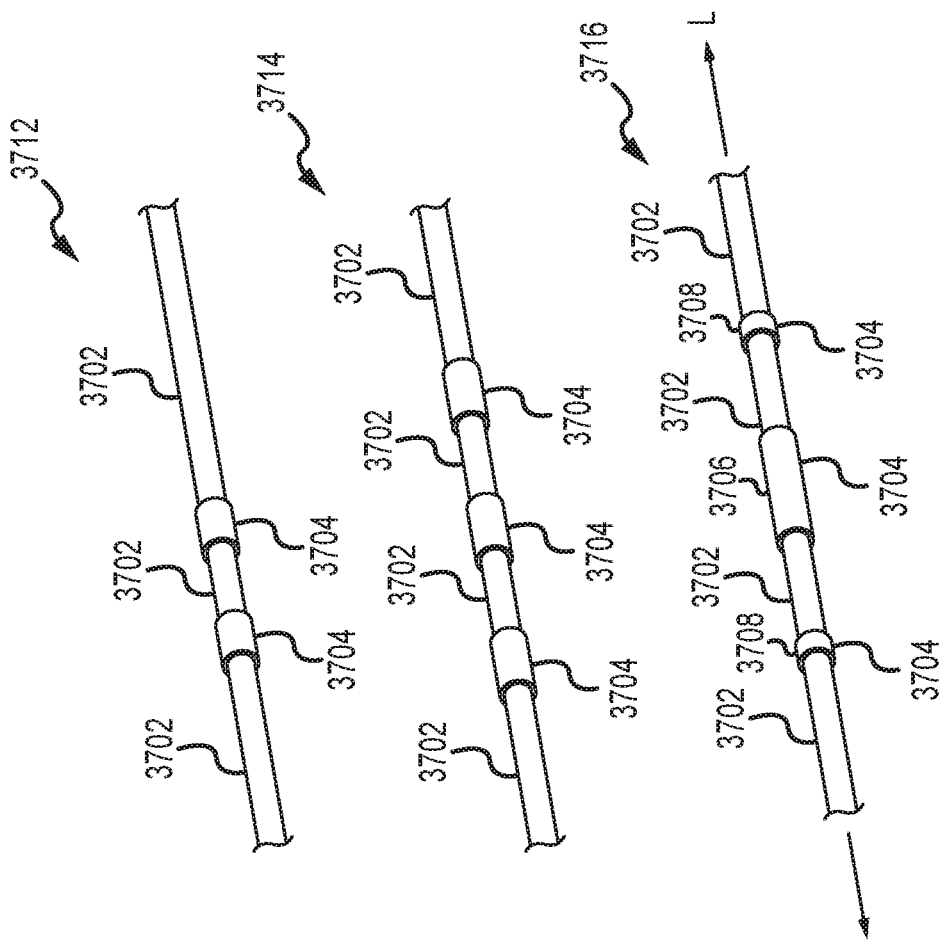
FIG. 37 depicts an electrode coding means.

With reference now to FIG. 37, in some embodiments, the electrodes or wires may be provided with insulation sections or highly conductive sections that provide a "signature" or orientation mark on the respective tissue cutting edge as the wire travels through the tissue specimen. For example, as illustrated in FIG. 37, a coating 3702 may be applied to a first active electrode 3712 to define an active electrode surface area. Within the active electrode surface area may be two bands of insulation material 3704 that are less conductive for the power or RF energy than the surrounding area. As a result, the current concentration is less at the interface of the tissue and the insulation material 3704. This results in a visual difference in the desiccation of the tissue specimen after the cut. The surface of the tissue will have lines created by these insulation bands 3704 that can be used to identify which tissue segment was cut by the first active electrode 3712. These bands 3704 may be repeated throughout the first active electrode 3712 to leave this pattern across the entire cutting plane.

With continued reference to FIG. 37, a second active electrode 3714 may have a plurality of bands of insulation material 3704, in a number that is different from that of the first active electrode 3712; a third active electrode 3716 may have a plurality of bands of insulation material 3704, in a number that is different from that of the first active electrode 3712 and the second active electrode 3714. More or fewer electrodes may be provided, having bands 3704 in any suitable pattern to distinguish the segment planes cut from each active electrode 3712, 3714, 3716 from the others.

In some embodiments, a first ring of material 1006 may have a longitudinal dimension that is different from a second ring of material 3708. In some embodiments, the first and second rings of material 1006, 3708 have a conductivity that is different from the rest of the coating 3702 on the electrode 3716. In some embodiments, the rings of material 1006, 3708 are more conductive than the rest of the coating 3702. In some embodiments, the rings of material 1006, 3708 are less conductive. In some embodiments, the first ring 1006 has an overall surface area that is different from an overall surface area of the second ring 3708.

In some embodiments, the length of the insulation material 3704, the number of bands for a given length, and/or the spacing of the bands 3704 may be modulated so as to sufficiently identify cuts made by the respective active electrodes. In some embodiments, the bands may, instead of an insulating material, have a highly conductive material that conducts current at a higher rate than the normal coating 3702 on the active electrode surface. That is, generally speaking, the identification bands 3704 may be more or less conductive than the coating 3702.

In a tissue segmentation method, a surgeon may pre-mark the tissue specimen during loading or after the bag is exteriorized.

In some embodiments, an ink stamp may be provided on the proximal tissue specimen surface when the bag is exteriorized, can be an ink stamp marked during loading, or can be dyes injected into regions of interest into the specimen prior to cutting.

Returning briefly to FIG. 1, in some embodiments, a removal bag 161 that contains multiple sets of active electrode wires 153, 155, 157, 159 may be provided. The bag 161 and active electrode wires 153, 155, 157, 159 may be designed to have a specific sequence of activations of the wires 153, 155, 157, 159 to avoid interference between a first wire set and a second wire set. To prevent a user from performing the power or RF energy activations in an incorrect sequence, connectors may be color coded or shaped to correspond with the tensioning mechanism connections. Relatedly, the tensioning mechanisms may have a predefined sequence of operation that the user or controller selects.

The receptacle of the tensioning mechanism designed to connect to the active electrode wire connector may have a color or shape associated with it. The corresponding active electrode wire connector may have the same color or shape allowing the user to connect the like colors or like shapes together ensuring that the proper sequence will be maintained. In some embodiments, a method of ensuring the proper connection sequence is maintained includes providing each of the tensioning rod receptacles with a unique shape such that it will accept only the corresponding active electrode wire connector having a unique mating shape. Alternatively the respective wires may have increasing amounts of coating impedance from one wire to the next. Energy may then be applied to all of the wires, however the coating variation will force the wires to fire or cut sequentially rather than simultaneously.

In some embodiments, the spring 676 is used as a direct electrical conductor to apply the power or RF energy to the wires, and insulation coatings may be applied to the surface of the spring to control when power application can be enabled. Locations of this insulation material can be applied so that when the spring is in the fully extended, or pre-tension, position an insulation coating is located at the contact point of the power or RF energy to spring electrical interface. When the device is pre-tensioned and the springs advance to apply the tension on the tissue sample, the insulation coating advances to the coil of the spring and an electrically conductive portion of the spring is now in contact with the RF to spring electrical interface. An additional insulation coating can be applied at the location in which the spring completes its cut so that power or RF energy is terminated.

Some organs for specimen cutting include but are not limited to: uterus, ovary, kidney, colon, spleen, liver, gallbladder, and lung. For some organs, the minimally invasive access and excision of the specimen may benefit from a noncircular distal instrument end such as in video assisted thorascopic surgical procedures (VATS) for lung. In this case the incision may be much wider than it can be tall because of spacing between the ribs. In this case it may be advantageous for the segmentation instrument to be non-circular to accommodate or optimize use of the space available. For example, more than two tensioning mechanisms may be generally arranged in a line within an oblong oval shaped instrument end. The shape of the bag may also be modified to better align the electrode wire assemblies with the tissue specimen shape and size. This may also require a different number of active electrode assemblies or different active electrode wire lengths.

In some procedures, it is likely that the specimen may contain a staple line or clip remaining from an excision. This is particularly common in lung and colon procedures. It may be desirable to utilize a stronger wire that is more likely to penetrate the staple line during the cut without breaking the active electrode. This may be accomplished through use of a stronger material, titanium as an example. It may also be accomplished through the use of a stranded wire or a larger diameter wire than would be typically used.

As technology advances and drives more minimally invasive procedures, the incision sizes commonly used in surgery continues to reduce. As these sizes become smaller, the need to remove tissue specimens that are routinely removed with currently available methods becomes more of a challenge. In addition to the organs previously mentioned that are candidates for specimen cutting for removal, smaller portions of these organs and small masses that are not considered necessary for tissue segmentation prior to removal will become candidates for removal in the future. An example could be an appendix or gall bladder that can easily be removed through a 5 mm trocar today, but as the use of 3 mm devices or smaller become more commonplace, segmentation of the device will become an obvious solution for removal.

In some embodiments, a crimp connector including a resistor, optical feedback or RFID that that has corresponding circuit in the tissue segmentation device 100 or the controller 108, 708 may be provided that may perform an identification method. In some embodiments, the identification method includes: (a) identify to the controller a particular length of exposure, to notify the controller of proper power setting (controller can adjust if different length exposures are used); and/or (b) identify to the controller the type of bag being used. The identification method may include distinguishing or identifying the use of a small uterine bag, a large uterine bag, a lung bag, a colon bag, a kidney bag, etc. The bag identification method may be achieved using the resistor value, optical signature or RFID as an index for a lookup table pre-programmed into the datastore 110 of the controller 108 or device 102. The index may point to stored parameters that update the parameters for the particular type of bag or the specific active electrode wire set connected to the connector containing the resistor. In some embodiments, the information programmed in the optical encryption or in the RFID contents is used to update the parameters with the information passed to the controller 108. This information may, in some embodiments, include the sequence number so that the controller is configured to apply RF energy in the correct sequence for any connection made by the user or may contain impedance or other performance information that can be used as an adjustment to parameters for that particular active electrode wire set.

Figure 38:
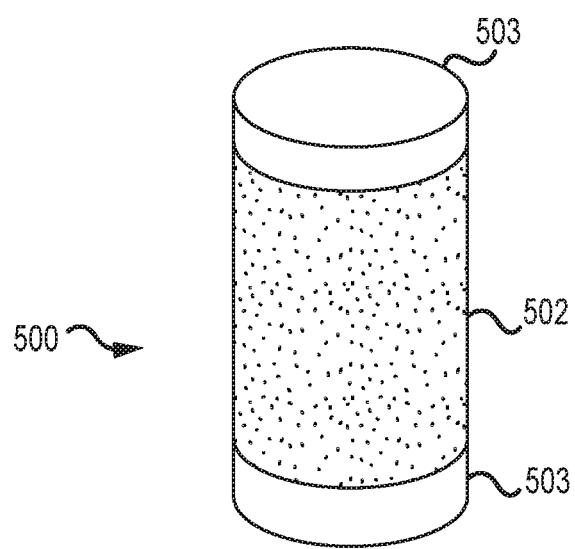
FIG. 38 illustrates a resistor element.
Figure 39:
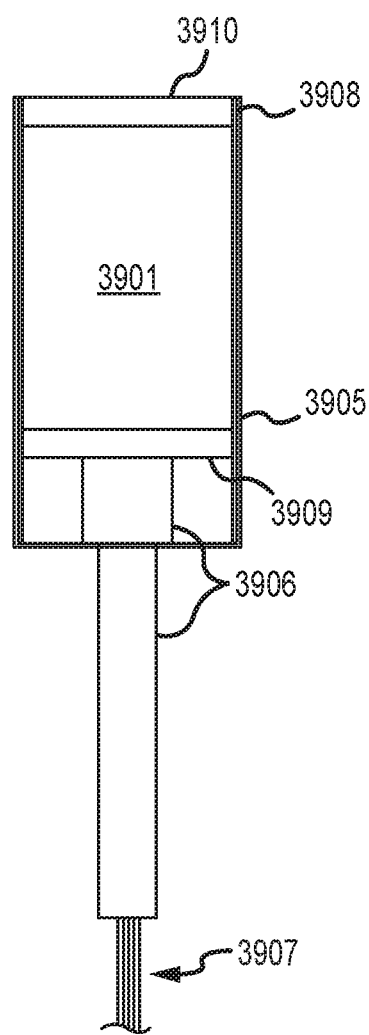
FIG. 39 illustrates a crimp connector with resistor.

Turning now to FIGS. 38 and 39, some embodiments may include a resistor 3800, 3901 integrated into the crimp connector 3905 to provide a resistive value that can be used to provide information regarding the active electrode wire set. FIG. 38 illustrates an example of the resistor 3801 with a resistive element 3802 and contacts or end caps 3803. The resistive element 3802 provides the desired resistance and can be a carbon, film or wire wound material. The contacts or end caps 3803 are composed of a highly conductive material, such as tinned copper or aluminum, and are attached to the resistive element such that the desired resistance provided by resistive element 3802 can be electrically measured between the two contacts 3803.

FIG. 39 illustrates an embodiment that integrates a resistor 3901 into the crimp connector 3905 and crimp ferrule 3906. The crimp ferrule 3906 contains the termination of the common active electrode wires 3907 intended to be mechanically and electrically coupled. These wires 3907 fit through a lumen in crimp ferrule 3906 and are crimped to secure the wires mechanically, as well as to provide electrical coupling between the active electrode wires 3907 and the crimp ferrule 3905. Those skilled in the art will recognize that these wires can be welded, bonded or captured within the crimp ferrule with means other than crimping as long as the method provides an electrical coupling from the wires 3907 to the crimp ferrule 3906.

In some embodiments, the crimp ferrule 3906 has a stepped feature at a proximal end such that the crimp ferrule 3906 is fixed in or relative to the crimp connector 3905. This provides mechanical and electrical coupling between the crimp ferrule 3906 and the crimp connector 3905. The resistor 3901 may be placed within the crimp connector 3905 such that the distal end cap 3909 is electrically in contact with the end crimp ferrule 3906. This provides an electrical coupling from the outer surface of the crimp connector 3905 to one end of the resistor 3901.

Of note, the proximal end cap 3910 is electrically isolated from the crimp connector 3905. This is achieved by creating an isolation barrier 3908 that may be provided by, for example, an insulative film between the resistor 3901 body and the internal surface of the crimp connector 3901. This may be an insulative film or coating applied to the top portion of the inside surface of the crimp connector, an insulative film or coating applied to the sides of the end caps 503, physical separation provided with end caps that have a smaller diameter than the resistive element or by placing the resistor within an insulation component that exposes only the center of the top end cap prior to inserting into the crimp connector.

In some embodiments, a resistance value of resistor 3901 can be electrically measured between the proximal end cap 3910 and the outer surface of the crimp connector 3905.

With continued reference to FIG. 39, the component within the tensioning instrument that interfaces to the crimp connector has a center axial component (not shown) that is electrically isolated from the outer portion. The axial component may have a spring or other means of ensuring contact when the crimp connector 505 is placed into the tensioning instrument. The resistance of the resistor 501 is then measured by applying a known voltage or current between the center axial component and the outer portion contacting the remaining surface of the crimp connector 505 and measuring the resulting other one of current, or voltage.

Figure 40:
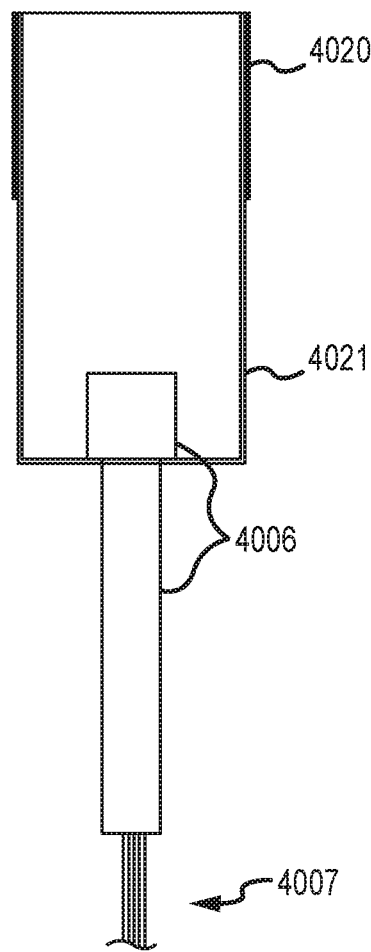
FIG. 40 illustrates a crimp connector with a resistor ring.

Turning now to FIG. 40, in some embodiments, a resistive element 4020 may include a coating or ring of material at the proximal end of the crimp connector 4021. This resistive element 4020 can be applied by spraying, vapor deposition, machined and bonded in place or with other means. As previously described with reference to FIG. 39, an electrical coupling from the wires 4007 to the crimp ferrule 4006 may be provided.

Here, the component (not shown) within the tensioning instrument that interfaces to the crimp connector 4021 has a separate contact point on the inside mating surface at the proximal end and must be electrically isolated from the lower portion. The resistance of the resistor 4020 is then measured by applying a known voltage, or current, between the proximal contact point and the outer portion which contacts the remaining surface of the crimp connector and measuring the resulting other one of current, or voltage.

Measuring the resistance can be achieved using an analog circuit, such as an op amp or other means to apply the reference voltage or current and an A/D converter to measure the resulting electrical parameter. This circuit can be located within the tensioning instrument or can be located within the controller. Separate electrical traces may be provided to each side of the resistor 501, 4020 and may be accomplished by applying a thin conductive trace on the surface of the spring isolated from the spring with an isolation film. The conductive trace may be routed to either the axial contact (see FIG. 39), or the proximal contact (see FIG. 40) by a termination block that connects the tensioning rod to the spring at the distal end of the device. At the proximal end of the spring, separate spring contacts located at the coil of the spring align with the conductive trace and the remaining spring surface.

In some embodiments, the electrical traces are provided by using separate contact areas on outer surface of the termination block that are routed to either the axial contact illustrated in FIG. 39 or the proximal contact illustrated in FIG. 40. When the crimp connectors 4006 are attached, the instrument is in the fully extended position. In this position, spring contacts located in the housing of the instrument can be aligned with the contact areas of the termination block to make the resistor measurement prior to applying pre-tension of the instrument. In some embodiments, the resistor value measured for each crimp connector is stored in a datastore, which may be located on either the tensioning instrument or in the controller itself.

Returning now to FIG. 1, in some embodiments, a system 100 having a bag 161 may be provided. The bag 161 may have a plurality of active electrode sets 153, 155, 157, 159, each having a resistor (not illustrated). The first electrode set 153 may have a resistor having a first resistance, such as 100 ohms. The second electrode set 155 may have a resistor having a second resistance, such as 200 ohms, the third electrode set 157 may have a resistor having a third resistance, such as 300 ohms, and the fourth electrode set 159 may have a resistor having a fourth resistance, such as 400 ohms. The controller 108, 708 may detect each resistor value and apply RF activation to the electrode sets 153, 155, 157, 159 according to a particular sequence. In some embodiments, power is applied to the first electrode set 153 first, the second electrode set 155 second, and so on, regardless of which tensioning mechanism in which they were connected.

A second type of bag also with 4 active electrode wire sets may contain 1100 ohm, 1200 ohm, 1300 ohm and 1400 ohm resistors respectively. Using this approach, those skilled in the art can see that many number of bag types with varying combinations can be supported with a controller that contains the lookup table information.

In some embodiments, the system is configured to perform a tissue to return interface impedance check. Those skilled in the art will understand that it is essential to have good contact between the tissue specimen and return electrode of the device to maintain low temperature cutting. One method to ensure this contact is described in the open circuit check previously described herein. Another method is to utilize two sections of the return electrode in a manner similar to methods known in the art. Using known methods, a small interrogation signal is applied by the electrosurgical generator between two sections of the return electrode. This signal is used by many currently available generators to calculate the impedance between the two return electrode sections. As the tissue makes contact with the two sections simultaneously, the impedance of the tissue between the sections will provide a low resistance. This is continuously monitored by the generator, and if the tissue loses contact with the return electrode, the impedance change can be observed and an alarm condition can be initiated so that the user can address the situation.

In some embodiments, a movement/position indicator is provided. Graduated markings on the surface of the spring in conjunction with an optical encoder or transceiver pair allows relative measurement of spring travel. A rate of electrode/wire travel may be detected by integrating over a time period a length of travel. The length of travel may be determined by counting markings from a pre-tension location. A stopped travel condition may be identified and indicated by a lower than acceptable rate of travel.

Figure 41:
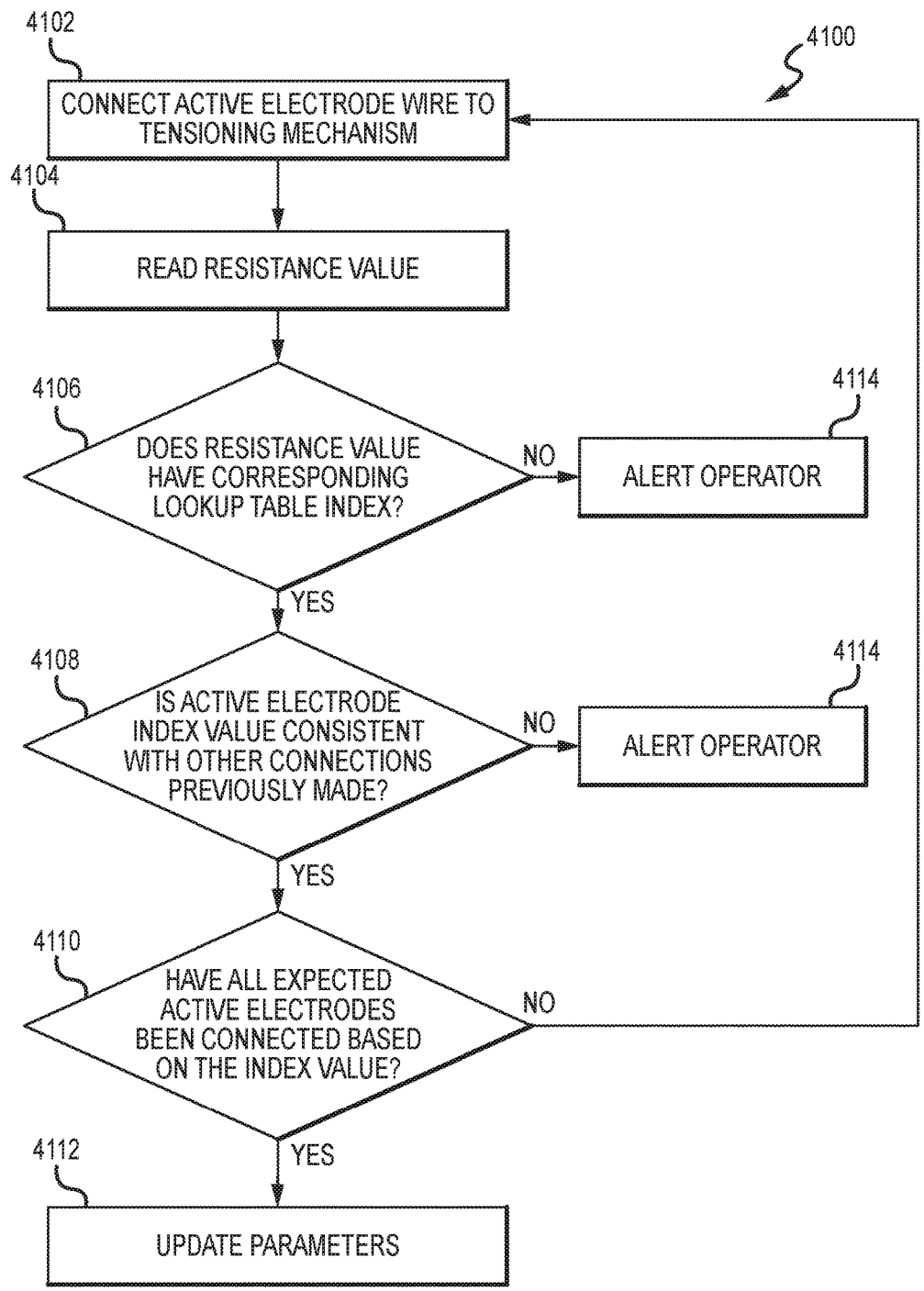
FIG. 41 illustrates a flowchart of an active electrode connector recognition method.

Turning now to FIG. 41, a method 4100 of active electrode connector recognition is disclosed as illustrated. The method 4100 may include one or more of (a) connecting 4102 active electrode to tensioning mechanism, (b) reading 4104 a resistance value, (c) determining 4106 if the resistance value has a corresponding lookup table index, (d) determining 4108 if the active electrode index value is consistent with other connections previously made, (e) determining 4110 if all expected active electrodes have been connected based on the index value, (f) updating parameters 4112, and (g) alerting the operator 4114.

Applicant has determined that as the tissue is segmented with multiple power or RF energy activations of the system 100, the structure of the tissue is weakened and the tissue "flows" or changes shape, which can cause irregular or non-repeatable segment sizes to occur. A method of reducing this tissue flow may be provided, and may include holding the tissue during segmentation to contain the flow.

Figure 43:
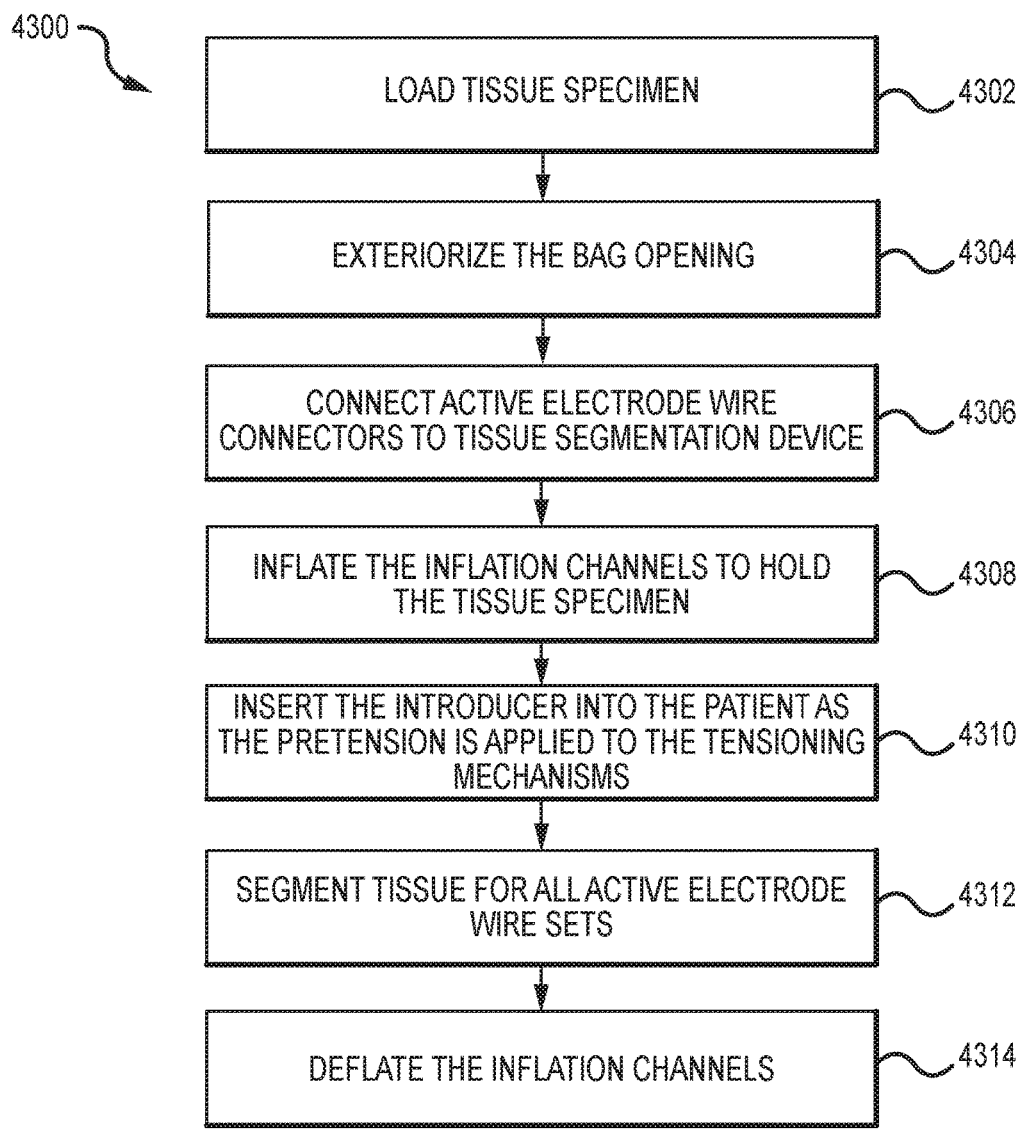
FIG. 43 illustrates a method of using an inflatable tissue removal bag.

For example, and with reference to FIG. 42 and FIG. 43, inflation may be provided at specific areas to hold the tissue in place.

FIG. 42 illustrates a top view and a side view of a removal bag 4200 having four separate active electrode wire sets 4202. The bag 4200 also includes inflatable channels 4204 that run parallel to the wire sets and are located on the bag surface in-between the wires. These inflatable channels 4204 are deflated when the tissue specimen is loaded and inflated after the bag 4200 is exteriorized and connected to the electrosurgical device 102. The inflation causes the inflation channels 4204 on the bag 4200 to extend to contact a surface of the tissue specimen and provide support around the circumference of the bag 4200. The tensioning mechanisms are then pre-tensioned to start the segmentation process. The location of the inflation channels 4204 may be selected to allow the active wire electrodes to contact the tissue and perform the cut without interfering with the channels 4204. The location of the inflation channels 4204 may also support the tissue during the entire cut, thereby reducing tissue "flow". After the cut is completed, the inflation channels 4204 may be deflated to allow specimen removal. This inflation and deflation can be performed with a syringe. In some embodiments, the controller 108 or a second device may be configured to regulate the pressure automatically. Feedback on successful pressure application may be provided by observing an acceptable range of volume applied for inflation with a syringe and the resistance of increasing the pressure manually with an automated syringe application, or with pressure sensors in an automated pressure delivery device.

FIG. 43 illustrates a method 4300 of using a tissue removal bag for tissue support. The method 4300 may include one or more of (a) loading 4302 a tissue specimen, (b) exteriorizing 4304 the bag opening, (c) connecting 4306 active electrode wire connectors to tissue segmentation device, (d) inflating 4308 the inflation channels to hold the tissue specimen, (e) inserting 4310 the introducer into the patient as the pretension is applied to the tensioning mechanism(s), (f) segmenting tissue 4312 for all active electrode wire sets, and (g) deflating 4314 the inflation channels.

Returning now to FIG. 41, in some embodiments, after successful completion of active electrode recognition, the instrument or controller may update the parameters as indicated in FIG. 41. As part of this parameter update, the sequence of activation may be included. As such, the instrument or controller may automatically select the active electrode wire corresponding to the first pull to apply the power or RF energy. In addition, the instrument or controller may also select the pre-tension mechanism related to the active electrode wire corresponding to the first pull. A solenoid or other electromechanical means to lock out the pre-tension mechanism until an enable signal is applied from the instrument or controller may provide the ability for the instrument or controller to select the pre-tension mechanism. The pre-tension mechanism of the first active electrode and/or the second active electrode may be desired to be enabled at the same time so as to assist in holding the tissue specimen before and/or during the cut.

Some methods and/or systems improve the reliability of the cut by pre-treating the tissue sample prior to cutting, such as by applying cryo to freeze the tissue. This may provide a more rigid specimen, and may reduce the thermal result of the cutting. Some methods include injecting a fixation material into the tissue specimen, which increases the rigidity of the specimen.

In some embodiments, a tensioning mechanism may include a constant force spring 702 and/or other mechanisms such as a pulley system, a cable drive or winch system, non-linear springs, linear drive with rotational coupling such as gears or contact coupling, linear drive with magnetic coupling, linear drive with manual control, and/or, as previously described, an electromechanical drive, such as a servo or stepper motor drive or linear actuator.

In some embodiments, a method of preparing or examining a tissue specimen is provided. One method for marking and reassembling the tissue specimen for later pathology involves the surgeon marking the margin or area of interest for later pathology prior to or just after placing the specimen in the bag. The surgeon can then segment the tissue and remove the pieces from the bag. Once removed, the specimens can be reassembled or the marked pieces may be identified and examined for pathologic assessment. The marked specimens may be identified through visual examination or may contain a fluorescing or similar chemical marker to enable the user to identify the segments using a fluorescing light.

Figure 44:
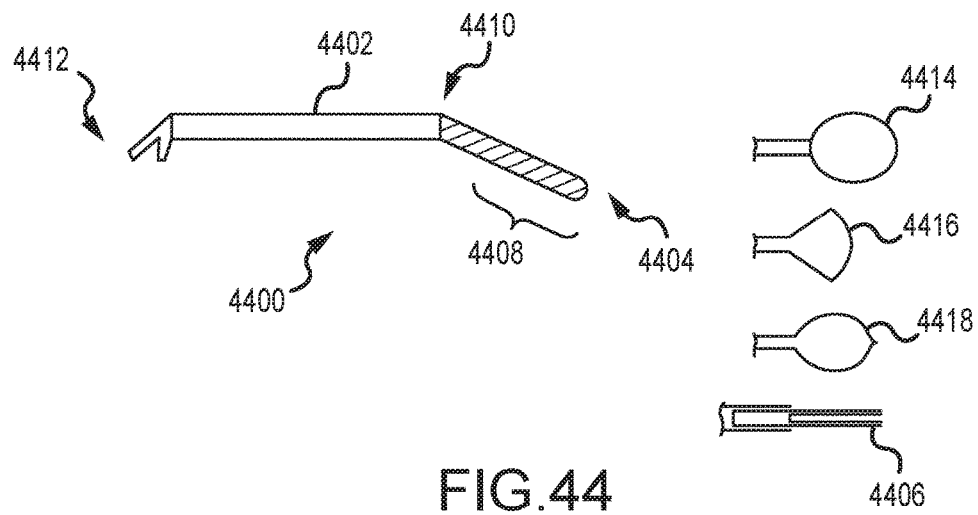
FIG. 44 illustrates several views of a marking instrument.

Turning now to FIG. 44, a specialized marking tool 4400 may be provided in some embodiments, and may be utilized by the surgeon to mark a specimen margin or area of interest prior to segmentation. This marking tool 4400 may include a shaft 4402 configured to fit through a laparoscopic opening or trocar. In some embodiments, the shaft 4402 of the marking tool 4400 has a small diameter of between 2 and 20 millimeters, although those skilled in the art will understand that other sizes may be suitable. The marking tool 4400 may include marking ink residing on a surface of a distal end 4404 of the marking tool 4400. In some embodiments, when placing the marking tool 4400 into a patient cavity, a sheath 4406 may be used to cover the ink containing distal end 4404, which can then be pulled back or withdrawn by the user to expose the inked portion of the tool 4400. The length of the exposure 4408 and/or distal end 4404 can be determined by the user based on how far the sheath 4406 is withdrawn. In some embodiments, the ink may only be released by the user such that it is on the marking end of the instrument only after the instrument has been placed in the patient's body.

In some embodiments, the distal end 4404 has a relatively long inked exposure 4408, such as up to between about 6 and 8 inches (between about 15.24 and about 20.32 centimeters) in length for marking a large surface of the specimen quickly. In some embodiments, the entire distal end 4404 may have an exposure 4408. In some embodiments, the exposure 4408 is less than the entirety of the distal end 4404.

Alternatively, in some embodiments, a relatively small exposure 4408 may be provided, so as to control the placement of ink in a more refined or selective area. Those skilled in the art will understand that the length of the exposure 4408 may be adjusted or selected based on a number of factors, including, but not limited to, specimen size, patient size, surgical cavity size, specimen location, and/or other factors. In some embodiments, the marking tool 4400 has an articulating link 4410, to allow articulation of a distal end 4404 relative to a proximal end 4412, to facilitate specimen marking.

In some embodiments, the specialized marking tool 4400 may have a means for expanding a diameter of the distal end 4404 once inserted into the patient, and decreasing the diameter prior to removal from the patient, and in some embodiments back to the original diameter prior to removal from the body. In some embodiments, an inflatable balloon 4414 that contains the ink on its outer surface may be provided. The user may inflate the balloon 4414, mark the area of interest on the specimen, deflate the balloon 4414, and then remove the marking tool 4400 from the body. The balloon 4414 may be contained within a shaft 4402 of the marking tool 4400 and extended from a distal end of the shaft 4402 prior to inflation of the balloon 4414. The ink may be present on the expanding member prior to insertion into the patient or may reside in a small pouch within the instrument whereby the user expands the marker and then breaks open or releases the ink so it can then be applied by the expanded member.

Continuing with FIG. 44, in some embodiments, the distal end may be configured to expand within the patient using a fan 4416 or leaf spring-like expansion mechanism 4418 holding an ink pad. In some embodiments, a self-expanding material such as a sponge, or a material that expands upon exposure to water or a liquid, any memory-retaining material, or similar means may be provided to enable expansion after insertion in a patient. That is, an expandable marking end 4414, 4416, 4418 may be provided, which may be minimized before removal from the patient, such as by retracting the expandable marking end 4414, 4416, 4418 back into the instrument shaft 4402, or extending the sheath 4406 back over the marking end. Those skilled in the art will readily envision any number of actuating mechanisms for achieving this functionality.

Figure 45:
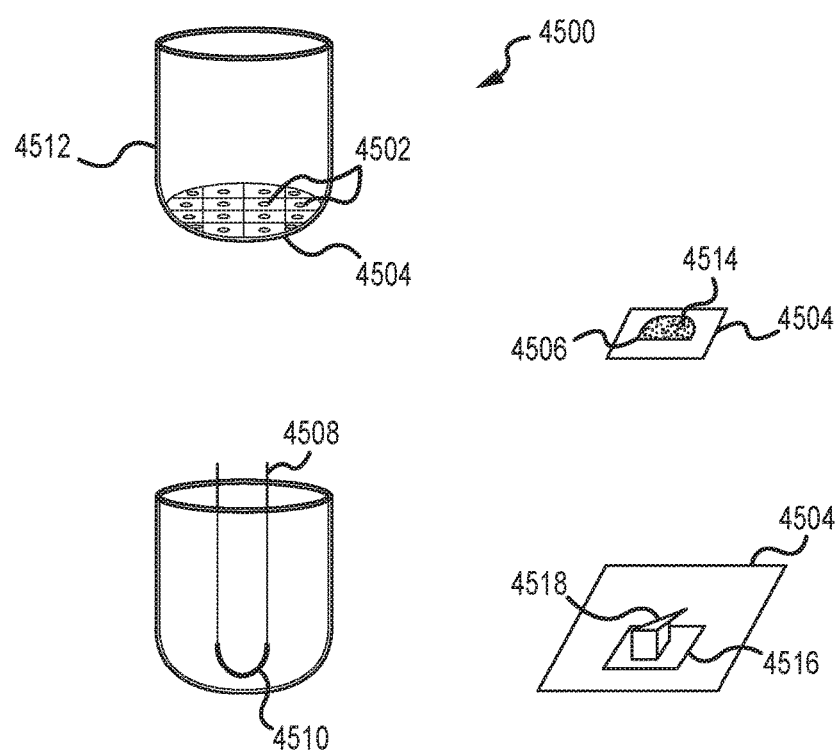
FIG. 45 illustrates several views of a tissue removal bag having marking features.

Turning now to FIG. 45 a bag 4500 with marking features is now discussed in further detail. Since a low temperature cutting approach creates very clean cuts with minimal damage to the tissue, the segmentation approach may be used on tissue that will require subsequent pathologic assessment such as in cancer surgeries. As has been described earlier, inks or markers may be used to help identify the specimen pieces when in the bag or once removed from the bag. Additional approaches may be used to help facilitate pathology.

For example, and as illustrated in FIG. 45, a tissue removal bag 4500 may be provided, having different color markers or ink 4502 for each anticipated tissue segment by housing the ink on a return portion 4504 of the bag 4500. The ink 4502 may be heat sensitive ink (or small pouch that opens with sufficient heat and releases the ink) or similar that is released when the electrodes or wires are activated to ensure the ink 4502 is placed properly onto the resulting segments. In some embodiments, one or more of the electrodes or wires 4508 may have a colored material 4510 integrated into them that stays behind on the tissue during cutting, for example using a low temperature material that melts off the electrodes or wires 4508 onto the tissue.

In some embodiments, the bag 4500 may be manufactured with the ink 4502 in one or more relatively small ink pouches 4506 that are attached to the bag 4500 during manufacturing. Alternatively, the ink pouch(es) 4506 may be empty and built into the bag 4500 with the ink injected into the pouches 4506 by the surgeon before or during use through a channel opening on a distal end of the bag. This has the advantage of allowing the surgeon to select what ink or marker he or she prefers. In some embodiments, one or more ink pouches 4506 may be attached to a return pad 4504 of the bag 4500. In some embodiments, one or more ink pouches 4506 may be attached to a flexible container 4512 of the bag 4500. In some embodiments, a plurality of ink pouches 4506 are attached to both the return pad 4504 and the flexible container 4512.

Figure 46:
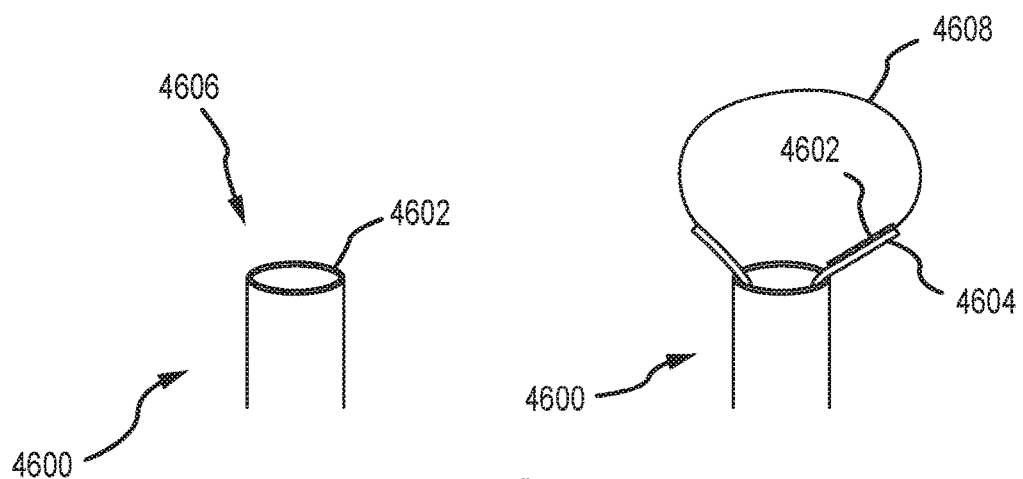
FIG. 46 illustrates two perspective views of ink marking components.

Turning now to FIG. 46, in some embodiments, a segmentation instrument may be provided with a distal end 4600. The distal end 4600 may include ink 4602 attached to or coated on one or more expansion petals 4604 that cause the wire/electrode 4608 to expand, or other segmentation instrument features. In some embodiments, the distal end 4600 of the segmentation instrument may have ink 4602 located on one or more distal surfaces 4606 of a tube and/or one or more petals 4604 intended for contact with the tissue. Once the segmentation instrument 102 (see e.g. FIG. 1) is pre-tensioned, the specimen is brought into contact with the inked features 4604, 4606.

In some embodiments, the clinician may apply markers after the segmentation but prior to removal of the segments from the bag. Marking of the samples may be done with a surgical marker, ink 2314 (see e.g. FIG. 45), or a physically attached tag, clip, or RFID tag on the sample segment ends nearest the exteriorized bag opening. This allows a pathologist to reorient the sample segments once they are brought from the operating room. These markers may also be integrated into the bag.

As illustrated in FIG. 45, one or more RFID tags 2316 may be attached to or removably attached to the bottom of the bag 2300 on one or more of the return portions 2304 (defined by the pattern created by the electrode(s)/wire(s) prior to cutting). One or more barbs 2318 or any other means may be provided to cause the RFID tag(s) 2316 to attach to the tissue segments.

In some embodiments, the surgeon may mark the surface or portion of the specimen that needs pathologic assessment for margin, prior to or just after loading the specimen in the bag. This may be done with a marker or ink. The specimen can then be segmented, and removed from the patient. The pathologist then knows to find the segments that contain this surface and to assess for margin or any cancer cells that might be found on the surface.

Some embodiments include using imaging recognition, including but not limited to, a digital camera and/or ultrasound to image the specimen prior to segmenting, removing, or during removal of the segments from the bag. Digital image processing may then be used to reorient the segments in order to recreate the specimen using software designed to recognize features on the segments and reorient them in the proper location relative to each other. A low cost digital camera with digital imaging software may likewise provide an inexpensive and automated means for reorienting segments into their original orientation. This may be done with or without prior marking of the specimen before imaging.

Some embodiments include reconstructing the excised tissue specimen after removal, and to use a common imaging means, such as fluoroscopy, on the segmented tissue specimen to determine the location of the area of interest within the tissue specimen. This may also be used to perform additional diagnostics on the specimen to determine the scope of pathological assessment required or to guide the remaining surgical intervention required.

In some embodiments, markers may be used to identify a known tumor or structure of interest either before surgery or intraoperatively. The bag may also have markers or fiducials that can be imaged or scanned as part of the loaded bag in order to show the orientation of the specimen (and tumor) relative to the bag. By tracking the specimen segments as they are segmented and removed the known original location of the tumor, and thus the segments that contain the tumor, may be determined. This provides further information to the pathologist during their evaluation.

In some embodiments, the wires may be used as the fiducials prior to the cutting. To further enhance their location an ultrasound sensitive or radio opaque coating may be applied to a small portion of the wire. Using commonly available image capturing approaches the location of the wires, their projected path of travel, and the location of the tumor can all be determined and analyzed. This information can then guide the pathologist on which segments have particular interest for pathologic assessment. The surgeon or operating room staff may place additional markers on the tissue segments prior to leaving the operating room using this image information to identify segments of interest. The images from the specimen taken with the wires or bag fiducials that estimate the segments can also be accessed during pathology to show assembled segment structures (i.e. vasculature, tumor, etc.) that can be compared to the segments themselves.

In some embodiments, a method of cancerous tissue handling is provided. During removal of segmented tissue that is known or suspected of being cancerous from the segmentation bag, extra care may be desired to ensure that fluids or tissues do not spill and thereby cause specimen site seeding. Various methods such as an absorbent pad 4708 may be used to limit spilling of tissues. The pad 4708 may have a hole in it that is placed over, under or around the exteriorized bag opening 4710, to absorb any fluids that may spill (see e.g. FIG. 47).

Figure 47:
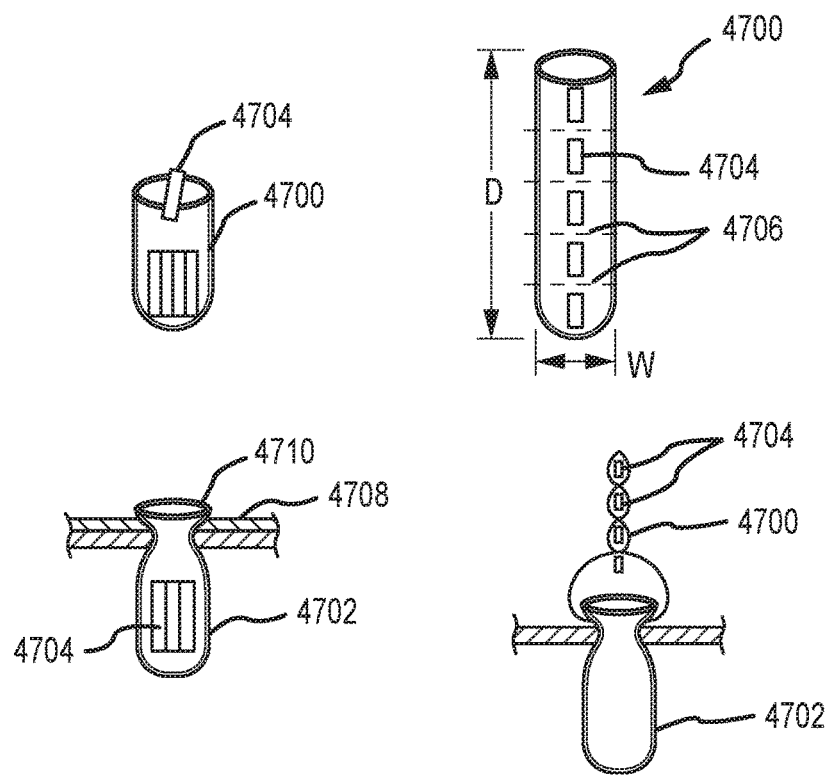
FIG. 47 illustrates several views of a tissue removal bag.

With reference to FIG. 47, a separate bag 4700 may be provided to capture tissue segments 4704 as they are exteriorized from the patient. The separate bag 4700 may be twisted about each individual segment 4704 as the segment 4704 is removed from the patient and/or a primary bag 4702. In some embodiments, the separate bag 4700 may be twisted about the primary bag 4702 as the primary bag 4702 is removed with one or more tissue segments 4704.

In some embodiments, and as illustrated in FIG. 47, an extendable or elongated bag 4700 may be provided to capture the segments 4704 as they are removed from the patient. For example, an elongated bag 4700 may be oversized in a depth D relative to a maximum width W that is suitable for a particular tissue to be removed. For example, where a standard bag for a uterus may have a first width W and a first depth D, the elongated bag 4700 may have a first width W that is unchanged from the standard bag, and a second depth D that is greater than the first depth D, and in some embodiments, the second depth D may be several times the first depth D so as to ensure sufficient material is provided for capturing the tissue segments 4704.

As illustrated, the elongated bag 4700 may have a flexible container that is twistable at one or more twisting regions 4706 so that individual segments 4704 may be captured individually. For example a segment 4704 may be captured, the bag 4700 may be twisted to contain the segment 4704, and the process repeated with another segment 4704 placed in the bag 4700 (note this twisting process applies to the secondary bag 4700). Those skilled in the art will understand that even where an elongated or secondary bag 4700, 4700 is provided and enables a user to twist tissue segments 4704 to separate them, the user need not necessary perform this step, optionally capturing all tissue segments 4704 in a single cavity. Those skilled in the art will also understand that the user may optionally seal, tie, clamp, or otherwise fasten the twisted regions 4706 so as to semi-permanently separate the individual segments 4704 from one another. In some embodiments, the film 802 previously described herein may provide a semi-permanent sealing feature between the cavities formed about the segments 4704.

With novel dyes being created for use in identifying cancerous cells in situ, these dyes may be placed in the bag, so once the specimen is segmented, the surgeon can look at the bag to see if any signs of cancer are present in the sample. For example, in a method similar to fluorescence-guided surgery using a cancer cell "homing device" and imaging agent created by a Purdue University researcher, novel imaging agents may be injected prior to surgery, and could be seen in specimen upon removal. Relatedly, a similar imaging agent may be placed in the bag (bag wall, small pouches on bag return, or injected into bag by surgeon with a syringe or similar instrument prior to or after removing segments from bag) in a manner substantially as previously described herein with reference to FIGS. 41 through 46.

Figure 48:
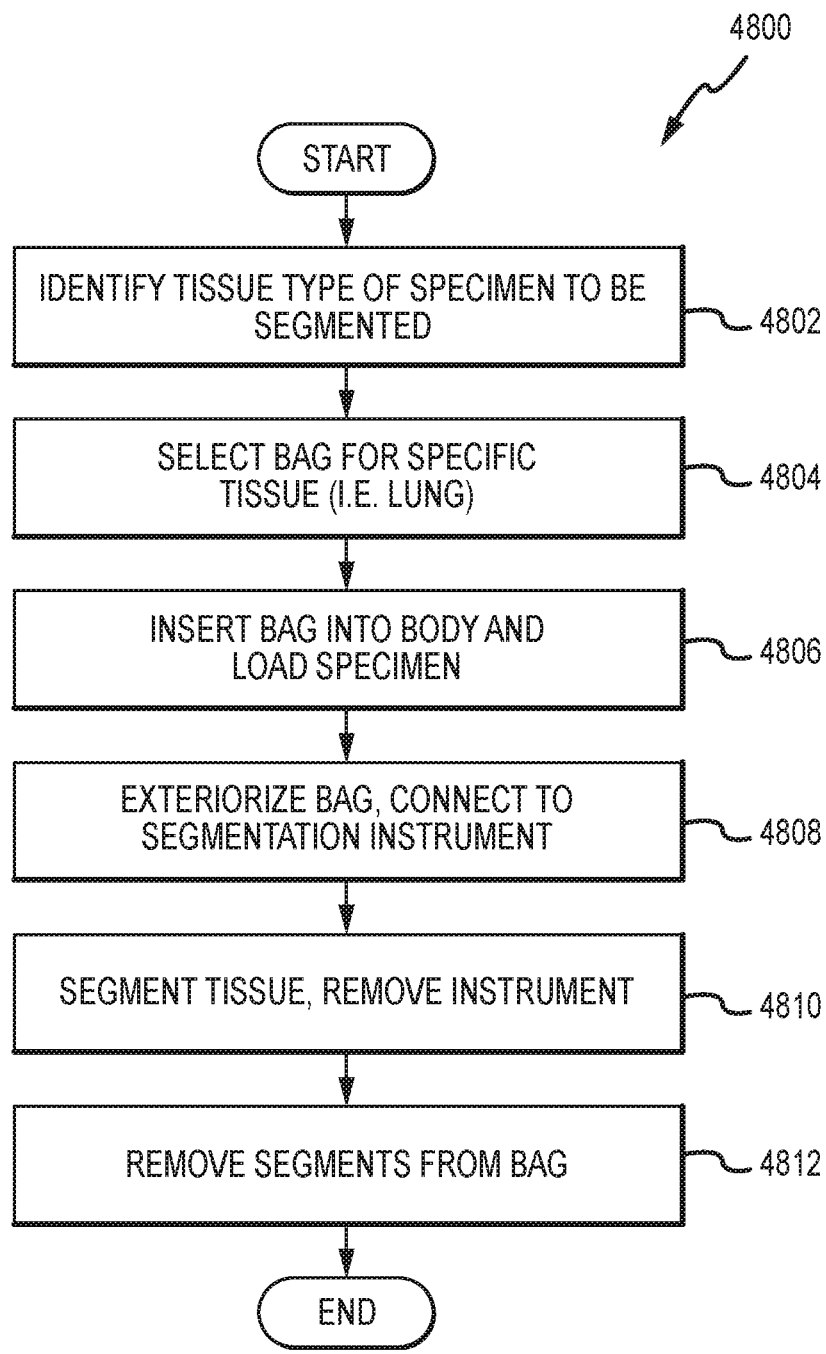
FIG. 48 illustrates a flowchart of a surgical method.

Turning now to FIG. 48, a novel method 4800 of tissue segmentation is further described herein. The method 4800 includes identifying 4802 a tissue type of a specimen to be segmented, selecting 4804 a removal bag for the specific tissue, inserting 4806 the removal bag into the patient cavity, loading the specimen in the bag, exteriorizing 4808 the bag (and optionally connecting the bag to a segmentation instrument), and segmenting 4810 the tissue (and optionally removing the instrument). The method 4800 may include removing 4812 the segmented tissue from the patient and/or the bag.

As previously described, a wire or electrode coating may be provided to enable tissue segmentation at a relatively low power and low temperature, with a relatively quick initiation of a tissue segmentation cut.

As illustrated in FIG. 48, in some embodiments, selecting 4804 a bag may include selecting a bag having a wire coating wherein the wire coating impedance is matched to the impedance of the tissue being cut. For example, lung is a higher impedance tissue than many other tissues found in the human body. Therefore, selecting 4804 a lung specific bag may include selecting a bag having a relatively higher impedance coated wire, to optimize energy into the tissue resulting in faster, lower temperature cuts, than a wire that is used to cut lower impedance tissues such as a uterus or ovarian cyst. The user might select a bag with specific wire or specific return electrode impedance based on the tissue specimen targeted for segmentation and removal. Those skilled in the art will understand that various alerts may be provided to indicate to the user which bag has been selected and/or to confirm whether or not the selected bag does in fact have a coated wire/electrode with an impedance that matches the impedance of the tissue being cut.

Figure 49:
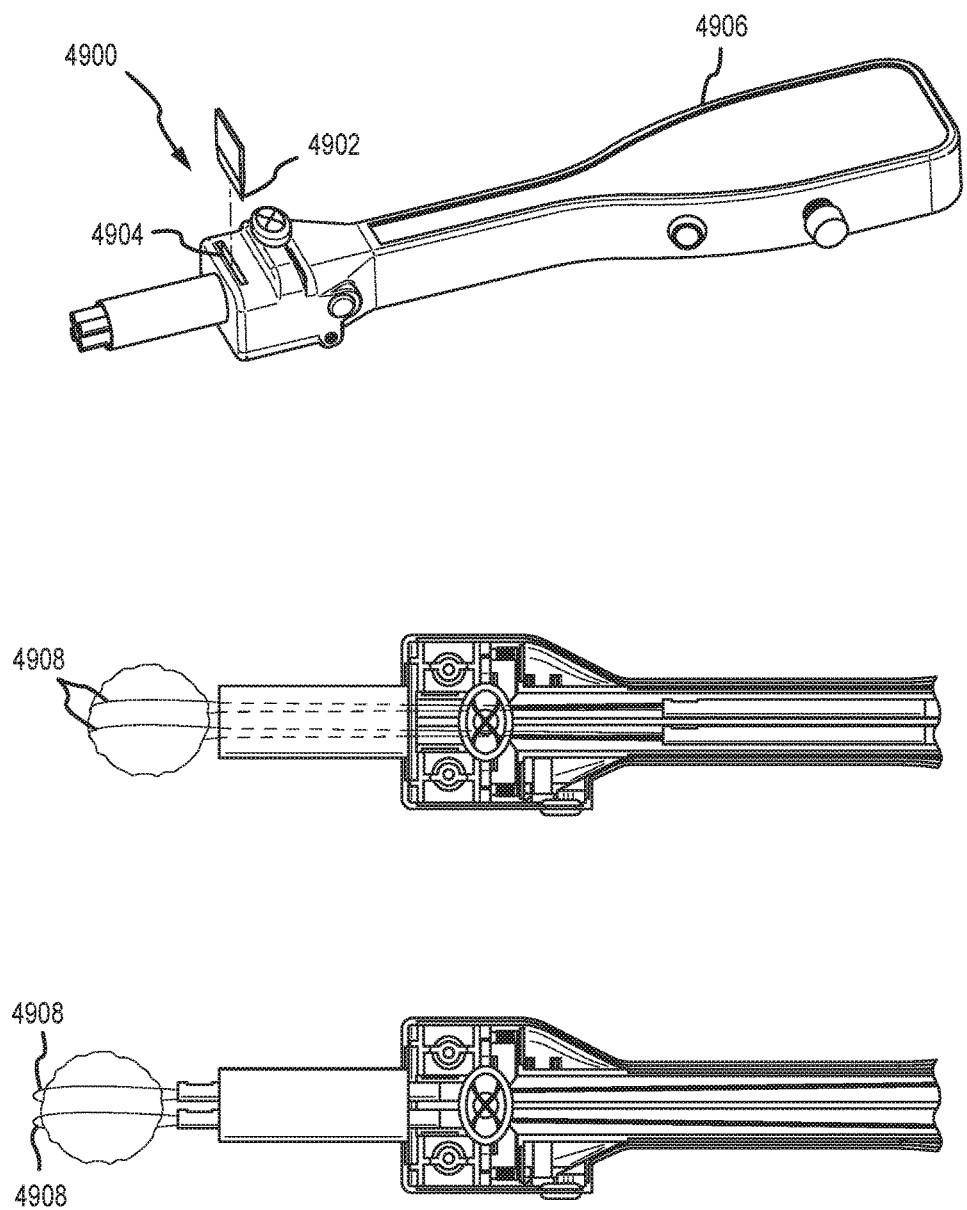
FIG. 49 illustrates several views of an electrosurgical device having an emergency release mechanism.

Turning now to FIG. 49, a system and method for providing an emergency release, abort or release of the wire connectors of an electrosurgical instrument is disclosed herein. In some embodiments, the emergency release 4900 has a plunge cutter 4902 in a slot 4904 in the instrument housing 4906, such as between a distal end of a trough (spring assembly) and an introducer tube. That is, the emergency release 4900 may function similarly to a guillotine cutter to sever one or more or all electrodes/wires 4908 for emergency release, and may be included in the system 100 illustrated in FIG. 1.

In some embodiments, an emergency release of the wire connectors from the instrument is provided. The emergency release may include a clamp or "brake" associated with the spring(s), which allows the device to be pulled away by a force exceeding the force or strength of the wires, causing them to break.

The emergency release may include pushing the insertion tube against the tissue so that it extends beyond the range of the wires, causing a higher force on the wires, which ultimately breaks the wires or connections. The emergency release may include the use of a nitinol spring or clip in the wire crimp barrel that releases the wire crimp from the connector barrel. The emergency release may include a member or release feature configured to apply a force from behind that re-extends the springs to the position prior to tensioning, to allow the user to remove the connectors, retract the distal insertion tube and insert a component that can couple to the springs and pull them forward allowing disconnection by the user. The emergency release may include an aperture that, when collapsed, constricts around the wires severing the connections. The emergency release may include a connector system in which a magnetic coupling retains the connection, wherein removal of the magnetic field causes the connectors to separate. The emergency release may include a release feature integrated into the device, such as a lockout collar that is rotatable to extend the spring back to the original position, such as after having moved the spring by rotation in a different direction.

In some embodiments, an emergency release is provided with a tensioning rod designed with a release force just above the maximum range of intended use, and where the connection point either separates or collapses when the applied force exceeds a trip point or the maximum range of intended use. In some embodiments, the segmentation device is configured such that the user may apply a higher force away from the patient, and the tensioning rods are configured to release in response, such as when the higher force reaches a trip threshold or maximum range of intended use.

In some embodiments, a lock feature is provided on the tension rod that opens jaws that hold the connector when force is lost after tensioning is started or with a user initiated control. The lock feature may be used in conjunction with a brake and a relaxation of the force by pushing the device into the patient to release the connectors.

In some embodiments, a cutting feature is provided on the tensioning rod, and configured to cut the wires upon user initiation, such as a knife edge or a pinch point that moves to contact the wires.

In some embodiments, an eject feature on the tension rod is provided and configured to eject the connectors at user initiation, lift gates that sever the wire at the distal end of the tray, electrical excitation, such as a different resonant frequency or energy level, to melt, drive a phase change, soften or release a retainer pin, a pinned connector rod pin pushed out from the back to release.

Figure 50:
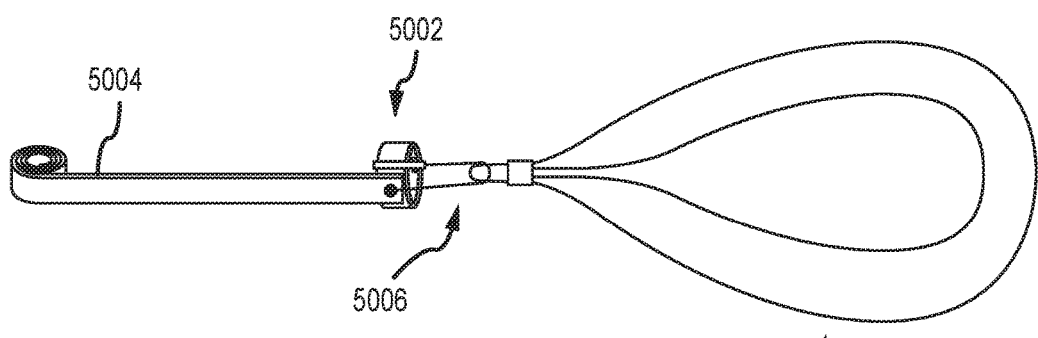
FIG. 50 illustrates a release mechanism.

In some embodiments, and as illustrated in FIG. 50, a release similar to a "kite harness release" in which the tensioning rod has a pin attached to a loop captured by a collar 5002, the loop 5006 coupled to the tensioning rod end. When the collar 5002 is moved such that it no longer captures the pin, the pin flips, allowing the tension rod end to release. The collar 5002 can be moved by an interference designed into the tube or can be replace by a close contact fit of a tube that hold the pin from flipping allowing the release. In this manner the release can be enabled by using concentric tubes that have slots such that when aligned with a solid portion of the tube the release cannot occur, as there is not enough open space to allow the pin to flip, but when the tube is aligned with the slot, the pin will flip and the connectors will release the wire(s) 5008 from the spring 5004.

Figure 51:
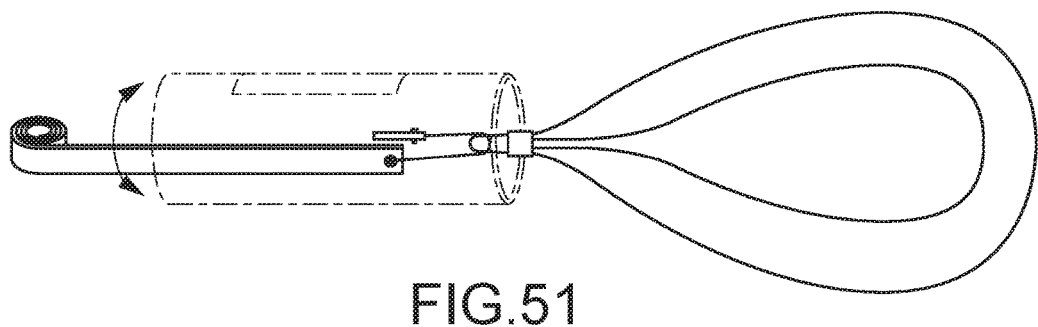
FIG. 51 illustrates a release mechanism.

Turning now to FIG. 51 some embodiments, a release similar to a "sailing cable release" which is similar to the 'kite harness' described with reference to FIG. 50. By analogy, in sailing, these "under tension release mechanisms" are found in pelican hooks and rope clutches.

In some embodiments, an emergency release including a "jack" engagement is provided, wherein the tensioning rod has a raised portion that aligns with an open portion of a flat spring on the wire connector. The wire connector is pushed onto the tension rod until the open portion of the wire connector captures the raised tensioning rod. The flat spring on the wire connector extends distally beyond the tensioning rod and has a raised shape that will interfere with features in the lumen of the instrument if reverse force is applied. This reverse force can be stepped features molded, machined or added to the lumen interior surface or can be provided by strips of an interior tube that can only interfere with the spring if rotated to the "release" position, thereby only allowing release when the user actively enables that feature.

In some embodiments, an emergency release of the tensioning mechanism and/or other components is provided by way of a detent connection. For example, a movable protrusion in a first component and biased towards an extended position may be provided and configured to selectively engage a recess or passage in a second component. The detent connection may be configured to selectively release in response to a tripping force or an override input.

Figure 52:
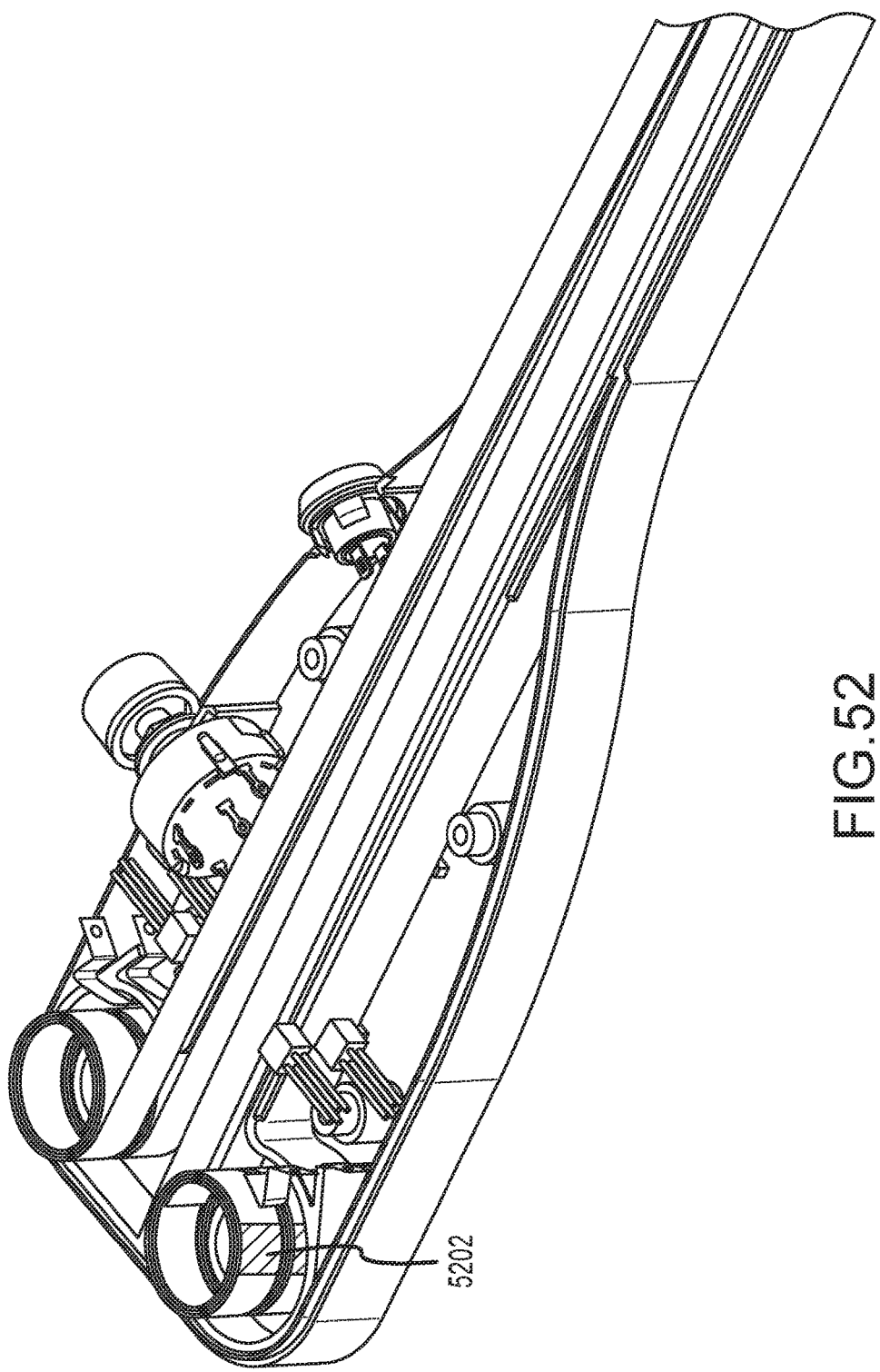
FIG. 52 illustrates a perspective view of some components of an electrosurgical device.

Turning now to FIG. 52, a spring insulation feature is now described in detail. As illustrated in FIG. 52, a selective insulation region 5202 may be provided to prevent the flow of electricity ("drag strip" only contacting insulation) and to control when the electrode/wire can be electrified.

In addition, parallel sections of the spring that are electrically conductive but not electrically coupled may be incorporated on the spring surface. In some embodiments, this effect is created with the application of a thin conductive layer with an insulated backing. By the addition of these electrical "traces", separate contact members may be provided that aligns with these traces to allow different electrical signals to be coupled along the length of the spring without interference. In some embodiments, the resistance values from the electrode wire resistors are supplied to a circuit within a fixed portion of the electrosurgical instrument 102, to identify the type of electrode, such as in a manner previously described herein.

Figure 53:
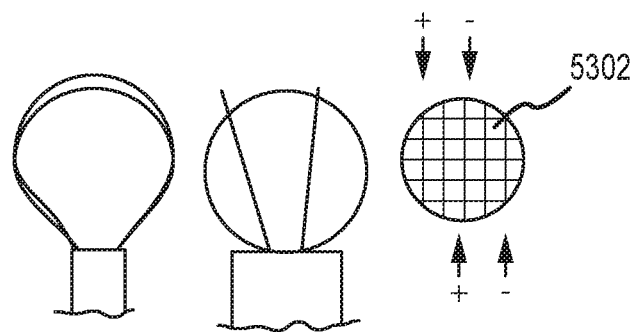
FIG. 53 illustrates a side view of a cutting wire embodiment.

As illustrated in FIG. 53, in some embodiments, return electrode wires may be incorporated in a cutting mesh. The wires 5302 may be activated as they are retracted, dividing the specimen.

Figure 54:
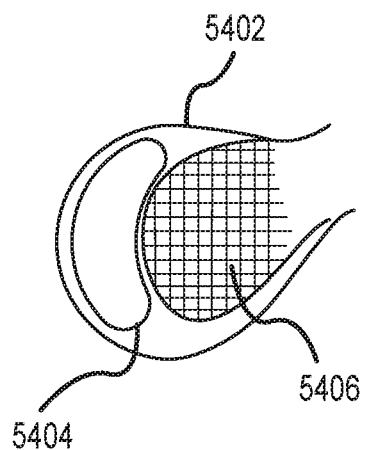
FIG. 54 illustrates a side partial section view of a double retrieval bag with wire mesh and inflation mechanism.

As illustrated in FIG. 54, some embodiments include a double bag, with an outer bag 5402 and an inner bag having a multiplexed power or RF energy cutting mesh 5406. To cut the tissue, a mesh of bipolar RF cutting wires may line the retrieval bag. Upon capture, the wires may be activated (such as in sequence as previously described herein) and cut the sample into smaller pieces while pulling the mesh into the shaft. By sealing the bag against the shaft, inflating the bag, such as by using a balloon 5404 in or coupled to the outer or inner bag 5402, 5406, may also assist in pushing the sample or pieces of the sample into the shaft. The resulting segmented pieces may be elongated pieces.

Figure 55:
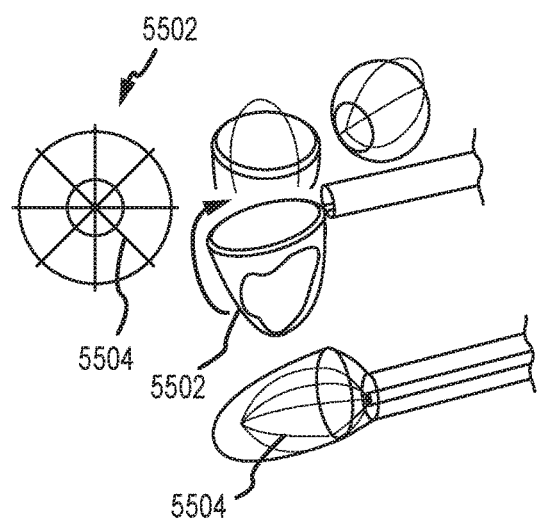
FIG. 55 illustrates various views of a collapsing retrieval basket.

As is illustrated in FIG. 55, some embodiments include a collapsible basket 5502, such as a cutting mesh or basket 5502 of electrodes 5504 oriented perpendicular to the open specimen bag, allowing tissue to be captured therein. The bag may then be closed about the shaft and reoriented to be parallel to the shaft axis and wire mesh. The wires may then be activated as they are pulled into the shaft to cut the specimen into smaller pieces. The resulting segmented tissue pieces may be pie shaped.

Figure 56:
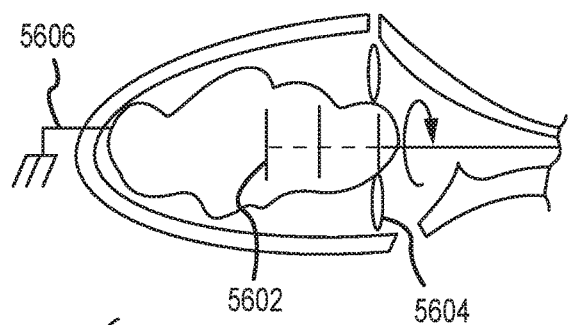
FIG. 56 illustrates a rotating power electrode cutting device.

As is illustrated in FIG. 56, some embodiments include a rotating bipolar power such as a radio frequency energy cutting mechanism and a stationary specimen, held by the bag. The cutting mechanism 5602 may be configured to advance or move distally or proximally as it rotates. The resulting segmented tissue 5604 may be removed from the specimen during the procedure. The return electrode 5606 may be a part of the bag.

Figure 57:
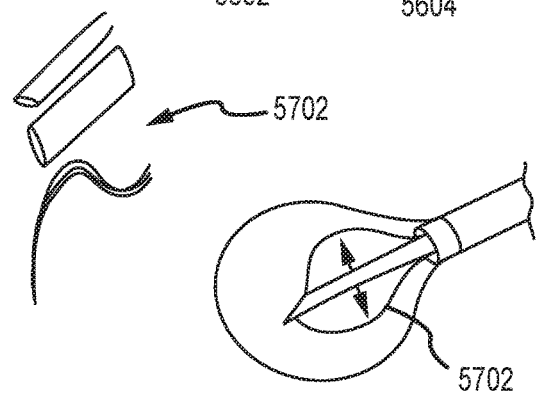
FIG. 57 illustrates rotating wire electrodes having sharp leading edges.

As is illustrated in FIG. 57, in some embodiments, a rotating cutting mechanism 5702 may include rotating wires. The rotating wires may have sharp corners to maximize current density and/or to bend to expand the cutting structure.

Figure 58:
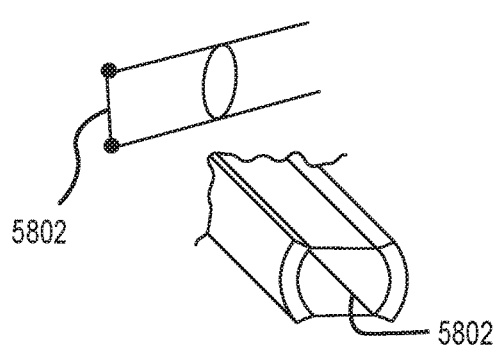
FIG. 58 illustrates a single electrode wire embodiment.

As is illustrated in FIG. 58, in some embodiments, a single bipolar electrode wire may be provided to divide the disuse. The wire 5802 may be advanced and retracted while rotating to different orientations. The resulting tissue segments may be substantially cylindrically shaped.

Figure 59:
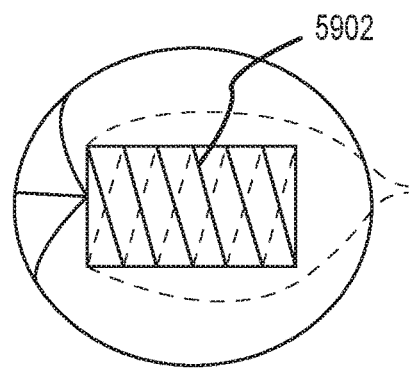
FIG. 59 illustrates a bipolar device with active and return wires constricting a tissue specimen.

As is illustrated in FIG. 59, in some embodiments, active electrode(s) 5902 and return electrode may be wrapped around the specimen or arranged such that the wires can be constricted around the specimen that is captured in the retrieval bag. The wires may then be retracted and activated simultaneously to divide the sample. The resulting tissue segments may be substantially shaped like segments of rotini pasta.

Figure 60:
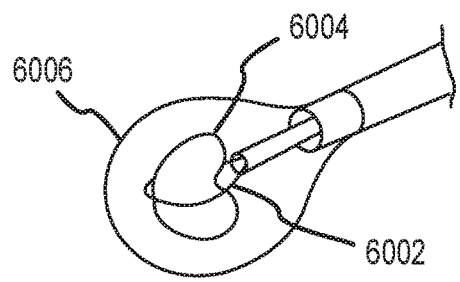
FIG. 60 illustrates a cutting and grasping loop in a retrieval bag.

As is illustrated in FIG. 60, in some embodiments, a cutting/grasping loop in the retrieval bag 1616 may be provided. The cutting loop may be an electrode that is extended down the retrieval bag shaft. The wires 6002 may travel from the exterior of the specimen and "scoop" and cut the specimen into smaller, more manageable pieces. An articulator may be provided. The electrode wire loop 6002 may be collapsed or collapsible on each segmented piece 6004 to pull it out of the patient cavity. The tissue segments 6004 may look like orange slices.

Figure 61:
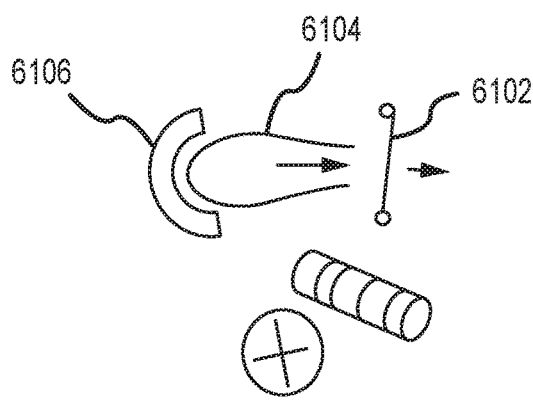
FIG. 61 illustrates a stationary cutting mechanism and moving tissue arrangement.

As is illustrated in FIG. 61, some embodiments provide for a stationary cutting mechanism 6102 with moving tissue 6104. For example, the specimen 6104 may be pulled into a bipolar RF electrode wire 6102. The specimen may be captured in the retrieval bag portion of the device. The bag may then be pulled into the device shaft, passing through an activated wire electrode along the way. To encapsulate the specimen being cut, another bag 6106 or electrode mesh may be exterior of the specimen. The mesh may also serve as a return electrode. The bag/cutter may be manually rotated to obtain multiple cuts in the tissue.

Figure 62:
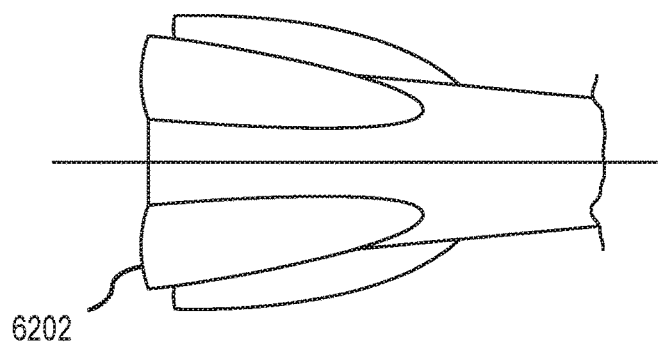
FIG. 62 illustrates a push/pull grid cutting mechanism.

As is illustrated in FIG. 62, a push-pull electrode grid with an expandable funnel may be provided in some embodiments. The specimen may be drawn into the device shaft through a plurality of electrodes. The distal end of the shaft may expand into a funnel 6202 to gather the specimen into the shaft as the retrieval bag is pulled in. The shaft/cutter may be manually rotated to obtain multiple cuts.

Figure 63:
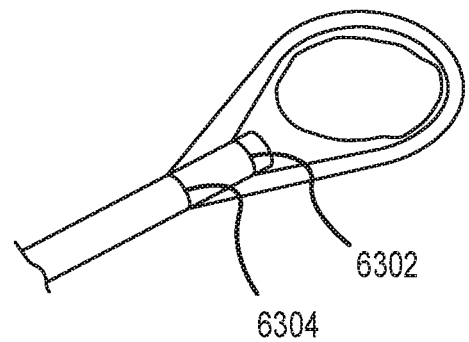
FIG. 63 illustrates a multistage rigid cutting mechanism.

As is illustrated in FIG. 63, some embodiments provide for pulling a specimen into a multistage rigid electrode or RF cutting mechanism. A series of bipolar electrode wires clocked at different angles to cut through tissue as the tissue is drawn into the device shaft. No manual rotation is required. The electrode wires may be inside the funnel, such as at a first stage 6302 and a second stage 6304.

Figure 64:
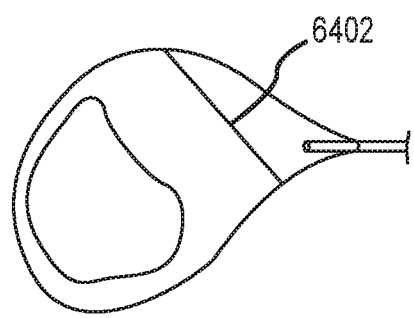
FIG. 64 illustrates a stationary cutting electrode system.

As is illustrated in FIG. 64, some embodiments provide a stationary cutting wire with a grasper/manipulator as a return electrode. In some embodiments, one or more stationary electrode wires 6402, with a grasper, which may also be the return electrode, is used to pull the specimen into the electrode wires. The segmented tissue may be removed through the shaft or incision. The funnel 6202 illustrated in FIG. 62 may be provided here as well.

Figure 65:
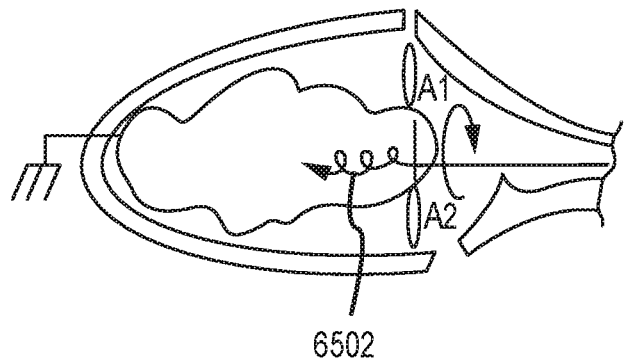
FIG. 65 illustrates a skewer mechanism for tissue segmentation.

As illustrated in FIG. 65, some embodiments may provide for a rotating edge peeling/cutting action. For example, rather than only pushing or only pulling the specimen through the wire, some embodiments provide a "skewer" 6502 to rotate the specimen through one or more bipolar electrode cutting wires or wire loops. This creates a spiral cut as the specimen is drawn into the shaft, which elongates the segmented tissue.

Figure 66:
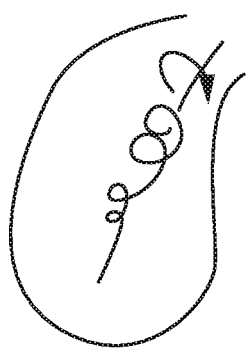
FIG. 66 illustrates a spiral electrode cutting mechanism.

As illustrated in FIG. 66, a spiral cutting electrode may be provided in some embodiments. In some embodiments, a rotating skewer or a rotating bag may impart rotation on the enclosed specimen. One or more bipolar electrode cutting wires may then be used to skive/scallop the tissue as it is pulled through/against the wire. The skewer and/or the bag may include the return electrode.

Figure 67:
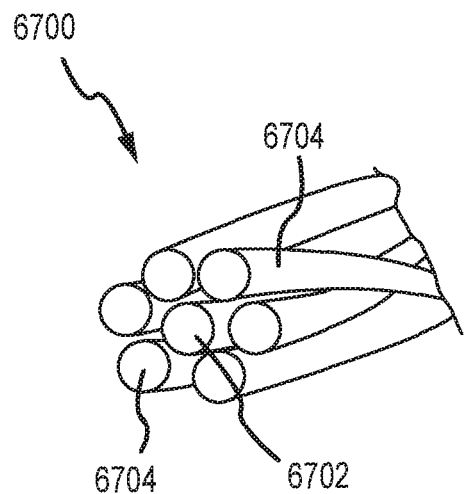
FIG. 67 illustrates an electrode construction having thread woven with metal filars.

As illustrated in FIG. 67, an electrode construction 6700 may include thread 6704 woven with metal filars 6702. The return electrode 6700 may be incorporated into the fabric making up the specimen bag. For example, wires 6702 woven directly into the thread 6704 used to make the bag may provide one embodiment of a return electrode 6700.

Figure 68:
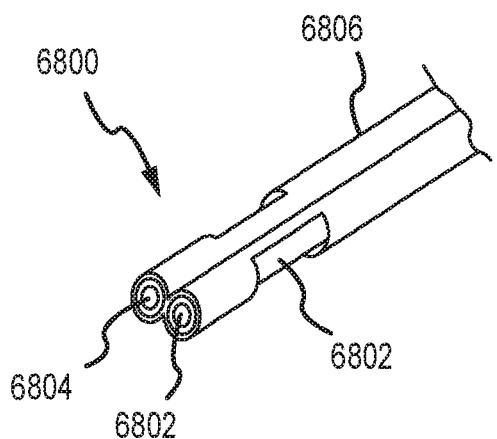
FIG. 68 illustrates an electrode construction with bipolar/bifilar wire pairs.

As illustrated in FIG. 68, a bipolar/bifilar wire pair arrangement 6800 may provide an electrode construction 6800. In some embodiments, a series of bifilar wire pairs may be provided to enable bipolar RF energy for creating cuts. Each wire pair 6800 may include an active electrode 6802 and a return electrode 6804. The wires 6802, 6804 may be exposed through the insulation 6806 on opposing sides of the structure by way of one or more windows or recesses 6808 in the insulation 6806.

Figure 69:
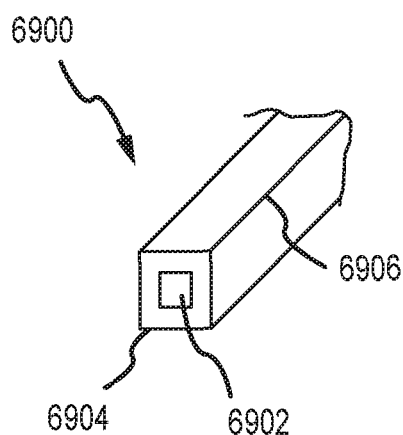
FIG. 69 illustrates a square wire electrode.

As illustrated in FIG. 69, although most wire electrodes illustrated herein are shown as substantially rounded, those skilled in the art will recognize that wire electrodes 6900 having other wire electrode shapes are envisioned, such as a square wire electrode 6900. A square wire electrode 6900 may maximize current density at the corners. This may reduce the power required to initiate cutting using bipolar RF energy. The wire 6902 may have a coating 6904. The corner(s) 6906 of the wire electrode 6900 may provide an area to concentrate the current density, thereby making cutting or cut initiation more efficient.

Figure 70:
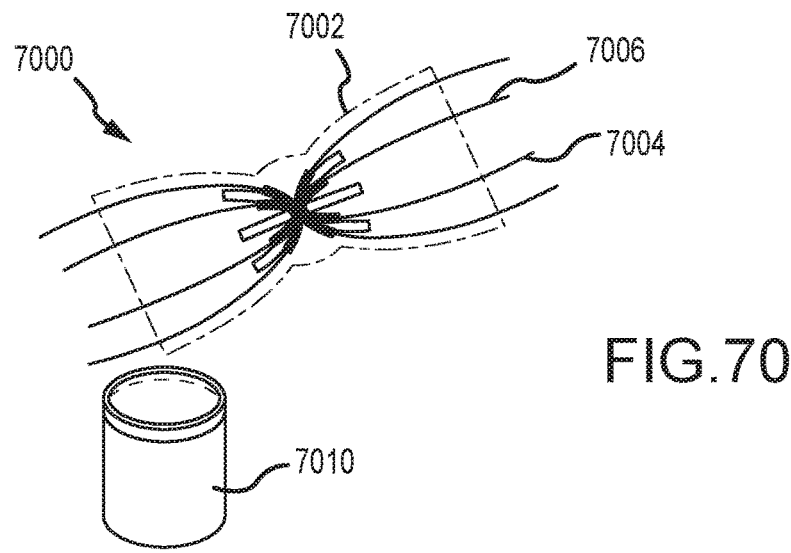
FIG. 70 illustrates a removal bag.

As illustrated in FIG. 70, some embodiments of a bag construction 7000 may include a bag 7002 that incorporates both the return electrode 7004 and the active electrode 7006 for applying power, such as bipolar RF energy. A converter may manufacture the structure 7010 prior to welding a flat pattern into a bag shape.

Figure 71:
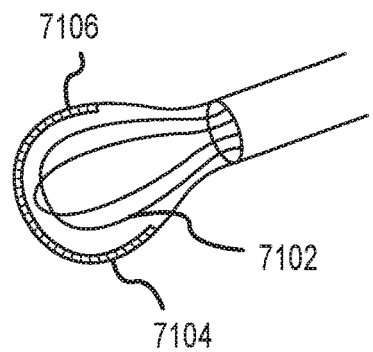
FIG. 71 illustrates a wire and bag construction.

As illustrated in FIG. 71, some embodiments provide for a bipolar electrode 7102 and a return electrode woven into the bag. In some embodiments, fine wires 7104 may provide the return electrode. The fine wires 7104 may be woven into a polymeric fabric 7106 that forms the retrieval bag.

Figure 72:
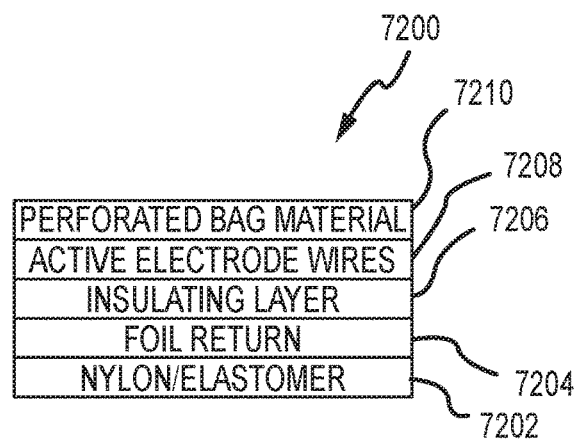
FIG. 72 illustrates a bag and return electrode construction.

As illustrated in FIG. 72, some embodiments provide for a bag construction 7200 having active and return electrodes. In some embodiments, active electrode wires may be incorporated into the specimen bag by providing a multilayer construction. The outer layer 7202 may include a nylon or elastomer, the next layer 7204 may include a foil return, the next layer 7206 may include an insulating layer, the next layer 7208 may include the active electrode wire(s), and the next or innermost layer 7210 may include a perforated bag material.

Figure 73:
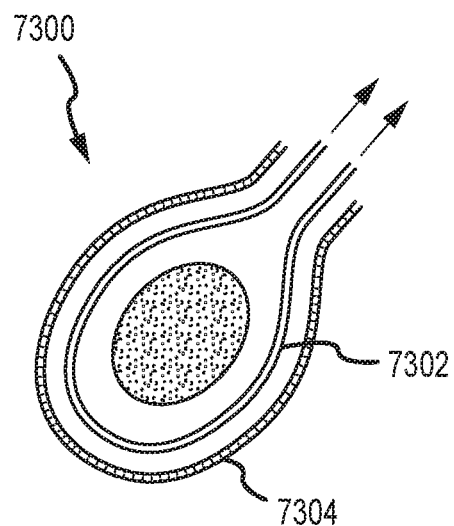
FIG. 73 illustrates a dual bag construction with an inner bag configured to constrict tissue.

As illustrated in FIG. 73, some embodiments include a dual bag construction 7300 for pre-tensioning the specimen. The dual bag construction 7300 may include an interior bag 7302, which may constrict the specimen by collapsing against the device, while the outer bag 7304 may contain or enclose the wire(s)/electrode(s) (not illustrated) used for cutting the specimen. The return electrode (not illustrated) may also be housed in the outer bag 7304.

Figure 74:
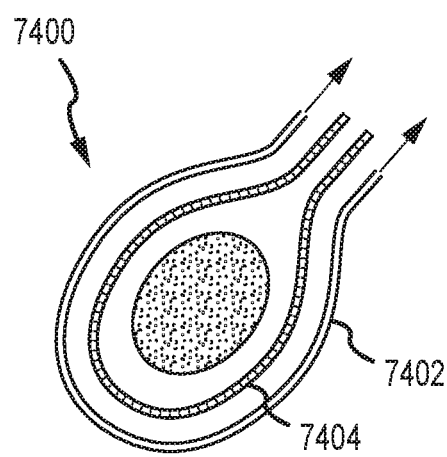
FIG. 74 illustrates a dual bag construction with an outer bag configured to constrict tissue.

As illustrated in FIG. 74, some embodiments provide a dual bag construction with return electrodes (not illustrated) in the outermost bag 7402. A dual layer bag construction 7400 may be used such that the outer bag 7402 constricts the specimen and contains the return electrode. The inner bag 7404 may contain the active electrode(s) (not illustrated) for cutting.

Figure 75:
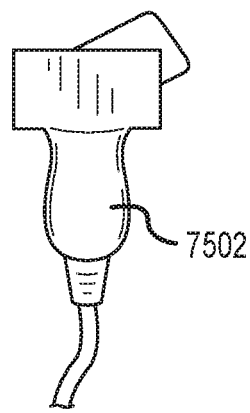
FIG. 75 illustrates energy delivery using an in-cord signal controller (multiplexing)

As illustrated in FIG. 75, some embodiments provide an in-cord signal controller (multiplexing). To address the potential use of a variety of generators for the power (such as RF energy) driving the cutting, a controller 108, 708, 7502 may be provided in series with the device cable. The controller 108, 708, 7502 may be used in conjunction with a project requiring multiplexing of the signal.

Figure 76:
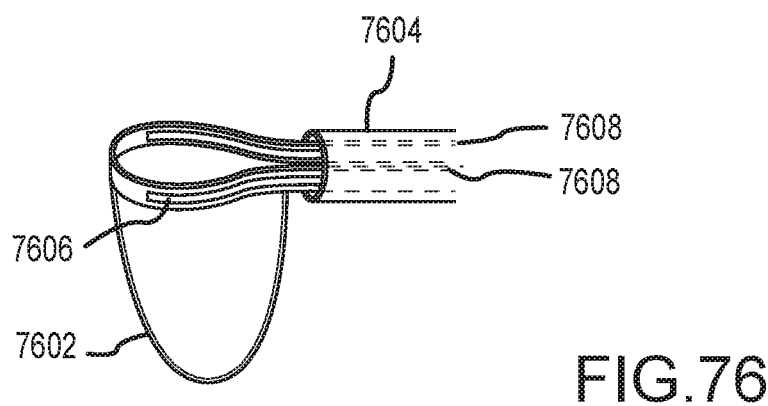
FIG. 76 illustrates a retrieval bag specimen capture and cut device.

As illustrated in FIG. 76, a retrieval bag 7602 may be provided with an over tube 7604 for cutting and exteriorizing tissue. In some embodiments, support arms 7606 and drawstrings 7608 positioned between the over tube 7604 and the main device shaft (not illustrated) may assist in reorienting the retrieval bag 7602. In some embodiments, providing two or more drawstrings 7608 may provide improved control of the bag closure and increase the tendency of the bag to 7602 close over the device shaft (not illustrated).

Figure 77:
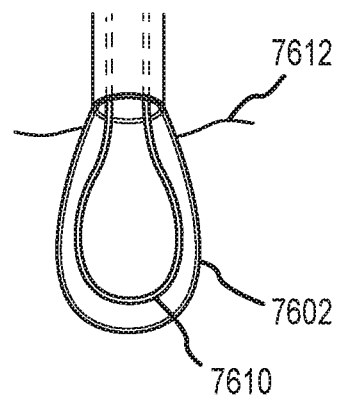
FIG. 77 illustrates another view of the device in FIG. 72.

As illustrated in FIG. 77, in some embodiments, a method of using the specimen retrieval bag 7602 is provided. One method includes capturing the specimen in the bag 7602, and then dividing the tissue into smaller pieces for removal. The bag 7602 may be initially open perpendicular to the shaft (not illustrated) as illustrated in FIG. 76, and then rotated over the shaft/through the incision, as illustrated in FIG. 73, for applying a cutting to the specimen therein, using one or more electrodes 7610. External drawstrings 7612 may assist in positioning the bag 7602.

Figure 78:
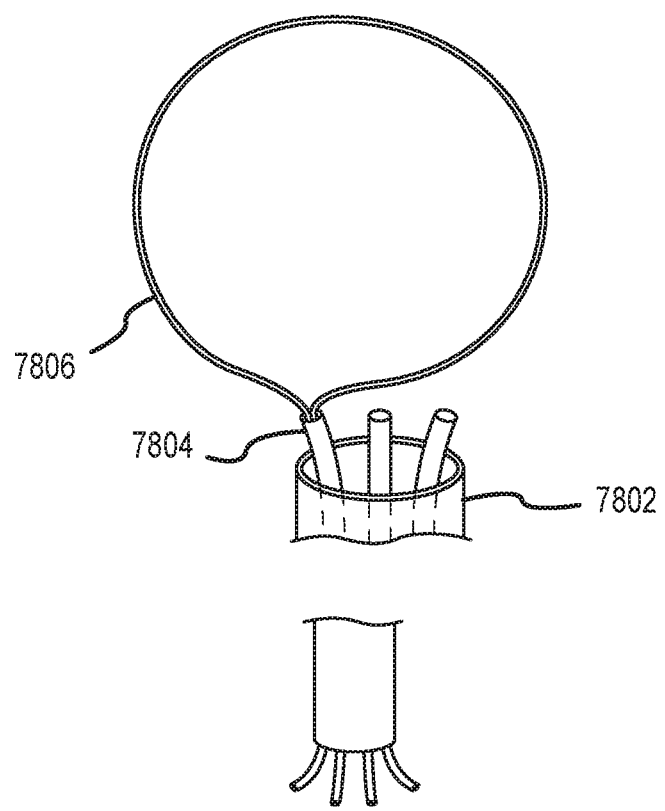
FIG. 78 illustrates guides for wire loops.

As illustrated in FIG. 78, some embodiments provide guides for wire loops. For example, a shaft tip 7802 or distal portion of a shaft may include a guide 7804 for each wire electrode 7806. The guides 7804 may bias the wires 7806 away from each other to prevent them from touching, thereby maintaining the cutting path of the wires 7806.

Figure 79:
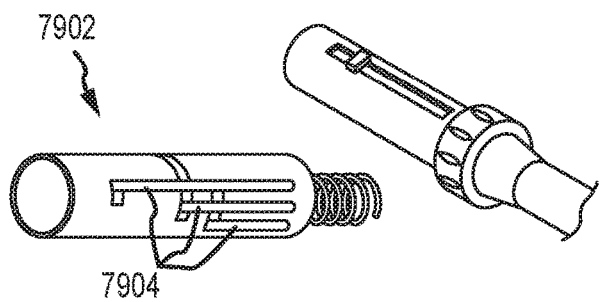
FIG. 79 illustrates a cam tube for organizing or sequencing electrodes.

As illustrated in FIG. 79, a cam tube 7902 for activating bipolar power and tensioning of each wire loop may be provided in some embodiments. The cam tube 7902 may organize the sequencing of each cutting wire. The tube may have slots 7904 to only allow one loop or loop pair to activate at a given time. Each loop/loop pair may be pulled manually. Rotating the cam tube may control which wire is available for power or RF energy activation as well.

Figure 80:
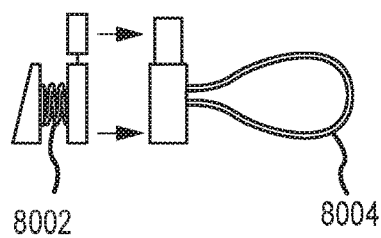
FIG. 80 illustrates an electrode loop with opposing springs for tension control.

As illustrated in FIG. 80, a wire loop with opposing springs 8002 to control the wire tension over time may be provided. In some embodiments, a pair of springs or other components may be used to automate the wire forces during cutting, thereby creating a variable spring force on the wire 8004 over the pull through the tissue. Applicant has determined that slowing the rate of pull near the end of the cut reduces sparking or flashing of the electrodes.

Figure 81:
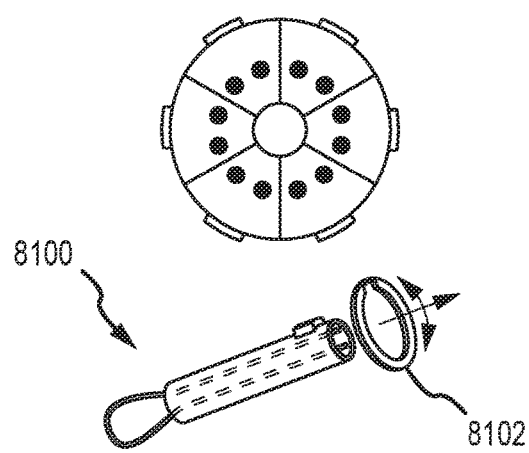
FIG. 81 illustrates a shaft construction.

As illustrated in FIG. 81, a handle or shaft structure for individual wire loops may be provided. In some embodiments, a rotation ring 8102 in a shaft construction 8100 may be used to release wire columns that are actively tensioned by extension springs. A user may rotate the ring to release one rod and activate the power or RF energy. In some embodiments, each cut requires about 20 to 25 centimeters (or about 8 to 10 inches) of travel may be provided.

Embodiments disclosed herein may be used in polypectomy, dissector, or other applications where wire cutting with coagulation or hemostasis is desired.

Figure 82:
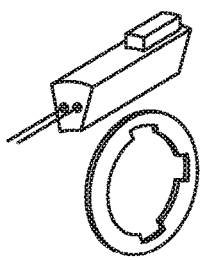
FIG. 82 illustrates another shaft construction

As illustrated in FIG. 82, a manual wire retraction may be provided instead.

Figure 83:
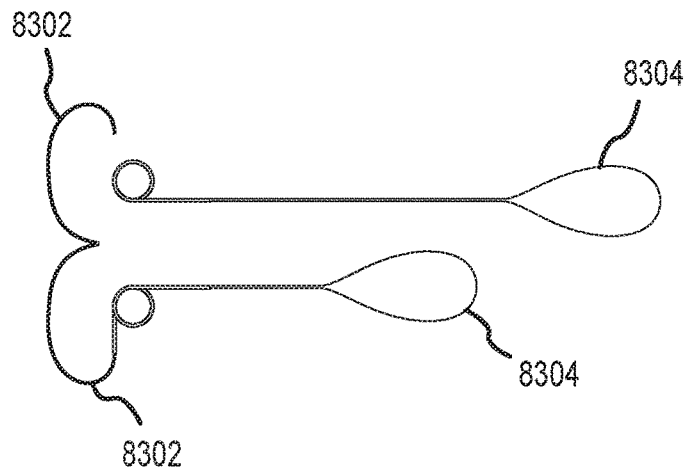
FIG. 83 illustrates torsion springs for tensioning wires/electrodes.

As illustrated in FIG. 83, torsion springs 8302 for achieving wire tension during a cut may be provided. The torsion springs 8302 may be constant force springs, and may provide for the retraction of cutting wires/electrodes 8304. The torsion springs may coil the wire or other structure that pulls the wire into the device shaft. The torsion spring 8302 may operate sequentially.

Figure 84:
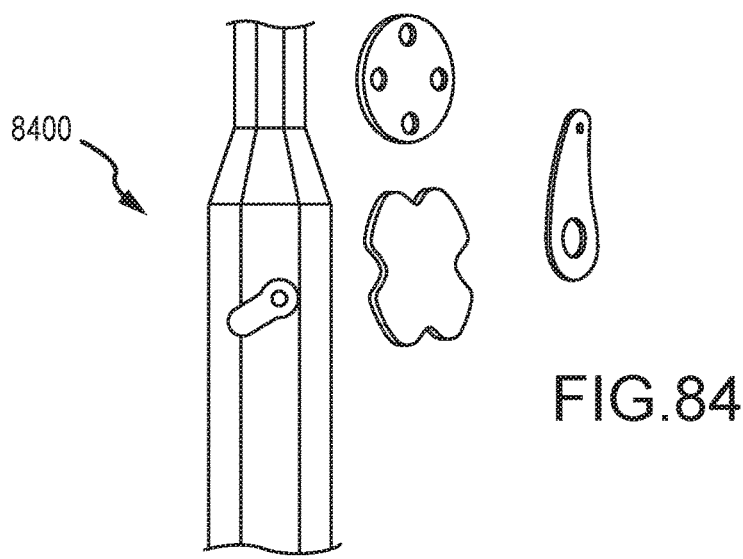
FIG. 84 illustrates wire activation using a cam and lobe.

As illustrated in FIG. 84, some embodiments provide for electrode wire activation using a cam and lobe mechanism 8400. A rotating cam may lift each radially spaced wire/electrode out to another electrical contact, to select wires/electrodes for power or RF energy. The cam may be rotated to release one wire/electrode and activate another.

Figure 85:
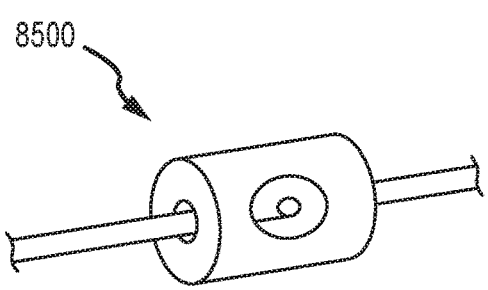
FIG. 85 illustrates a wire length lock mechanism.

As illustrated in FIG. 85, some embodiments provide for a wire/electrode length lock mechanism 8500 or method. In some embodiments, a cam lock slide is provided, and may be advanced onto the wire/electrode until a certain force is achieved. The cam may then lock the wire/electrode in place as the wire/electrode relaxes slightly. The cam lock provides for a method of pre-tensioning the wire/electrode against the specimen before initiating power and/or cutting tension.

During low temperature, rapid wire cutting applications, the delivery of energy where some level of hemostasis is desirable may be altered to provide both hemostasis as well as rapid cutting.

One means to increase hemostasis is to alter how energy is applied initially during a wire cut. A voltage limited power, with a low voltage and higher current capability, may be delivered initially to the tensioned wire cutter so as to delay the cut initiation and allowing coagulation of tissue prior to cutting. At a predetermined time or until a predetermined parameter threshold is met, the energy delivery could then be altered such that the wire cutting is initiated through increased voltage. Another means to accomplish this would be to initially apply a non-sinusoidal waveform to enhance the coagulation effects and to transition to a sinusoidal waveform to enhance cutting. This can be a single event or can be continuously adjusted as the cut advances. This may also be adjusted by modulating between a pure sinusoidal waveform and a higher crest factor waveform based on feedback from electrical or rate of travel data to improve control and the cutting performance. This modulation can be pulse width modulation, changing distortion characteristics of the waveform, elimination or changes in amplitude of cycles or partial cycles of the output, changing dampening characteristics by adding or subtracting loads on the RF output stage, or other means.

Parameters that may be of interest to monitor include electrical parameters such as impedance or phase change or mechanical parameters such as tissue shrinkage or compliance. During the initial hemostasis step a higher force may be applied to the wire during coagulation than is required for the cutting alone with pressures as high as 100-200 psi. The force may then be lowered or maintained to complete the cutting. Coagulation or hemostasis times may vary, but times are expected to be between 0.25-10 seconds. Wires may or may not have high impedance coatings or alternatively a nonstick coating depending on the application.

Figure 86:
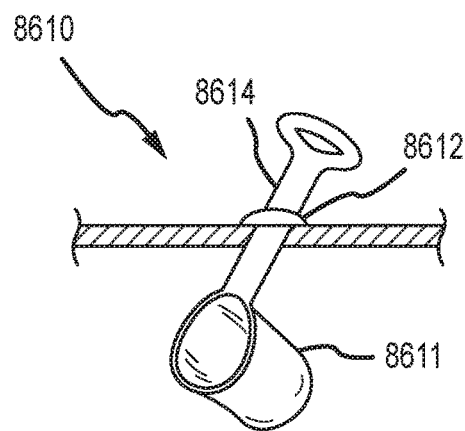
FIG. 86 illustrates an introducer instrument and removal bag.

Turning now to FIG. 86, it illustrates an instrument 8610 suitable for maintaining pneumoperitoneum during the loading of the bag 8611. The introducer 8610 may have a sealer 8612 on the shaft 8614 that provides a seal when pushed against the incision site. This sealer 8612 may be on the inside or outside of the patient. The sealer 8612 may include an inflatable or non-inflatable feature. The user may be able to move or slide the sealer 8612 along the length of the shaft 8614 to position sealer 8612 at or near the incision and/or to move the sealer 8612 away from the incision at a suitable time. In some embodiments, the sealer 8612 includes a cup-shaped feature that surrounds or encloses the introducer shaft and is flexible at the introducer shaft to enable movement of the introducer with minimal movement of the cup-shaped feature. In some embodiments, an opening that interfaces with the instrument 200 is compliant such that the sealer 8612 can be removed after use and placed on another instrument (such as a grasper) intended to help with the loading and exteriorizing of the bag 8611.

In some embodiments, it may be desirable to reliably close a removal bag, such as for lap to vaginal removal. For example, in some embodiments, a bag sealer tool may be provided to seal the bag opening by melting the bag together. Here, material having a relatively lower melting temperature may be provided at the opening end of the bag for more reliable, easier sealing. In some embodiments, a large clip or tie may be provided to enable a reliable closure. Here, the user may apply the clip or tie over or about a malleable material (such as a wax and/or adhesive) area or strip that is permanently attached to the bag opening to provide a fluid impermeable barrier between the contents of the bag and the exterior. The malleable material may be provided on an interior or exterior wall of the bag. Providing the malleable material on the exterior of the bag may reduce the potential or accidental pre-engagement, with engagement made possible after, for example, the user flips an end of the bag in. In the alternative, a removable strip on the malleable material may be provided, so as to prevent pre-engagement.

Figure 87A:
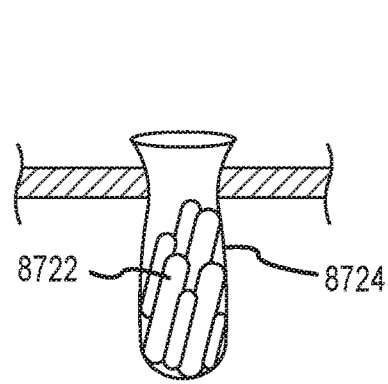
FIG. 87a illustrates various features of a wrap-around removal bag.
Figure 87B:
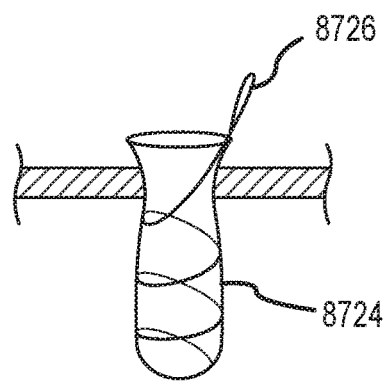
Figure 87C:
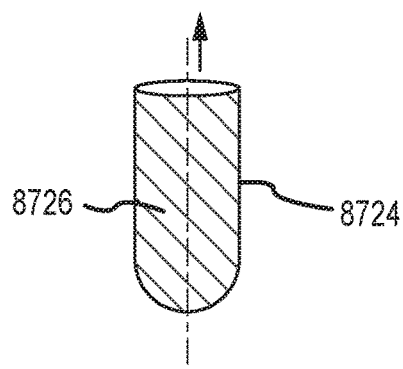

Turning now to FIGS. 87a-87c, means for aiding in the removal of segments with the bag are now described in detail. After segmenting the tissue into segments 8722, it may be desirable to remove the bag simultaneously with the specimen segments 8722, particularly in situations where cancer is suspected or known. In this situation, a bag 8724 configured to apply a compressive force on the tissue to be excised may be provided.

For example, and as illustrated in FIG. 87b, the bag 8724 may include a segment constrictor 8726 that compresses and/or reorients the segments 8722 while simultaneously applying a force to remove the bag 8724. Specifically, the segment constrictor 8726 may be configured such that, as a user pulls proximally on the segment constrictor 8726, the segments 8722 are compressed simultaneously or substantially simultaneously as the bag 8724 is pulled out of the patient (see e.g. FIG. 87*c*). In some embodiments, the segment constrictor 8726 is integrated on the interior of the bag 8724 to facilitate the reorientation of the tissue segments 8722 through direct contact. The segment constrictor 8726 may be a string or a strap-like feature. In some embodiments, the segment constrictor 8726 may have a memory-retaining material and/or be resilient so as to assist in expanding the bag 8724 to accept the tissue. In some embodiments, the surface of the segment constrictor 8726 is roughened or has protrusions that either increase the coefficient of friction between the segment constrictor 8726 and the segments 8722, or effectively "grab" the segments 8722 as the user or instrument pulls proximally.

In some embodiments, and as illustrated in FIG. 87*c*, the segment constrictor 8722 is configured to apply a constricting force that is at an angle relative to the direction of a cut or a pull force F. By applying a constricting/pulling force at an angle α of between 15-90° relative to the direction of the cut, wire retraction, or pulling force, the segments 8722 may be both compressed and repositioned to allow for removal through the incision. If more compression is desired closer to a 90° angle may be desired; in some embodiments, the angle α is between 45° and 89°; in others, the angle α is between 60° and 85°; in others, the angle α is between 70° and 80°. If more movement or reorientation of the segments is desired, the angle may be closer to 15°. In some embodiments, the angle α is between 15° and 45°; in some, the angle α is between 15° and 35°; in others, the angle α is between 15° and 20°.

Figure 88:
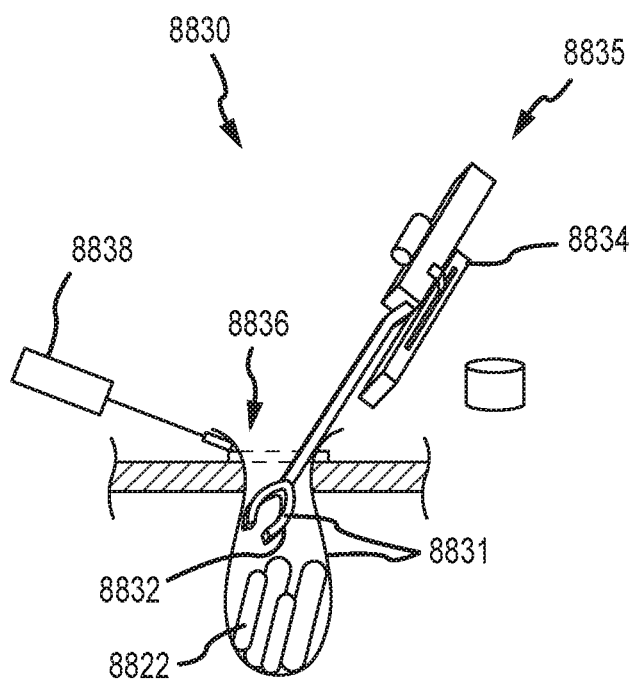
FIG. 88 illustrates another removal device.

As illustrated in FIG. 88, in some cases, a robotic or other electromechanical means may be utilized for a surgery. In such cases, it may be desired to utilize the same means to remove the segments from the bag. FIG. 88 illustrates an exemplary approach to enabling robotic assisted removal. As illustrated, a system 8830 having a tissue removal bag 8831, a robotic grasper 8832, a guide means 8834, and a bag-machine interface 8836 is provided in some embodiments.

The robotic grasper 8832 may include a camera on an arm 8835 to allow a surgeon to view the robotic grasper 8832 going in and out of a patient's body or incision. The guide means 8834 provides the ability to guide the robotic grasper 8832 in and out of the incision or a trocar including a guide between the trocar or incision site. In some embodiments the robotic grasper 8832 is configured to travel between the incision site and another location (such as a specimen or pathology container, or a tray to receive tissue).

The bag-machine interface 8836 may be provided on or proximal to the bag opening, and is configured to interface with a robotic arm 8838 and allow the arm 8838 to provide tension on the bag 8831 during removal of the tissue segments 8822 such that the segments are easily identified and grasped Some embodiments disclosed herein may be used for removing lung tissue. For example, a surgical method provided herein includes (not necessarily in this order): (1) Mark or identify margin or area of interest for pathology (optional). (2) Insert specimen bag into thoracic cavity for specimen capture. (3) Load specimen in bag. (4) Exteriorize bag opening. (5) Connect wire connectors to instrument. (6) Insert distal end of instrument into thoracic cavity. (7) Pretension wires prior to cutting. (8) Segment tissue using either mechanical or mechanical/electrical cutting. (9) Remove instrument. (10) Apply external compression force on tissue segments at an angle between 15-90° to the direction of cutting or wire retraction pull force in order to decrease bag diameter and/or re-orient tissue segments. (11) Remove bag with contained specimen(s).

A tissue removal method disclosed herein includes (not necessarily in this order): (1) Mark or identify margin or area of interest on specimen for pathology (optional). (2) Insert specimen bag into thoracic cavity for specimen capture. (3) Load specimen in bag. (4) Exteriorize bag opening. (5) Connect wire connectors to instrument. (6) Insert distal end of instrument into thoracic cavity. (7) Pretension wires prior to cutting. (8) Segment tissue using either mechanical or mechanical/electrical cutting. (9) Remove instrument. (10) Remove specimen segments. (11) Remove bag.

The temporary holding of wires to the bag may be performed in several manners. Bags may include multiple layers, or single layers with additional features attached to temporarily hold the wires in place. The bags may include several film pieces welded or adhered together, or they may be molded by reshaping a film, or blown in a mold similar to a balloon. Regardless of the approach, the means by which the wires are held in place must be releasable and release in order to complete the segmentation of the tissue.

Another important feature of using wires to segment a specimen, either with or without radiofrequency energy, is to ensure that the wires are held to the side wall of the bag, as illustrated. By keeping the wire(s) temporarily attached to the side wall of the bag, the specimen may be loaded without inadvertently shifting the wire(s) or catching on the wires so the specimen can't be fully loaded. For this purpose, the wires may be held in place using loops, perforations or similar bag features that release with tension applied to the wires. In addition, the holding features may release in response to an application of energy to the wires that melt or soften the holding features. An additional approach is to have a mechanical pull or feature that the user can pull that releases the wires from the holding features. The mechanical pull or feature may be separate strings attached to the holding features that the user can access near the opening of the bag when exteriorized. Inflatable features within the bag itself may also be used to rupture the holding features.

One potential risk of temporarily attaching wires to the bag is that the bag ruptures during detachment of the wires. The use of multiple bag layers will help to ensure that the bag remains intact upon release of the holding features. The holding features are attached to the most inner layer of the bag, with one or more additional layers on the outside of the bag to ensure the bag remains intact and impermeable to fluids.

Additional features may be added that provide feedback to the user regarding bag integrity. The bag may be inflated or have inflatable channels. With inflation, the measured inflation pressure that the bag or inflatable channels holds is an indication of any possible holes in the bag. Use of a pressure valve with a sensor can be used to detect any drop in pressure. The pressure valve and/or means to inflate the bag or inflatable channels may be integrated into the bag or alternatively be integrated into the segmentation instrument itself. Other potential approaches include use of a camera to allow the user to view the outside of the bag during the procedure, use of a color changing indicator within the outer two layers of a three layer bag that changes color upon contact with bodily fluids, or use of clear outer bag layers or films where the user can visually determine if any fluids have penetrated between the two layers. Another method could be to have a conductive deposition on the inside of the outer bag layer and a center layer that is separated to the outer layer by the inflation. The capacitance between the two conductive layers can be monitored such that a drop in pressure will change the capacitance reading, similar to a capacitive touchscreen press. The capacitance can be measured at regular intervals, on command or continuously or a threshold can be predetermined such that if the pressure is lost, the system can identify the condition and issue an alert. The two conductive layers can also be used in a similar manner as a resistive touchscreen in that the change in resistance between the two layers can be used to indicate a loss of pressure condition. Lastly the outer two layers of the bag may contain a sterile fluid by which the user can be confident of bag integrity if the fluid level has not fallen during the course of the procedure.

If the user visually determines a void in the bag, an adhesive patch may be applied in situ to reduce the risk of bodily fluid or tissue loss from the bag contents. The user may also decide to wash (rinse and suction) the patient's body cavity.

Although this document primarily addresses electrosurgical systems, it should be understood that tissue segmentation and removal may, in some embodiments, but achieved using a segmentation device that does not have an electrosurgical component. Specifically, a surgical device having one or more wires that segment tissue mechanically, such as by force, motion, and/or vibration may be provided. Many of the examples disclosed herein also apply to such a mechanical surgical device. For example, a surgical device may utilize wire tensioning methods disclosed herein without the electrical aspects, and with or without a controller configured to control the pull forces or speed of cut. Similarly, the robotic system may also provide a cutting function that is not electrosurgical in nature. As in the case of the electrosurgical segmentation procedure, the removal bag may provide means for keeping the cutting wires in place (and from entangling with each other) while a tissue segment is placed in the removal bag, and, similarly, the wires may be configured to detach from the removal bag at a desired set force or time. The use of mechanical only cutting may be advantageous in applications where the tissues are not calcified, have less variability of mechanical properties, or are generally more friable, and therefore do not require extremely high forces to cut reliably through the tissues. To address this case, the tissue removal device or wire cutting device may be configured without the elements that are required for electrosurgical cutting; for example the return electrode or connections to the controller or an electrosurgical generator may be omitted. Those skilled in the art will understand that a removal device without the electrosurgical cutting elements requires a smaller number of user completed instrument connections. In turn, this may lower the production costs of the product. In some embodiments, a removal device that does not have an electrosurgical cutting feature allows for cutting tissue at a lower temperature, and may be a safer alternative for weaker patients. Those skilled in the art will understand that the mechanical pull force(s) in a removal device without electrosurgical cutting will be significantly greater than one with an electrosurgical cutting feature.

Figure 89:
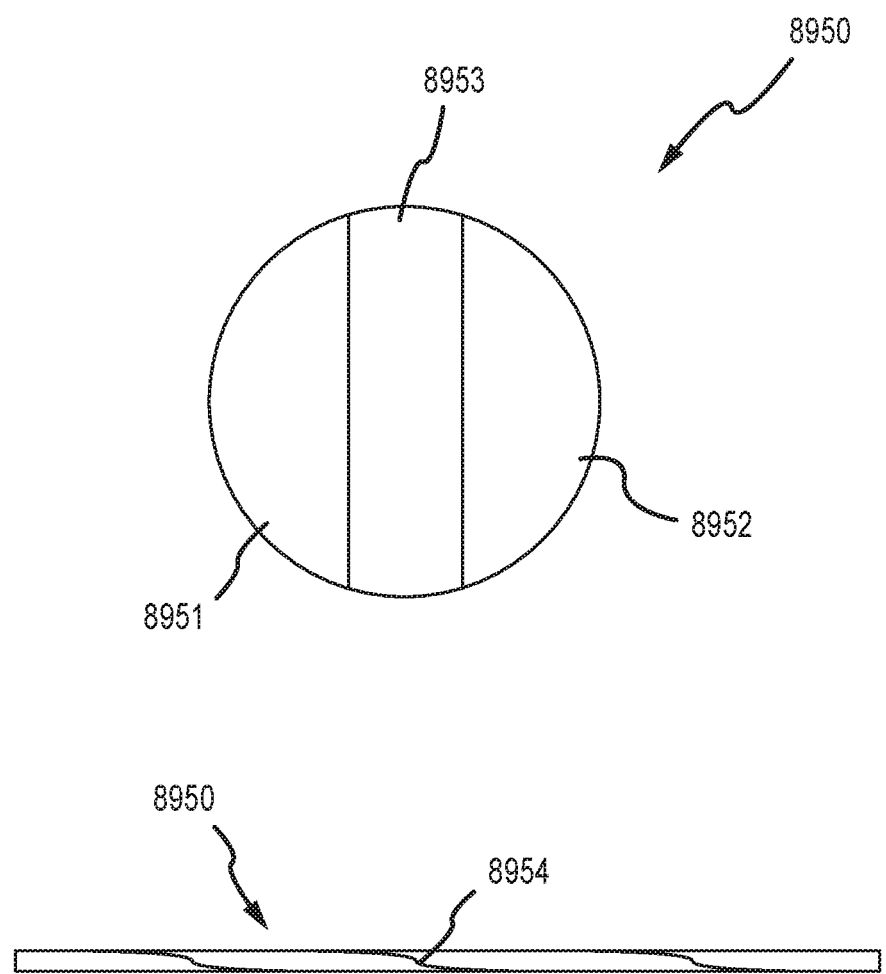
FIG. 89 illustrates details of a wire.

As was previously mentioned in U.S. patent application Ser. No. 14/805,358, there may be some benefits to a bipolar application of RF energy. Figure FIG. 89 illustrates an embodiment of a bipolar wire assembly 8950. The wire is created with two electrically conductive outer regions 8951 and 8952 that are separated by an insulation member 8953. The two conductive regions 8951 and 8952 are not electrically coupled, and the separation of the insulation member 8953 is such that the voltage applied to perform the tissue segmentation does not arc across the insulation member. The RF voltage may be applied between conductive regions 8951, 8952 with one acting as an active electrode and the other active as a return electrode. In some the optimal embodiments, the conductive regions 8951, 8952 and the insulation member 8953 are bonded or formed such that they are mechanically coupled and they are twisted 554 over the length of the wire assembly. This twisting ensures contact of both conductive regions 8951, 8952 with the tissue at some point across the tissue specimen. The initiation of the cut will happen at some point across the length of the wire assembly and as the wire advances into the tissue during the cut, contact will be made over the entire length of the wire. Configuring the device as described here may increases the probability that both conductive regions will remain in contact with the tissue through the completion of the cut.

Figure 90:
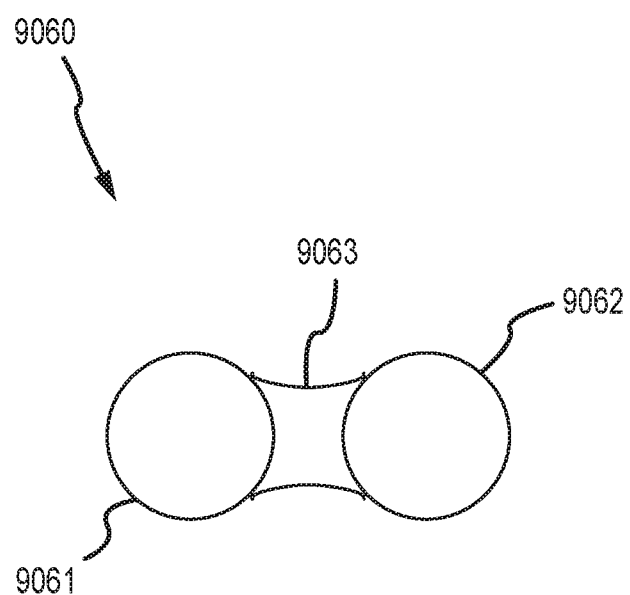
FIG. 90 illustrates details of another wire.

FIG. 90 illustrates a bipolar wire assembly 9060 having two parallel wires 9061, 9062 separated by an insulation member 9063 mechanically bonded or formed together to create a mechanical coupling. This configuration may be left in parallel or twisted as described with respect to FIG. 89.

As previously described herein, rupture of the bag 161 is a potential failure that should be monitored, prevented, and/or mitigated, whether with a tissue segmentation device or simply with a removal device that does not segment tissue.

Figure 91:
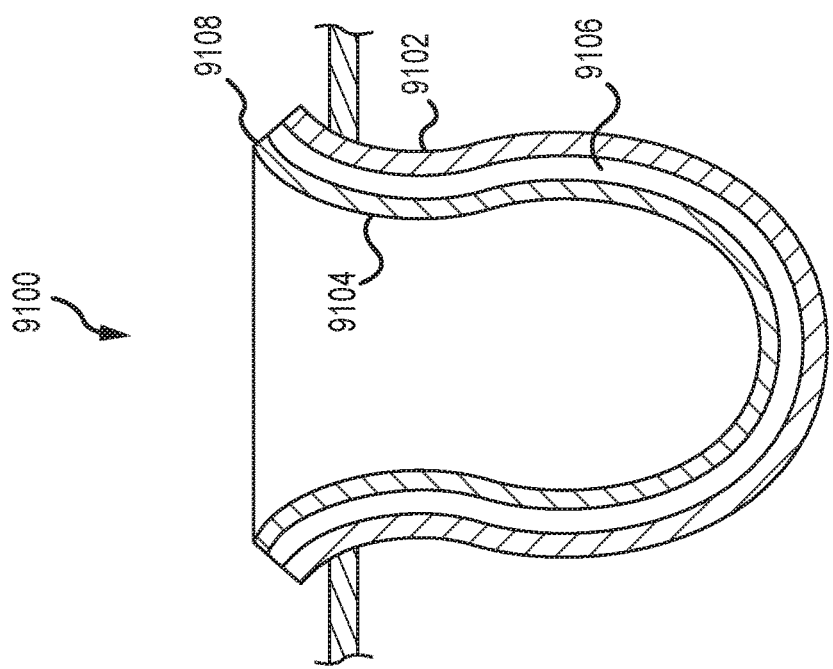
FIG. 91 is a cross-section view of some components of a bag assembly with leak detection.

With reference now to FIG. 91, a removal bag system 9100 may be provided that includes an outer bag layer 9102, an inner bag layer 9104, and a space 9106 therebetween. The layers 9102, 9104 may be coupled to or fused to one another using any means known in the art, such as at a joint 9108. Either vacuum or pressure between the bag layers 9102, 9104 may be used as part of a breach detection or mitigation strategy.

In some embodiments, pressure in the space 9106 between the layers 9102, 9104 may be used to inflate the outer bag layer 9102. If a breach occurs in the outer bag layer 9102, the loss of pressure can be detected visually by looking for a decrease in inflated bag size or pressure.

In some embodiments, a vacuum may be applied to the space 9106 between bag layers 9102, 9104. The vacuum may serve two purposes: first, a vacuum may provide a visual indication of a breach if the outer bag layer 9104 no longer appears to be pulled towards the inner layer 9104. Second, if a breach occurs in the outer bag layer 9104, the vacuum will draw air into the space between the bag layers 9102, 9104 thereby minimizing the potential for other materials or fluids to escape the hole (in particular if the hole is small). That is, a vacuum in the space 9106 between layers 9102, 9104 may tend to bias an inward flow of fluid, whereas a pressure in the space 9106 would tend to, in the event of a breach, release fluid out and potentially into the patient.

Figure 92:
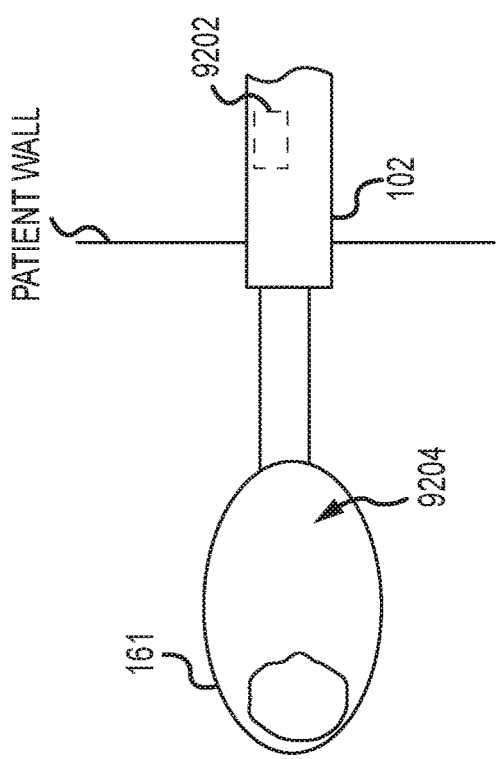
FIG. 92 is a side partial section view of some components of a bag assembly with leak detection.

In some embodiments, and as is illustrated in FIG. 92, the removal device 102 may include a CO2 and/or N2O sensor, positioned, for example in the introducer tube, to detect the presence of the gas being used for insufflation. That is, for example, if the bag 161 is introduced into the patient cavity in a vacuum state or with atmospheric air therein, the gas used for insufflation, such as carbon dioxide or nitrous oxide, will tend to enter the interior space 9204 of the bag 161, and the sensor 9202 may be provided and configured to detect the change in the gas signature and/or to detect that the gas in the interior space 9204 has insufflation gas therein. Those skilled in the art will recognize that the sensor 9202 does not necessarily need to be inside the removal device 102 but merely needs to be exposed to the interior space 9204 for sampling, using any suitable means known or as-yet developed in the art.

Figure 93:
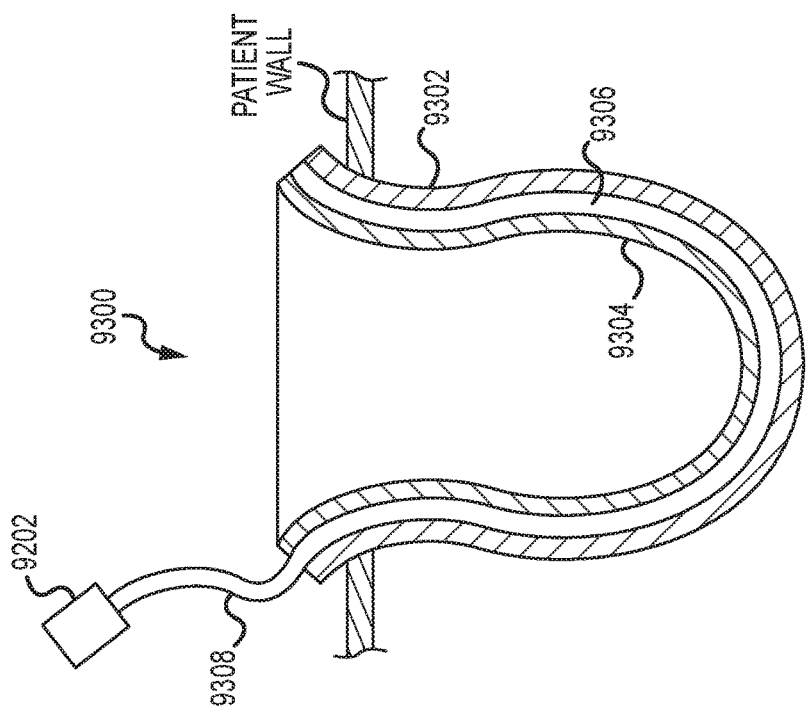
FIG. 93 is a side section view of some components of a bag assembly with leak detection.

Turning now to FIG. 93, in some embodiments having multiple bag layers, a tube (not illustrated), lumen, or channel 9308 may be provided to expose the sensor 9202 to the intermediate space 9306 between the outer and inner layer bag layers 9302, 9304. The sensor 9202 may be positioned remotely from the bag assembly 9300, and coupled to the channel 9308 such that the sensor 9202 may sample the contents of the air in this intermediate space 9306.

In some embodiments, a slight vacuum may be applied to the space 9106, 9306 between layers 9102, 9104, 9302, 9306 or the bag interior 9204, such that the content of gas being detected at the sensor 9202 is increased, thereby providing a more accurate indication of a leak. This slight vacuum may be created using a pump (not illustrated), evacuated air cylinder or other means to apply a negative pressure, including, but not limited to, an air flow control valve coupled with the sensor 9202 to draw the contents of the space 9106, 9306, 9204 toward the sensor 9202 and ensure that the negative pressure can be maintained throughout the procedure.

Figure 94:
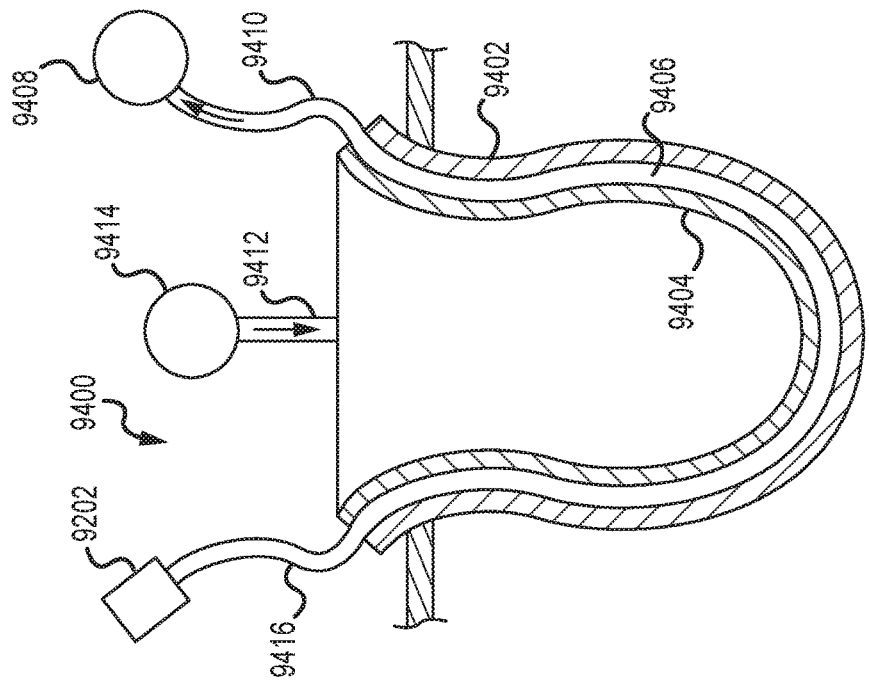
FIG. 94 is a side section view of some components of a bag assembly with leak detection.

As illustrated in FIG. 94, in some embodiments, one or more channels 9410, 9412 may be provided and coupled to the intermediate space 9406 between the outer and inner bag layers 9402, 9404. A first channel 9410 may be coupled to a vacuum pump 9408, and used as previously described to provide a negative pressure to sample the contents of the intermediate space 9406. A second channel 9412 may be provided to resupply the space 9406 with the air that has been pulled out of the space 9406 or other air. In this manner, a circulation of air is created that may be continuously monitored, such as at the sensor 9202 using one of the channels 9410, 9412 previously described or another channel 9416.

Figure 95:
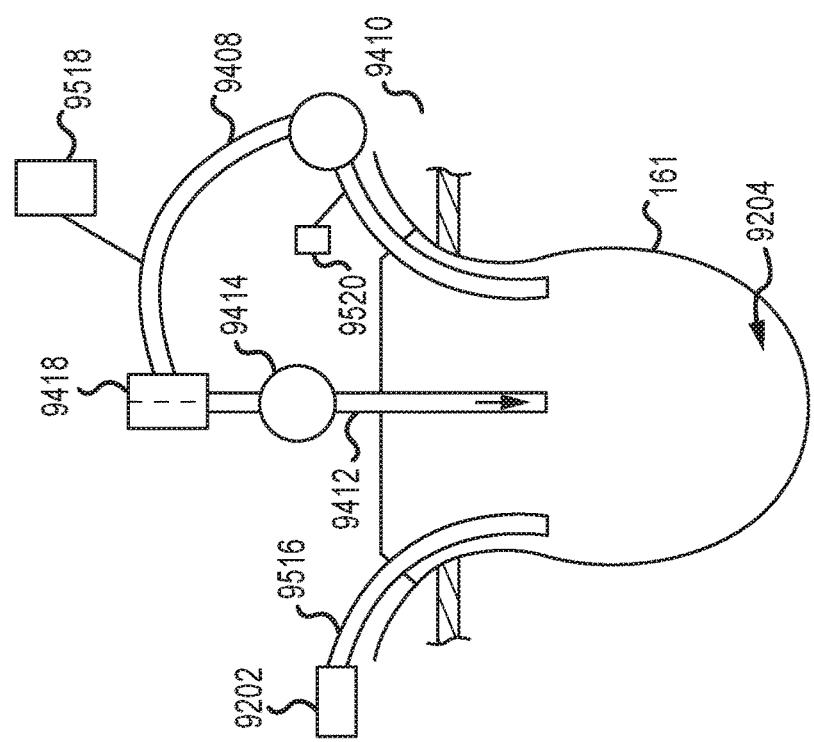
FIG. 95 is a side section view of some components of a bag assembly with leak detection.

This monitoring may establish a baseline and/or provide a more accurate indication of the starting level of $CO_2$ and/or $N_2O$. The sensor 9202 may, in some embodiments, monitor for differential or changing levels of $CO_2$ and/or $N_2O$ as previously mentioned herein. In some embodiments, the bag system 9500, as illustrated in FIG. 95, may include a HEPA, carbon, and/or other filter to condition or maintain the air quality of the space 9204 being monitored. For example, if the channels 9410, 9412 are coupled to the interior of the bag 161, any steam, smoke or other effects that are created from the cutting process may be reduced significantly within the bag area 9204.

The sensor 9202 may be used independently and/or may include a visual or audible indication when $CO_2$ and/or $N_2O$ is detected. The sensor 9202 may also be electrically coupled to a processing unit such as the controller 108, 808 that can create an audible or visual indication to the user when $CO_2$ and/or $N_2O$ is detected. The sensor 9202 may also be electrically coupled to the instrument 102 or may be coupled to a separate device that is dedicated to detecting the presence of a leak in the bag 161, 9100, 9300.

An alert provided to the user upon indication of $CO_2$ and/or $N_2O$ may allow the surgical team to perform surgical intervention at the earliest possible opportunity to best manage the outcomes for the patient.

In some embodiments, and as illustrated in FIG. 95, one or more sensors 9518, 9520 provided in-line with the pumps 9408, 9414 may be configured to monitor the quality of a fluid being introduced into and exiting from the bag 161, or space between two bags 9302, 9304. That is, the system 9300, 9400, 9500 may be configured to detect a change in gas that is in the interior space 9204 or space 9106, 9306, 9406, 9506. A method of leak detection may include comparing one or more fluid quality values detected at a first point in time with one or more fluid quality values detected at a second point in time.

The system 100 may use this information to alert the user of a leak as it occurs to allow the surgical team to perform surgical intervention.

With continued reference to FIGS. 91, 93, 94, and 95, in some embodiments, a high pressure air or fluid may be applied to the space 9106, 9306, 9406, and an acoustic or ultrasonic wave in the range of 20-50 kHz may be applied to the pressurized structure. An acoustic transducer (not illustrated) may be provided to monitor the acoustic emissions of the structure and detect changes in the emissions that would be indicative of a leak or change in the structure. The acoustic emissions detection utilize one or more of the following techniques: ringdown counts, energy analysis, amplitude analysis, frequency analysis, pattern recognition, and/or spectral analysis to detect the change in acoustic emissions, or any other means known to those skilled in the art.

In some embodiments, a post-surgical procedure leak detection method is provided. For example, fluid pressure may be applied from a pump, cylinder, or other means to the space 9106, 9204, 9306, 9406 between the outer and inner bag layers or to the inside of the bag 161 with the bag 161, 9100, 9300, 9400 sealed around the air pressure device. A pressure detector may be used to measure the resulting air pressure, and/or decay characteristic. A visual indication to determine if a leak has occurred may also be provided.

The detection system may include a pressure detector, a pressure-control valve to limit the applied pressure and a vent mechanism. For embodiments that use the intermediate space, the lumen that provides access to the space can have a fitting that allows easy attachment of the leak detection system by the user. For embodiments that use the bag opening, an interface that fits into the bag opening and allows the user to constrict the opening onto the interface creating a seal. The bag may also have features that aide in creating a seal against the interface to improve the ability to perform the test.

The post-surgical leak detection method may allow the surgical team to perform a surgical intervention, if necessary, prior to completing the surgery.

In some embodiments, a leak detection method may include a fluid wash (such as sterile saline) between the bag layers after usage. The contents of the fluids may then be evaluated for biologic materials such as blood.

In some embodiments, a post-surgical leak detection method may include inflating a bag and placing under a liquid such as water to look for bubbles.

In some embodiments, after completion of the segmentation procedure, the specimen bag may be evaluated for leaks. For example, the operating room air supply may be used to fill the interior of the used specimen bag by hand grasping/sealing the bag opening around the air supply while inflating. Once the specimen bag is inflated, the opening may be twisted around itself to seal in the pressurized air. This inflated specimen bag may be (partially) submerged in a bath of water (i.e. a small cavity of the tray in which the specimen bag was shipped) to visually inspect for air bubbles escaping any breaches in the specimen bag. A surfactant may be added to the bag surface or water bath to modify the surface tension of the water and enhance the visible bubbling of the water.

Some embodiments of leak detection may include filling the intermediate space between bag layers or the interior of the specimen bag with a liquid, such as water or saline, and adding pressurized air to a predetermined pressure, thereby accelerating any leaks through any breech in the bag or bag layers.

In some embodiments, the bag surface may be visually inspected and/or may be dried with a towel or air, and migration of the liquid across the bag layer boundary may be visually inspected.

In some embodiments, a coloring agent or dye may be provided in the fluid introduced into the space, to enhance the ability to visually identify the migration across the bag or bag layer boundary.

In some embodiments, an outer bag layer 9102 may be made of a first translucent color and an inner bag layer 9104 may be made of a second color, and a space 9106 therebetween may be pressurized. A method of determining a leak may include visually determining a perceived change in color at one or more points of contact between the bag layers 9102, 9104. Visually determining may include using an endoscopic camera or viewing the outer layer 9104 during or after the surgical procedure.

For example, if the inner bag layer has a blue tint applied, and the outside layer has a yellow tint applied, the area of contact will result in a green tinted shape due to increase in optical coupling of the two colored layers.

In some embodiments, as the surgical procedure proceeds, a change is the size of the combined color area, particularly an increase, may indicate a change in the area of contact between the two layers. If a fixed volume of air is captured between the two layers in this intermediate space or if a slight pressure is applied prior to use, the increase of size of this color combined region can identify a leak of one of the bag layers.

Those skilled in the art will recognize that the procedure described above may also be suitable where a space 9106 between the layers is under vacuum. For example, if the layers 9102, 9104 pull away from each other, a leak is also indicated.

Figure 96:
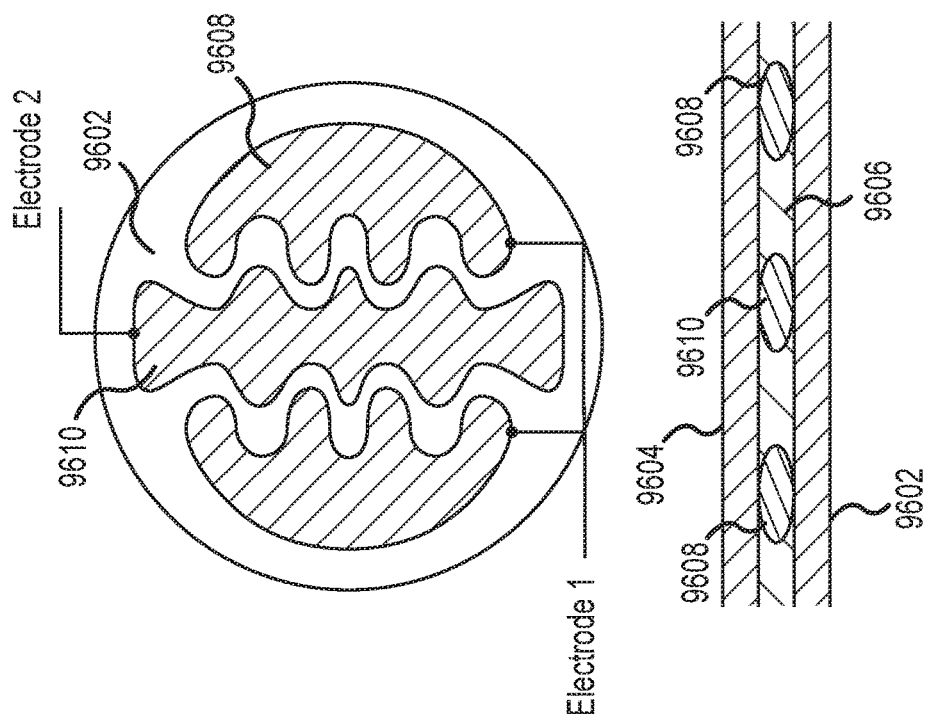
FIG. 96 illustrates partial top and side section views of some components of a bag assembly with leak detection.

In some embodiments, a method of leak detection may include providing a moisture detection layer, and/or monitoring an electrical pattern indicative of conductive fluid or change in impedance due to fluids As illustrated in FIG. 96, which illustrates a side section view and a partial top view, a method of detecting a leak, such as of the inner layer may include providing an electrically conductive mechanism 9606 in the intermediate space between the inner bag layer 9604 and outer bag layer 9602. The mechanism 9606 may be a conductive film or mesh, and/or may be a coating or layer deposited or printed onto the outer surface in the inner bag layer 9604 and/or the inner surface of the outer bag layer 9602.

In some embodiments, a first electrode 9608 and a second electrode 9610 may be positioned between the layers 9602, 9604 with or without the rest of the conductive mechanism 9606 or mesh.

The conductive mechanism 9606 may be in a pattern having a fixed spacing between two separate electrodes 9608, 9610. The two electrodes 9608, 9610 may be a single pair of electrodes that cover some or most of the internal surface of the bag layers or may be pairs placed at multiple locations that are electrically connected in parallel. The electrodes may be electrically coupled to a signal, preferably an AC waveform similar to the dual electrode monitoring interrogation waveform applied by electrosurgical generators to monitor return electrode contact quality. The signal may be generated from an electrical circuit located in the segmentation instrument 102, the monitoring unit or controller 108, or a separate remote location. The characteristics of the voltage measured across the electrodes and the current measured between the electrodes can provide the impedance across the electrodes. If the intermediate space is dry, the impedance will near an open circuit and be characteristic of the bag layer material conductance with the spacing of the two electrodes. If the inner layer leaks, then fluids or other material may enter the intermediate space. This fluid or foreign material will provide a change in the impedance due to the conductivity of blood, tissue or other body fluids. By measuring a reduction in the impedance between the two electrodes, a leak of fluids or other tissue that spans the electrode spacing can be detected.

Some embodiments of leak detection include measuring complex impedance, such that a short circuit created with bag folds or other means may be distinguished from the introduction of fluids or other bodily fluids or material by using the power factor angle. This could also be enhanced with adding a positive pressure to the intermediate space to reduce the chance of bag folds as well as designing the electrode shapes to align with areas of the bag that are expected to have folds so that a folded bag may cause an electrode to contact itself and not contact the opposing electrode.

Since bodily fluids of a significant amount are likely to fall to the bottom of the bag, an electrode or series of electrodes at bottom of bag can be used to detect when a fluid comes into contact with the electrodes or circuit. The electrodes may sense a resistance or capacitance. For example, the electrodes may have a liquid absorbing gel in the bottom of bag that changes capacitance if liquid is added.

Some embodiments of detecting a leak in the bag may include applying a volume of Helium (He) or inert gas into the contained intermediate space between the inner and outer layers of the bag. Using a gas spectroscopy detection technique, a helium detector, or an inert gas detector, placed within the bag, incorporated into the instrument such that the sensor is located within the introducer tube or located outside of the tube with a lumen connected to the introducer tube such that the sensor can sample the contents of the air flowing from inside the bag, such as in a smoke evacuation system. Any traces of helium or the inert gas indicate migration of the gas from the intermediate space to the inside of the bag which in turn indicates a leak has occurred.

In some embodiments, the detector is placed through an additional laparoscopic port such that any detection of helium or inert gas within the peritoneal cavity would indicate a lead between the intermediate space of the bag and the outer bag layer. This method may include suspending the insufflation while measuring for a leak.

Some methods of leak detection may include optically scanning for a leak during or after the surgical procedure.

Some embodiments of leak detection methods include using a camera to view the surface of the bag during the procedure. The camera may be inserted through a separate port and may be the endoscopic camera used during laparoscopy, or could be a separate camera intended to detect leaks. The image of the camera may be sent to a processing unit, such as the controller previously described herein or a different unit that can digitize the image in real time. The processing unit may also contain a datastore to store digitized images that can be used to compare real time imaging data. This comparison can be used to determine changes in the geometry of the bag as the procedure proceeds, such as the intermediate space thickness, which can provide an indication of a bag leak. The visual image can also look for a buildup of fluids on the surface or bottom of the bag, can look for drops forming or falling from the bag and can be used in conjunction with some of the other embodiments presented in this disclosure. For example, if a material is placed within the intermediate space that has a particular color, a filtering algorithm can be used by the processor to identify changes in amplitude of this color on the outer surface of the bag.

Some embodiments include comparing a bag after the procedure is complete to a measurement taken before placement of the bag into the patient or to manufacturers' specifications.

Figure 97C:
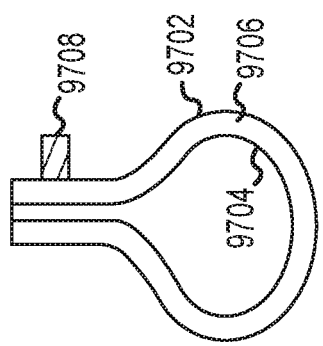
Figure 97B:
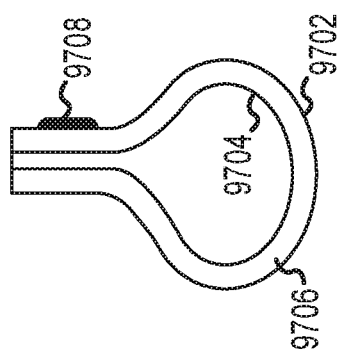
Figure 97A:
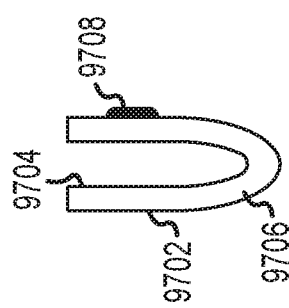
FIG. 97a illustrates side section views of some components of a bag assembly with leak detection.

With reference now to FIGS. 97a-97c, some embodiments of leak detection include providing or using an audible or visual indicator 9708 that expands or "pops" when a vacuum pressure in a space 9706 between two bag layers 9702, 9704 is lost (compare to a canning jar lid that pops when opened). For example, if a breach in either the inner or outer bag 9702, 9704 occurs, the vacuum loss indicator 9708 feature will pop, extend, or change from a first state of tension to a second state, to indicate to the surgeon that a breach in either layer of the bag has caused the void space between the two layers of specimen bag to lose its vacuum.

Some embodiments of leak detection may include providing or using a color changing moisture indicator between bag layers. For example, the specimen bag layers may be constructed of two welded layers of polyurethane, creating a sealed inner space between the two layers. A compromise or leak in either of these two layers may be indicated by a color changing chemical agent that would be applied to the inner space during bag construction. When the chemical indicator comes in contact with water based, human fluids a chemical reaction with the fluid would create a color change in the agent that would be observable either from the endoscopic camera in the body cavity or observable directly by the surgeon after bag removal. The agent may be sprayed on to either or both inner walls of the polyurethane during assembly of the bag. The agent may also be inserted in construction as a loose powder or as a film of liquid. Strips of colored paper or fiber may hold the color changing agent.

In some embodiments, a liquid agent may be inserted through a port after the bag is placed in the body. A color change between the two layers would only indicate that, at least, one of the two layers had been compromised since fluids could have passed from either side into the inner space. A follow up test may be useful to verify which of the layers had been perforated.

In some embodiments useful for leak detection, a spray-on coating on an internal surface of the outer bag may be provided and configured to bind to liquid. After the procedure, a visual inspection of the outer surface of the inner bag and/or the inner surface of the outer bag, using, for example, black light, may reveal if a leak has occurred.

To identify liquid escape from a breached inner bag layer, a coating on the outer-side of the inner specimen bag layer. This coating, when combined with bodily fluid, may be configured to bind with the infiltrating fluid, thereby creating a marker which may be visualized with the naked eye, and/or with the aid of secondary equipment, such as a black light. Inspection for a breach in the inner bag layer may be incorporated as a procedure after every specimen removal procedure by scanning each post-operative bag to look for the presence of this breach marker.

Some embodiments of leak detection methods and devices may include using a water color "no mess" markers pad that changes color in the presence of liquid. That is, to visually indicate a breach in the inner bag layer, a coating, similar to a dry watercolor pigment, may be applied to the void between the inner and outer bag during specimen bag manufacturing. If this void is breached & body fluids infiltrate this void space then the dry pigment will become saturated and provide a visual identification of a breached inner bag layer.

Some embodiments of leak detection methods and devices may include a finger print "dust" for leak detection. Similar to the watercolor pigment method and device described above, a powder may be inserted in the void space between the two layers of the specimen bag. Infiltration of body fluids into this space would turn the powder to a paste-link substance. This paste substance would make a visual identification of a breached inner bag layer possible.

In some embodiments, a color changing material may be used as one of the bag layers or in addition to and between the bag layers. If either of the bag layers is breached, the color changing material would change colors as a visual indication of the breach. For example, the material in between layers changes color when $CO_2$ or $N_2O$, which are typical insufflation gases, enter the space between the bag layers.

Some embodiments include using a color changing material at the bottom of bag only that absorbs any fluids that are within the layers. This color changing material may be configured to change color as a result of a protein, fluid, or other chemical signature of a biologic fluid.

Some embodiments of leak detection methods or devices include the use of a visual indicator, which may be with or without a camera between layers. To provide a visual indication of whether or not a breach occurred in the inner bag, the outer bag layer may be made of a white or similarly contrasting material such that the surgeon can look for blood on inside of outer white layer either during the instrument, use such as with a camera, or after use. Discoloration of the outer bag inner surface may indicate that a breach of the inner bag layer has occurred.

Some embodiments of leak detection devices 9700 and methods may include the use of one or more vacuum loss indicators, such as indicator tubes or geometries, as illustrated in FIG. 97. For example, one or more pockets, tubes or expansion members 9708 may be positioned at locations around the outer layer 9702 of the bag assembly. One or more expansion members 9708 may be non-distinct in a normal relaxed state, and, under normal conditions, with a fully contained and pressurized bag assembly, the geometries would remain in the relaxed state. If a leak occurs, however, in the inner bag layer 9702, the expansion member 9708 on the outer layer 9702 would expand, providing an easily identifiable indication of an inner bag layer leak.

Embodiments of leak management are also described herein, to mitigate any adverse effects that may be caused by a leak. For example, in some embodiments, a chemotherapy agent specific to the procedure being performed may be placed in the interior space of the bag 161. The agent may be pre-placed into the bag, such as during manufacturing or pre-packaging of the bag, or the agent may be positioned in the bag in-situ.

In some embodiments, a chemotherapy agent in the space between the bag layers may be configured to kill cells on contact. The agent may be a specific agent that is chosen or configured to target the intended procedure.

In some embodiments, the agent is contained in a hydrogel or gel such that any cells that come into contact with the agent are likely to stick or adhere to the surface of the hydrogel or gel.

The chemotherapy agent may be selected based on the procedure and/or patient history. For example, if a uterus is being removed, a chemotherapy agent that would be indicated for a leiomyosarcoma suitable for the patient may be used to best address any cancer cells that may migrate into the interior space of the bag or the space between bag layers.

For colon removal an agent that is indicated for an adenocarcinoma may be selected and placed in the bag.

In some embodiments, the surgeon and/or oncologist selects the chemotherapy agent and adds the agent to the space between the outer and inner layers just prior to use.

In some embodiments, the surgeon and/or oncologist may select from a range of pre-administered chemotherapy agents that are placed in the bag or between bag layers during manufacturing. The agent maybe applied in the form of a liquid with a safe quantity applied or may be applied as a film to either the outside layer of the inner bag or the inside layer of the outer bag.

In some embodiments of leak mitigation, an antiseptic or disinfectant solution of layer may be provided in a manner substantially similar to that described with respect to the chemotherapy agent previously described herein.

Some embodiments of leak mitigation include placing or using a layer of absorbent material in between the inner and outer bag layers such that if a leak occurs in the inner layer, the absorbent material will contain an amount of fluids or other material that breach the inner layer. This also provides some protection to resist both layers of the bag being damaged by instruments or other mechanical edges. The absorbent material may be a fabric, a foam, gel or other material that has highly absorbent properties to water.

Some embodiments of leak mitigation include providing or using an absorbent material that changes hardness or phases when in contact with a fluid. The material may be placed between the bag layers. It may be a dry substance that turns to a gel in some embodiments. In some embodiments, the substance may turn harder or softer, may be a powder or film that turns to a gel, or may change colors as a result of a chemically activated change. The material may change phases so as to be detected either visually, through physical palpation of the bag, etc.

Some embodiments of leak mitigation may include the use of or placement of a layer of viscous gel material between the inner and outer bag layers such that, if a leak occurs, the gel is configured to minimize the impact of a leak. The gel may, in some embodiments, close the leak; in some embodiments, the leak may increase the thickness of the bag such that a leak would have a lower probability of penetrating both the inner and outer bag layers and the gel layer. In some embodiments, the gel may be made of or include a biocompatible material. In some embodiments, the gel may include a hydrogel, such as that placed on return electrodes. In some embodiments, the gel includes a hydrophilic polymeric material, a biodegradable hydrophilic material, and/or an organic hydrophilic material. The gel may be added to the space between layers at manufacturing; or the gel may be added through a lumen in-situ.

The gel may be selected and configured to thermally insulate the outer layer from the inner layer, thereby reducing the likelihood of a breach of both layers.

Some embodiments of leak mitigation include the use of a multi-cell intermediate layer. A multi-cell layer between the outer bag layer and the inner bag layer may include a number of interior spaces that serve to reduce the volume of fluid that may potentially leak in the event the inner layer is compromised. For example, a number of walls coupling the inner layer and the outer layer may form a number of smaller fixed volumes of air, fluid, gel, or other leak mitigation or leak management means described herein within the space between the inner and outer layers of the bag.

In some embodiments, the smaller fixed volumes of air fluid, gel, or other leak mitigation or leak management means described herein may be provided by a third bag layer positioned between the inner layer and the outer layer. The third layer may include an inner wall, an outer wall, and a number of connecting walls coupling the inner wall and the outer wall, creating the fixed volumes therebetween.

In some embodiments, a multi-cell layer may include a plurality of sealed pockets of a fluid or a leak mitigation means. The multi-cell layer may be positioned between the inner layer and the outer layer. The multi-cell layer may limit travel of contaminated material and reduce the probability of contaminated material such as portions of a cancerous segmented tissue sample breaching the bag assembly. The multi-cell layer may be positioned exterior of both bag layers in some embodiments.

Some embodiments of leak mitigation may include the use of a material that solidifies when it comes in contact with bodily fluid. For example, an epoxy or any thermosetting material may be provided in the space between the outer and inner bag layers. The thermosetting material may be configured to solidify or harden in the event a breach of the inner bag layer allows material to reach the intermediate space. In some embodiments, the solidification may plug the breach. In some embodiments, the thermosetting material may be selected or configured to set within a period of time. The period of time may be five minutes or less in some embodiments. The period of time may be two minutes or less in some embodiments. The period of time may be one minute or less in some embodiments. The period of time may be thirty seconds or less in some embodiments. The period of time may be fifteen seconds or less in some embodiments.

Those skilled in the art will recognize that a faster setting of the thermosetting material may result in a weaker bond; however, this feature may be advantageous by enabling the surgeon to, after completing the segmentation procedure, break up the set materials and remove them through the incision site. Breaking up the set materials may be achieved without destroying the outer bag layer in some embodiments.

In some embodiments, a material that is reactive with carbon dioxide and/or nitrous oxide may be used or placed in the space between the outer and inner layers. The reactive material may be selected or configured to form a foam or gel, or to solidify, thereby mitigating the effects of any breach of the inner bag layer.

Embodiments

1. A tissue removal bag assembly, comprising: an inner bag layer having an interior surface and an exterior surface; an outer bag layer having an interior surface and an exterior surface, the outer bag layer coupled to the inner bag layer and forming a space between the exterior surface of the inner bag layer and the interior surface of the outer bag layer.

2. The assembly of embodiment 1, further comprising: a sensor exposed to the space, the sensor configured to detect pressure in the space.

3. The assembly of embodiment 1 or 2, further comprising: an inflation mechanism coupled to and configured to inflate the space between the inner bag layer and outer bag layer.

4. The assembly of embodiment 1-3, further comprising: a color changing indicator responsive to and configured to indicate a breach in the inner bag layer.

5. The assembly of embodiment 1-4, further comprising: a conductive deposition between the outer bag layer and the inner bag layer, the conductive deposition configured to indicate a breach in the inner bag layer.

6. The assembly of embodiment 1-5, further comprising: a fluid in the space.

7. The assembly of embodiment 1-6, further comprising: a sensor exposed to the space, the sensor configured to detect at least one of carbon dioxide or nitrous oxide.

8. The assembly of embodiment 1-7, further comprising: a vacuum loss indicator configured to indicate a loss of negative pressure between the outer bag layer and the inner bag layer.

9. The assembly of embodiment 8, wherein: the vacuum loss indicator comprises an expansion member, the expansion member configured to move from a compressed configuration to an expanded configuration in response to a loss of negative pressure between the outer bag layer and the inner bag layer.

10. The assembly of embodiment 1-9, further comprising: at least one of a hydrogel, a chemotherapy agent, or an absorbent material positioned between the outer bag layer and the inner bag layer.

11. The assembly of embodiment 1-10, further comprising: a plurality of sealed pockets positioned between the outer bag layer and the inner bag layer.

12. The assembly of embodiment 11, further comprising: a plurality of walls coupling the outer bag layer to the inner bag layer to form the plurality of sealed pockets.

13. The assembly of embodiment 11, further comprising: a third bag layer, the third bag layer having an inner wall, an outer wall, and a number of connecting walls coupling the inner wall and the outer wall and forming the plurality of sealed pockets.

14. The assembly of embodiment 11-13, wherein: at least one of the plurality of sealed pockets contains at least one of air, a fluid, a gel, a hydrogel, a thermosetting material, an absorbent material, a chemotherapy agent, or a color changing material.

15. The assembly of embodiment 1-10, further comprising: a third bag layer, the third bag layer having an inner wall, an outer wall, and a number of connecting walls coupling the inner wall and the outer wall and forming the plurality of sealed pockets.

16. The assembly of embodiment 15, wherein: the third bag layer is interior of the outer bag layer.

17. The assembly of embodiment 1-16, further comprising: a thermosetting material positioned interior of the outer bag layer and configured to solidify when exposed to bodily fluid.

18. The assembly of embodiment 17, wherein: the thermosetting material is configured to solidify within a period of time of exposure to the bodily fluid.

19. The assembly of embodiment 18, wherein: the period of time is one minute or less.

20. The assembly of embodiment 1-19, further comprising: a color changing indicator positioned interior of the outer bag layer, the color changing material having a material selected to change from a first color to a second color in response to exposure to at least one of nitrous oxide, carbon dioxide, or bodily fluid.

21. The assembly of embodiment 1-20, wherein: the outer bag layer has a first color; the inner bag layer has a second color; and wherein contact between the outer bag layer and the inner bag layer results in a third color observed.

22. A tissue segmentation device having at least one active electrode, a return electrode, a mechanical force application mechanism, a voltage sensor, a current sensor, and a controller. The controller is configured to control a power output of the segmentation device. The controller has a processing component, responsive to the voltage sensor and the current sensor, configured to execute the following: (a) derive a power factor of power applied to the at least one electrode; and (b) responsive to the deriving a power factor, assign a circuit status to a circuit comprising the at least one electrode, according to the following: IF (PF≈0) and ((Vrms/Irms)≥T), THEN the circuit status is "open". IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

23. A controller for a tissue segmentation device having at least one active electrode, a return electrode, a voltage sensor, a current sensor, and a mechanical force application mechanism. The controller has a processing component, responsive to the voltage sensor and the current sensor, configured to execute the following: (a) derive a power factor of power applied to the at least one electrode; and (b) responsive to the deriving a power factor, assign a circuit status to a circuit comprising the at least one electrode according to the following: IF (PF≈0) and ((Vrms/Irms)≥T), THEN the circuit status is "open". IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

24. A method of tissue segmentation. The method includes providing a tissue segmentation device having at least one active electrode, a return electrode, a mechanical force application mechanism, a voltage sensor, and a current sensor. The method includes deriving a power factor of power applied to the at least one electrode, and responsive to deriving a power factor, assigning a circuit status to a circuit comprising the at least one electrode according to the following: IF (PF≈0) and ((Vrms/Irms)≥T), THEN the circuit status is "open"; IF (PF≈0) and ((Vrms/Irms)<T), THEN the circuit status is "short". PF is the power factor. Vrms is the root mean square of a voltage associated with the power applied to the at least one electrode. Irms is the root mean square of a current associated with the power applied to the at least one electrode. T is a threshold value.

25. A tissue segmentation device. The device has at least one active electrode, a return electrode, a mechanical force application mechanism, a voltage sensor, a current sensor, and a controller. The controller is configured to control a power output of the segmentation device. The controller has a processing component, responsive to the voltage sensor and the current sensor, configured to execute the following: (a) derive an impedance to power applied to the at least one electrode; and (b) responsive to the deriving the impedance, assign a circuit status to a circuit comprising the at least one electrode, according to the following: IF (Z>T1), THEN the circuit status is "open"; and IF (Z<T2), THEN the circuit status is "short"; where Z is the impedance; T1 is a first threshold value; and T2 is a second threshold different from the first threshold value.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "cutting mechanism" should be understood to encompass disclosure of the act of "cutting"—whether explicitly discussed or not—and, conversely, were there only disclosure of the act of "cutting", such a disclosure should be understood to encompass disclosure of a "cutting mechanism". Such changes and alternative terms are to be understood to be explicitly included in the description.

The previous description of the disclosed embodiments is provided to enable any person skilled in the art to make or use the present invention defined by the claims. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. A tissue segmentation device, comprising:
   at least one active electrode;
   a return electrode;
   a mechanical force application mechanism;
   a voltage sensor;
   a current sensor; and
   a controller configured to control a power output of the segmentation device, the controller comprising a processing component, responsive to the voltage sensor and the current sensor, configured to execute the following:
   (a) derive a power factor of power applied to the at least one electrode; and
   (b) responsive to the deriving a power factor, assign a circuit status to a circuit comprising the at least one electrode; wherein
   IF (PF≈0) and ((Vrms/Irms)≥T), THEN the circuit status is "open"; and
   IF (PF≈0) and ((Vrms/Irms)<T), THEN the circuit status is "short"; where
   PF is the power factor;
   Vrms is the root mean square of a voltage associated with the power applied to the at least one electrode;
   Irms is the root mean square of a current associated with the power applied to the at least one electrode; and
   T is a threshold value.

2. The device of claim 1, wherein:
   the mechanical force application mechanism is a constant force spring configured to cause the at least one electrode to apply a constant force to tissue; and
   the device is configured to apply the power to the at least one electrode while applying the constant force.

3. The device of claim 1, wherein the threshold value is dependent on a tissue type.

4. The device of claim 1, wherein the threshold value is dependent on a cutting surface area of the at least one active electrode.

5. The device of claim 1, wherein the processing device is further configured to execute the following:
   compare a first rate of travel of the at least one active electrode to at least one of a rate of travel parameter, a second rate of travel of the at least one active electrode, or a first rate of travel of a second active electrode;
   responsive to the comparing a first rate of travel, adjust a tissue segmentation control signal to effectuate a change in at least one of a voltage applied to the at least one active electrode, a current applied to the at least one active electrode, or a power applied to the at least one active electrode.

6. The device of claim 1, wherein the processing device is further configured to execute the following:
   compare a distance of travel of the at least one active electrode to an expected distance of travel parameter of the at least one active electrode; and
   assign a segmentation status to the circuit comprising the at least one active electrode; wherein
   if the circuit status is "open" and the distance of travel is equal to or greater than the expected distance of travel, then the segmentation status is "complete".

7. The device of claim 1, wherein the processing device is further configured to execute the following:
   compare a distance of travel of the at least one active electrode to an expected distance of travel parameter of the at least one active electrode; and
   assign a segmentation status to the circuit comprising the at least one active electrode; wherein
   if the circuit status is "open" and the distance of travel is less than the expected distance of travel, then the segmentation status is "incomplete".

8. The device of claim 1, wherein the processing device is further configured to execute the following:
   responsive to assigning a circuit status of "short", adjust a tissue segmentation control signal to effectuate a change in power applied to the at least one active electrode.

9. The device of claim 1, wherein:
   the mechanical force application mechanism is configured to apply a cutting force to tissue abutting the at least one active electrode, the mechanical force application mechanism responsive to a tissue segmentation control signal from the controller; and
   the processing device is further configured to execute the following:
   (a) compare a first rate of travel of the at least one active electrode to at least one of a rate of travel parameter, a second rate of travel of the at least one active electrode, or a first rate of travel of a second active electrode; and
   (b) responsive to the comparing a first rate of travel, adjust the tissue segmentation control signal to effectuate a change in the cutting force applied to the at least one active electrode by the mechanical force application mechanism.

10. The device of claim 1, further comprising:
a temperature sensor for detecting a temperature of tissue being segmented; and wherein the controller is configured to execute the following:
responsive to an input from the temperature sensor, adjust a tissue segmentation control signal to effectuate a change in at least one of a voltage applied to the at least one active electrode, a current applied to the at least one active electrode, or a power applied to the at least one active electrode.

11. The device of claim 1, further comprising:
a force sensor for detecting a force being applied to tissue being segmented by the mechanical force application mechanism; and wherein
the controller is configured to execute the following:
responsive to an input from the force sensor, adjust a tissue segmentation control signal to effectuate a change in at least one of a voltage applied to the at least one active electrode, a current applied to the at least one active electrode, or a power applied to the at least one active electrode.

12. The device of claim 1, wherein:
the at least one active electrode is a flexible wire configured to form a loop at a distal end of the segmentation device; and
the mechanical force application mechanism is a spring configured to bias the at least one active electrode towards a proximal end of the segmentation device.

13. A controller for a tissue segmentation device having at least one active electrode, a return electrode, a voltage sensor, a current sensor, and a mechanical force application mechanism, the controller comprising:
a processing component, responsive to the voltage sensor and a current sensor, configured to execute the following:
derive a power factor of power applied to the at least one electrode; and
responsive to the deriving a power factor, assign a circuit status to a circuit comprising the at least one electrode; wherein
IF (PF≈0) and ((Vrms/Irms)≥T), THEN the circuit status is "open"; and
IF (PF≈0) and ((Vrms/Irms)<T), THEN the circuit status is "short"; where
PF is the power factor;
Vrms is the root mean square of a voltage associated with the power applied to the at least one electrode;
Irms is the root mean square of a current associated with the power applied to the at least one electrode; and
T is a threshold value.

14. The controller of claim 13, wherein the mechanical force application mechanism comprises a constant force spring.

15. The controller of claim 14, wherein the threshold value is dependent on a tissue type.

16. The controller of claim 13, wherein the threshold value is dependent on a cutting surface area of the at least one active electrode.

17. The controller of claim 13, wherein the processing device is further configured to execute the following:
compare a first rate of travel of the at least one active electrode to at least one of a rate of travel parameter, a second rate of travel of the at least one active electrode, or a first rate of travel of a second active electrode;
responsive to the comparing a first rate of travel, adjust a tissue segmentation control signal to effectuate a change in at least one of a voltage applied to the at least one active electrode, a current applied to the at least one active electrode, or a power applied to the at least one active electrode.

18. The controller of claim 13, wherein the processing device is further configured to execute the following:
compare a distance of travel of the at least one active electrode to an expected distance of travel parameter of the at least one active electrode; and
assign a segmentation status to the circuit comprising the at least one active electrode; wherein
if the circuit status is "open" and the distance of travel equals the expected distance of travel, then the segmentation status is "complete".

19. The controller of claim 13, wherein the processing device is further configured to execute the following:
compare a distance of travel of the at least one active electrode to an expected distance of travel parameter of the at least one active electrode; and
assign a segmentation status to the circuit comprising the at least one active electrode; wherein
if the circuit status is "open" and the distance of travel is less than the expected distance of travel, then the segmentation status is "incomplete".

20. The controller of claim 13, wherein the processing device is further configured to execute the following:
responsive to assigning a circuit status of "short", adjust a tissue segmentation control signal to effectuate a change in power applied to the at least one active electrode.

21. The controller of claim 13, wherein:
the mechanical force application mechanism is configured to apply a cutting force to tissue abutting the at least one active electrode, the mechanical force application mechanism responsive to a tissue segmentation control signal from the controller; and
the processing device is further configured to execute the following:
(c) compare a first rate of travel of the at least one active electrode to at least one of a rate of travel parameter, a second rate of travel of the at least one active electrode, or a first rate of travel of a second active electrode; and
(d) responsive to the comparing a first rate of travel, adjust the tissue segmentation control signal to effectuate a change in the cutting force applied to the at least one active electrode by the mechanical force application mechanism.

22. The controller of claim 13, wherein the processing device is further configured to execute the following:
responsive to an input from a temperature sensor, adjust a tissue segmentation control signal to effectuate a change in at least one of a voltage applied to the at least one active electrode, a current applied to the at least one active electrode, or a power applied to the at least one active electrode.

23. The controller of claim 13, further comprising:
a force sensor for detecting a force being applied to tissue being segmented by the mechanical force application mechanism; and wherein
the controller is configured to execute the following:
responsive to an input from the force sensor, adjust a tissue segmentation control signal to effectuate a change in at least one of a voltage applied to the at least one active electrode, a current applied to the at least one active electrode, or a power applied to the at least one active electrode.

24. A method of tissue segmentation, comprising:
providing a tissue segmentation device having at least one active electrode, a return electrode, a mechanical force application mechanism, a voltage sensor, and a current sensor,
deriving a power factor of power applied to the at least one electrode; and
responsive to the deriving a power factor, assigning a circuit status to a circuit comprising the at least one electrode; wherein
IF $(PF \approx 0)$ and $((Vrms/Irms) \geq T)$, THEN the circuit status is "open"; and
IF $(PF \approx 0)$ and $((Vrms/Irms) < T)$, THEN the circuit status is "short"; where
PF is the power factor;
Vrms is the root mean square of a voltage associated with the power applied to the at least one electrode;
Irms is the root mean square of a current associated with the power applied to the at least one electrode; and
T is a threshold value.

25. The method of claim 24, wherein, the method comprises:
applying a mechanical cutting force to the at least one electrode while applying the power to the at least one electrode.

26. The method of claim 24, wherein the threshold value is dependent on at least one of a tissue type or a cutting surface area of the at least one active electrode.

27. The method of claim 24, further comprising:
comparing a first rate of travel of the at least one active electrode to at least one of a rate of travel parameter, a second rate of travel of the at least one active electrode, or a first rate of travel of a second active electrode;
responsive to the comparing a first rate of travel, adjusting a tissue segmentation control signal to effectuate a change in at least one of a voltage applied to the at least one active electrode, a current applied to the at least one active electrode, or a power applied to the at least one active electrode.

28. The method of claim 24, further comprising:
comparing a distance of travel of the at least one active electrode to an expected distance of travel parameter of the at least one active electrode; and
assigning a segmentation status to the circuit comprising the at least one active electrode; wherein
if the circuit status is "open" and the distance of travel equals the expected distance of travel, then the segmentation status is "complete".

29. The method of claim 24, further comprising:
responsive to assigning a circuit status of "short", adjusting a tissue segmentation control signal to effectuate a change in power applied to the at least one active electrode.

30. A tissue segmentation device, comprising:
at least one active electrode;
a return electrode;
a mechanical force application mechanism;
a voltage sensor;
a current sensor; and
a controller configured to control a power output of the segmentation device, the controller comprising a processing component, responsive to the voltage sensor and the current sensor, configured to execute the following:
(c) derive an impedance to power applied to the at least one electrode; and
(d) responsive to the deriving the impedance, assign a circuit status to a circuit comprising the at least one electrode; wherein
IF $(Z > T1)$, THEN the circuit status is "open"; and
IF $(Z < T2)$, THEN the circuit status is "short"; where
Z is the impedance;
T1 is a first threshold value; and
T2 is a second threshold different from the first threshold value.

* * * * *